US012004799B2

(12) United States Patent
Beaupre et al.

(10) Patent No.: US 12,004,799 B2
(45) Date of Patent: Jun. 11, 2024

(54) ELECTROSURGICAL SYSTEMS AND METHODS

(71) Applicants: Jean Beaupre, Alexandria, KY (US); Richard Grant, Cincinnati, OH (US); William Bookwalter, Boston, MA (US); Robert Dunki-Jacobs, Mason, OH (US); REACH SURGICAL, INC., Tianjin (CN)

(72) Inventors: Jean Beaupre, Alexandria, KY (US); Richard Grant, Cincinnati, OH (US); William Bookwalter, Boston, MA (US); Robert Dunki-Jacobs, Mason, OH (US)

(73) Assignee: REACH SURGICAL, INC., Tianjin (CN)

( * ) Notice: Subject to any disclaimer, the term of this patent is extended or adjusted under 35 U.S.C. 154(b) by 1054 days.

(21) Appl. No.: 16/623,227

(22) PCT Filed: Jun. 15, 2018

(86) PCT No.: PCT/US2018/037925
§ 371 (c)(1),
(2) Date: Dec. 16, 2019

(87) PCT Pub. No.: WO2018/232360
PCT Pub. Date: Dec. 20, 2018

(65) Prior Publication Data
US 2021/0022792 A1 Jan. 28, 2021

Related U.S. Application Data

(60) Provisional application No. 62/520,529, filed on Jun. 15, 2017.

(51) Int. Cl.
*A61B 18/14* (2006.01)
*A61B 1/00* (2006.01)
(Continued)

(52) U.S. Cl.
CPC ...... *A61B 18/1206* (2013.01); *A61B 1/00112* (2013.01); *A61B 1/313* (2013.01);
(Continued)

(58) Field of Classification Search
CPC . A61B 18/1206; A61B 1/00112; A61B 1/313; A61B 17/3421; A61B 17/3476;
(Continued)

(56) References Cited

U.S. PATENT DOCUMENTS 5,573,424 A 11/1996 Poppe
5,829,987 A 11/1998 Fritsch et al.
(Continued)

FOREIGN PATENT DOCUMENTS

WO 2016157504 10/2016

OTHER PUBLICATIONS

Supplementary European Search Report for app. No. EP18816880 (corresponding to PCT/US2018/037925), dated Apr. 29, 2020.
(Continued)

*Primary Examiner* — Sean W Collins
(74) *Attorney, Agent, or Firm* — Porter Wright Morris & Arthur LLP

(57) ABSTRACT

An engagement detection system ("EDS") adapted to be positioned between, and in electrical communication with, an electrosurgical generator and an electrosurgical instrument. The EDS adapted to electronically detect that the electrosurgical instrument is inserted into a trocar cannula, and thereafter deliver electrosurgical energy to the instrument. A method of operating an endoscopic electrosurgical instrument inserted into a trocar cannula, as well as a switch assembly are also provided.

21 Claims, 38 Drawing Sheets

(51) Int. Cl.
*A61B 1/313* (2006.01)
*A61B 17/34* (2006.01)
*A61B 18/12* (2006.01)
*A61B 18/16* (2006.01)
*A61B 17/00* (2006.01)
*A61B 18/00* (2006.01)
*A61B 90/00* (2016.01)

(52) U.S. Cl.
CPC ...... *A61B 17/3421* (2013.01); *A61B 17/3476* (2013.01); *A61B 18/1233* (2013.01); *A61B 18/1445* (2013.01); *A61B 18/16* (2013.01); *A61B 2017/0003* (2013.01); *A61B 2017/00973* (2013.01); *A61B 2018/00172* (2013.01); *A61B 2018/00178* (2013.01); *A61B 2018/00708* (2013.01); *A61B 2018/1253* (2013.01); *A61B 2018/126* (2013.01); *A61B 2090/0808* (2016.02)

(58) Field of Classification Search
CPC ........ A61B 18/1233; A61B 2017/0003; A61B 2017/00973; A61B 2018/00178; A61B 2018/00708; A61B 2090/0808
See application file for complete search history.

(56) References Cited

U.S. PATENT DOCUMENTS

| | | |
|---|---|---|
| 5,916,215 A | 6/1999 | Long et al. |
| 5,921,783 A | 7/1999 | Fritsch et al. |
| 5,925,041 A | 7/1999 | Long et al. |
| 5,936,536 A * | 8/1999 | Morris .................. A61B 18/14 340/693.5 |
| 5,954,520 A | 9/1999 | Schmidt |
| 5,961,514 A * | 10/1999 | Long ..................... A61B 17/34 606/41 |
| 6,106,519 A | 8/2000 | Long et al. |
| 6,569,163 B2 | 5/2003 | Hata et al. |
| 6,692,489 B1 | 2/2004 | Heim et al. |
| 8,449,460 B2 | 5/2013 | Duke et al. |
| 9,421,060 B2 | 8/2016 | Monson et al. |
| 9,532,827 B2 | 1/2017 | Morgan et al. |
| 11,045,223 B2 | 6/2021 | Beaupre |
| 2005/0070947 A1 | 3/2005 | Franer et al. |
| 2013/0096549 A1* | 4/2013 | Organ ................ A61B 18/1206 606/41 |
| 2013/0324991 A1 | 12/2013 | Clem et al. |
| 2014/0074134 A1 | 3/2014 | Skarbnik et al. |
| 2015/0057653 A1 | 2/2015 | Sugiyama |
| 2015/0100053 A1* | 4/2015 | Livneh ............... A61B 18/1482 606/34 |
| 2015/0289925 A1 | 10/2015 | Voegele et al. |
| 2015/0359565 A1 | 12/2015 | Matsui |
| 2016/0192980 A1 | 7/2016 | Newton et al. |
| 2016/0353969 A1* | 12/2016 | Kikuchi .................. A61B 34/20 |
| 2017/0332881 A1 | 11/2017 | Matsuki et al. |
| 2020/0085488 A1* | 3/2020 | Ramin ............... A61B 18/1206 |
| 2022/0015802 A1 | 1/2022 | Beaupre |

OTHER PUBLICATIONS

International Search Report and Written Opinion for PCT/US2018/037925, dated Oct. 24, 2018.

* cited by examiner

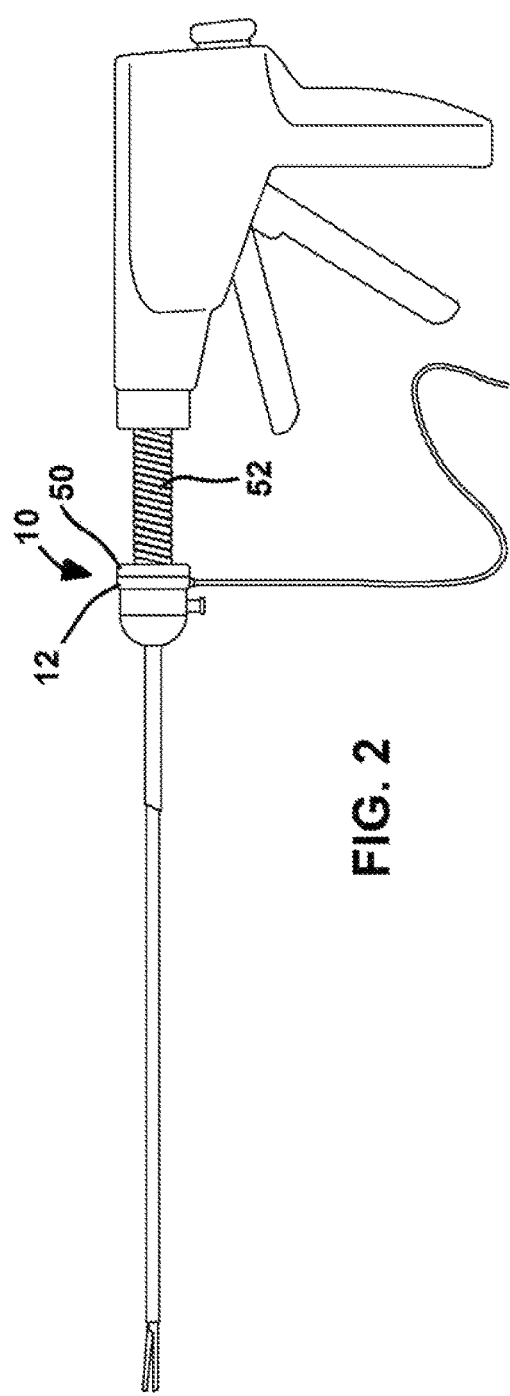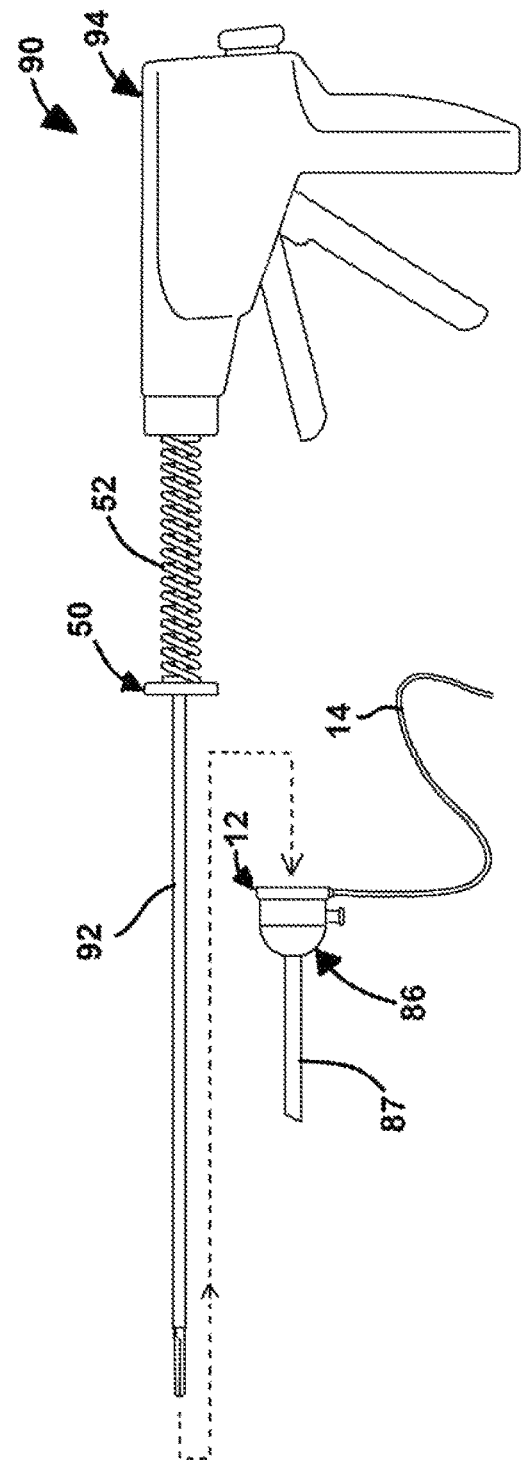
FIG. 2
FIG. 1

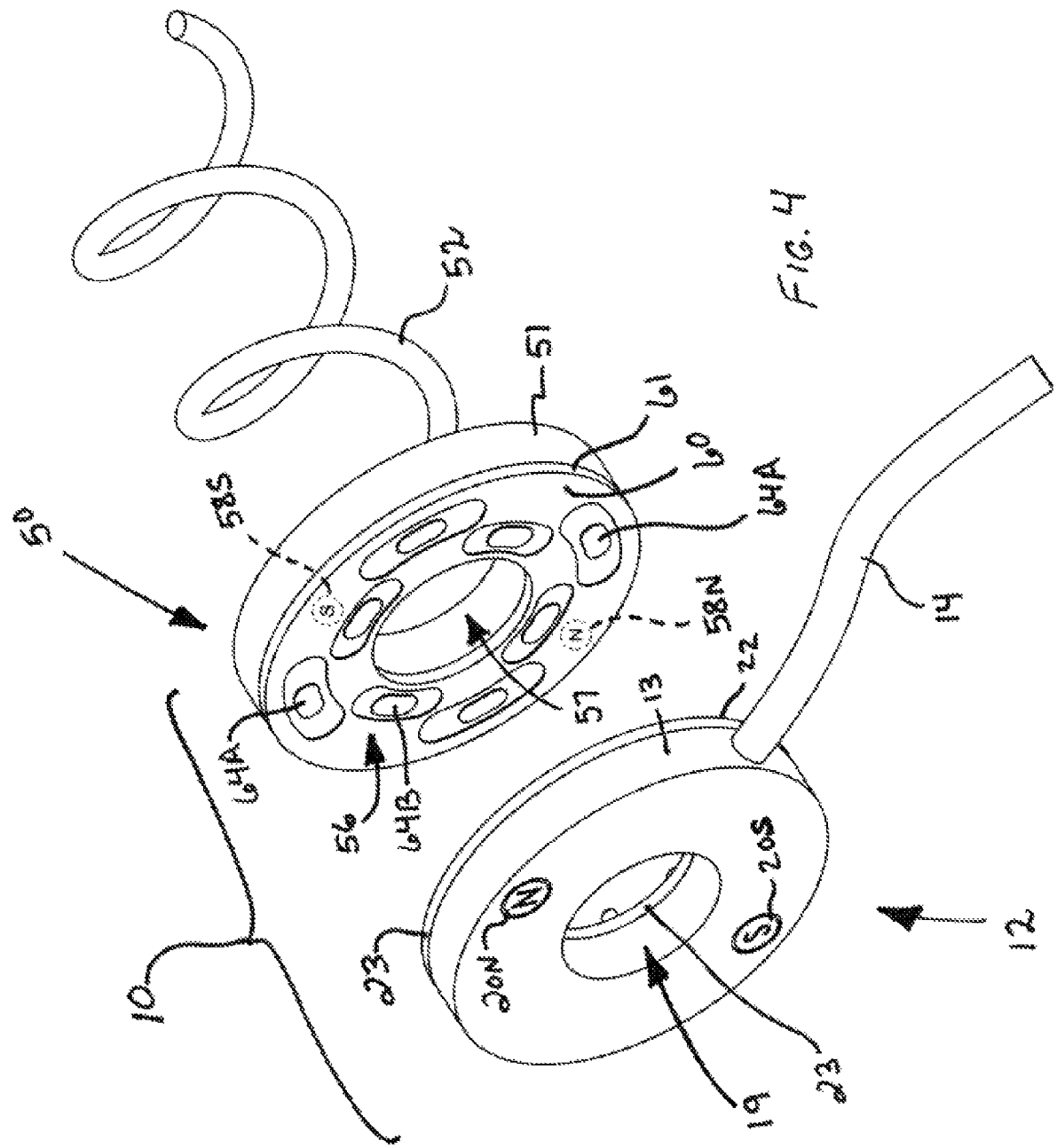

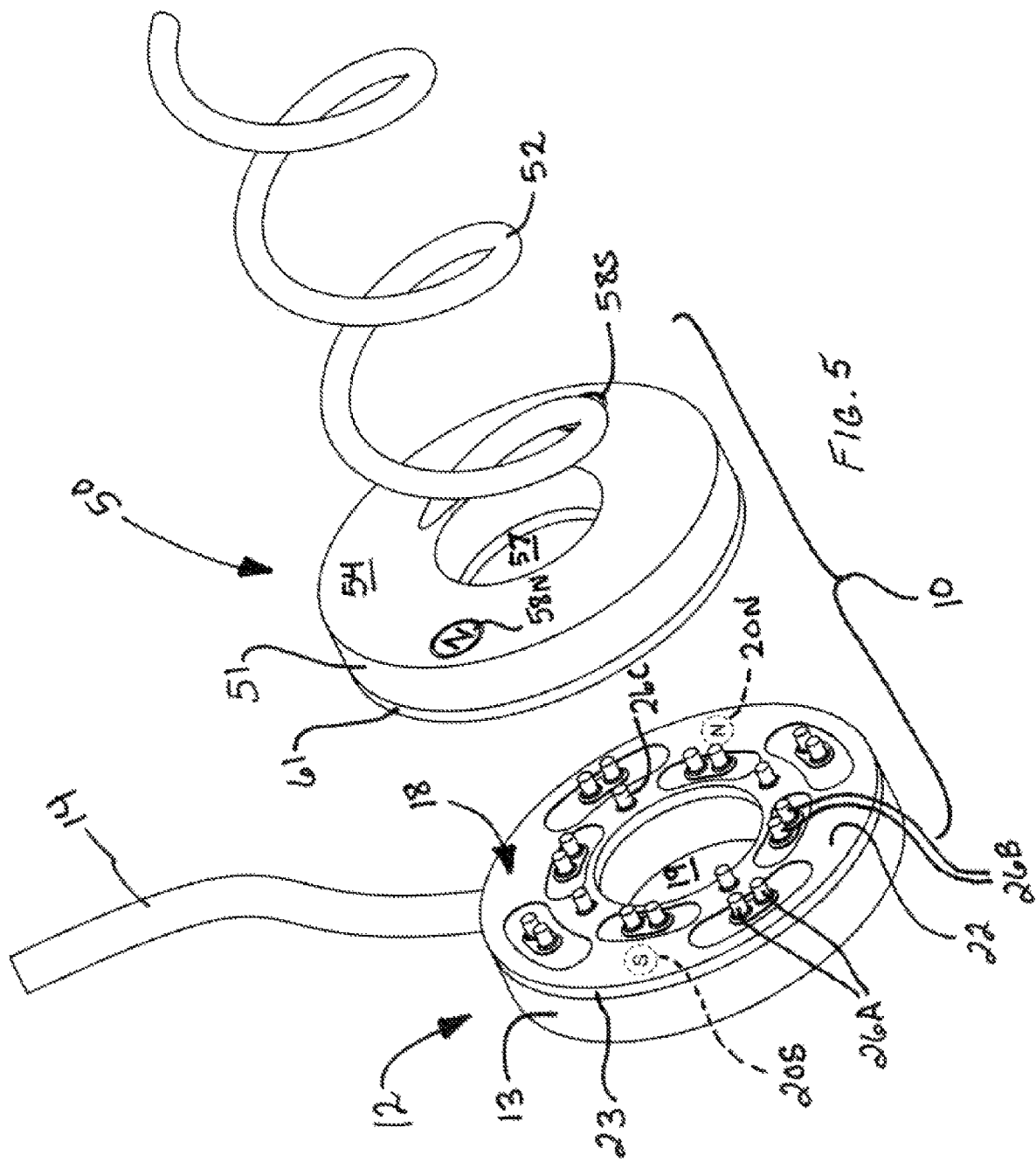

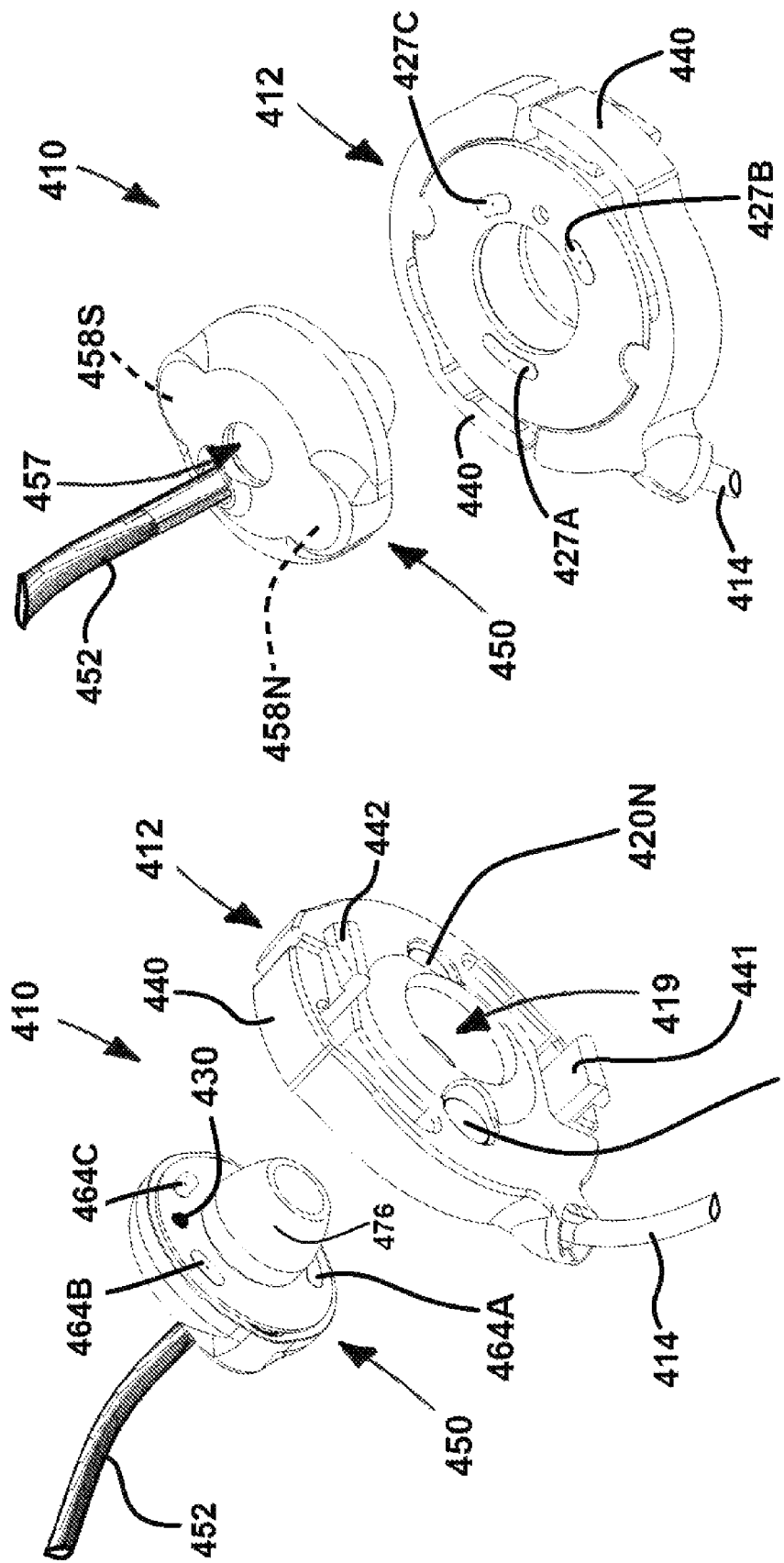

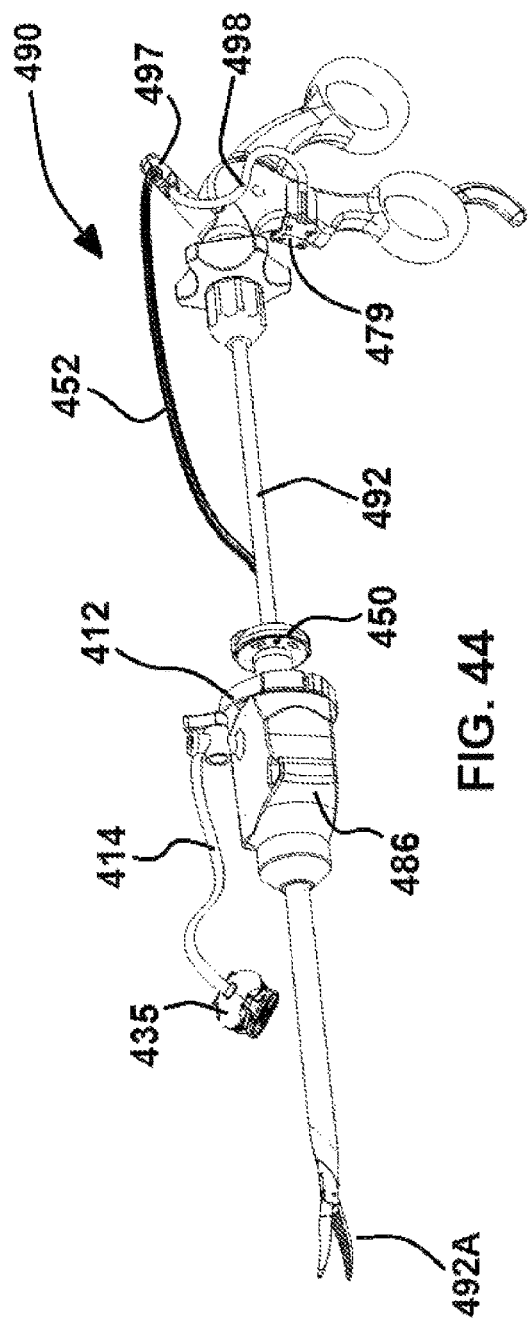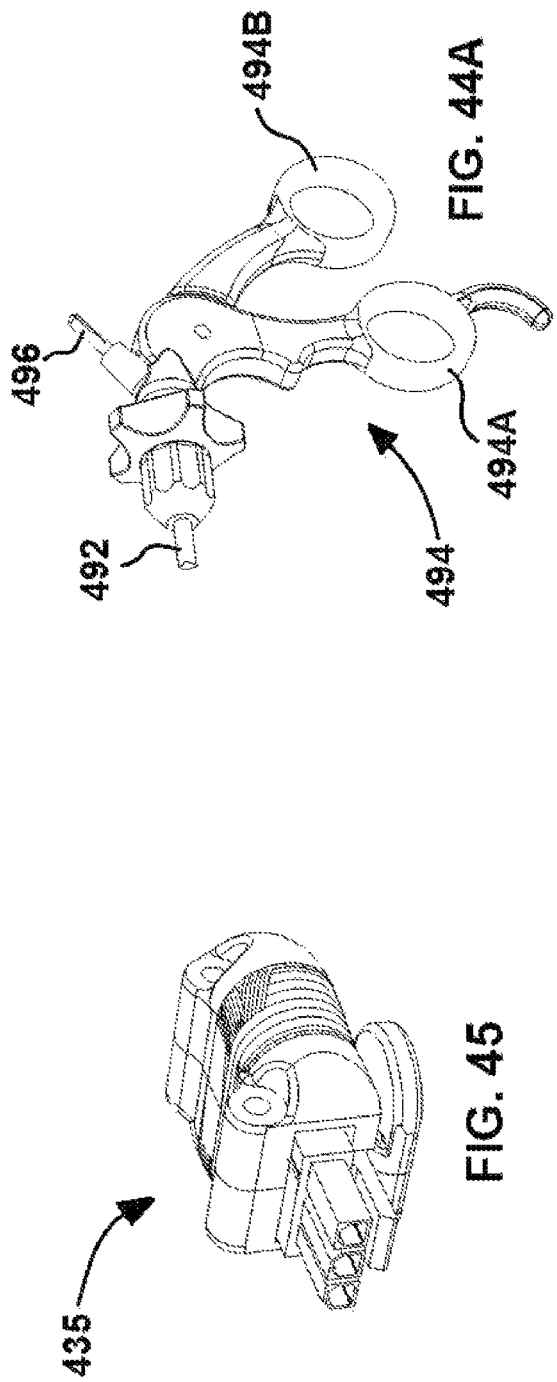
FIG. 44
FIG. 44A
FIG. 45

ELECTROSURGICAL SYSTEMS AND METHODS

CROSS REFERENCE TO RELATED APPLICATIONS

This application claims priority to U.S. Provisional Patent Application No. 62/520,529, filed on Jun. 15, 2017, entitled "ELECTROSURGICAL SYSTEMS AND METHODS." This application is also related to U.S. Provisional Patent Application No. 62/266,149, filed on Dec. 11, 2015, entitled "MODULAR SIGNAL INTERFACE SYSTEM AND POWERED TROCAR," and PCT Patent App. No. PCT/US16/66044, filed on Dec. 11, 2016, entitled "MODULAR SIGNAL INTERFACE SYSTEM AND POWERED TROCAR." The entire disclosures of the foregoing patent applications are incorporated by reference herein. PCT Patent App. No. PCT/US16/66044 published as International Pub. No. WO 2017/100728 A1, on Jun. 15, 2017 (hereinafter, "WO728").

BACKGROUND

Endoscopic medical procedures, particularly endoscopic surgery, continue to become more and more prevalent. In these procedures, one or more openings in tissue are created in order to provide access to anatomical cavities and other internal structures within a patient. As used herein, "endoscopic" refers to procedures, which are performed through one, or more openings (e.g., incisions) in a patient's tissue, such as one or more openings made in the abdominal wall. Various instruments, including, for example, tubular optical instruments (e.g., endoscopes) are inserted into the patient though these openings to manipulate internal structures, perform various procedures, and/or, in the case of an endoscope, to provide vision within the patient. The term "endoscopic" is generic to, and therefore includes, for example, terms such as "laparoscopic" and "arthroscopic," which refer to the use of an endoscope in a particular region of the body.

Whether the instrument to be inserted into the patient is an endoscope (through which other instruments may thereafter be inserted) or a simple surgical instrument such as a grasper, a cannula is first passed through an opening in the tissue wall into an anatomical cavity (or other internal region in the patient). Thereafter, the endoscope or other surgical instrument is inserted through the cannula into the anatomical cavity. The cannula provides a passageway that remains available for use during the surgical procedure, providing access to the anatomical cavity and the ability to insert and remove various instruments throughout the procedure.

One commonly employed instrument for penetrating tissue and positioning a cannula therein is referred to as a "trocar." Trocars generally comprise an obturator for creating an opening in tissue, and an outer cannula (also referred to as the trocar cannula or sleeve). As used herein, unless the context indicates otherwise, the term "trocar" refers to the assembly comprising the cannula and the associated cannula housing at the proximal end of the cannula. The distal end of the cannula is positioned against the patient's skin, and the obturator is positioned within the interior of the cannula. With the sharp distal end of the obturator protruding beyond the distal end of the cannula, the distal end of the obturator is urged through the tissue (e.g., skin, underlying fascia, and fat) until it enters the targeted anatomical cavity. The cannula is urged through the tissue opening created by the obturator, typically following closely behind the sharp distal tip of the obturator. Once the distal end of the cannula is in the desired location in the anatomical cavity, the obturator is withdrawn from the cannula. The cannula remains in place, and provides a passageway through which access to the anatomical cavity is provided.

In many instances, various type of powered or otherwise wired surgical instruments are used in endoscopic procedures, including, for example, endoscopes, electrosurgical instruments (bipolar and monopolar, e.g., bipolar forceps), ultrasonic instruments (e.g., ultrasonic blades), DC-powered devices, etc. However, each of these instruments typically requires one or more cables for transmitting power and/or data between the instrument and other equipment (e.g., a power supply, an RF or ultrasonic generator, a signal processing device, a display device, etc.) in the surgical environment. Electrical cables and the like can be cumbersome during surgery or other endoscopic medical procedures, often interfering with the procedure itself. This problem (and others) is exacerbated by the need to use multiple powered or otherwise wired instruments during a procedure. Furthermore, although a variety of cordless surgical instruments such as ultrasonic cutting/cautery and radio frequency cutting/cautery instruments have been developed, such instruments rely upon a power supply (e.g., a battery) located within the instrument itself. This adds additional weight as well as manufacturing costs.

While a variety of devices and techniques may exist for providing electrical communication with an instrument used through a trocar cannula, it is believed that no one prior to the inventor(s) has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. Some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIGS. 1 and 2 depict a schematic view of one embodiment of a modular signal interface system ("MSIS"), comprising a signal interface adapter mounted on a trocar cannula housing and an instrument connector mounted on the shaft of a surgical instrument. In FIG. 2, the signal interface adapter and instrument connector are in mating engagement, with the shaft of the surgical instrument fully extended into the trocar cannula.

FIG. 4 is a perspective view of the MSIS of FIG. 1.

FIG. 5 is a perspective view of the MSIS of FIG. 4, wherein the viewing angle is rotated from that of FIG. 4 such that the proximal face of the signal interface adapter is visible (rather than the distal face, as in FIG. 4).

FIGS. 9 and 10 are perspective views of an alternative embodiment of a MSIS, wherein FIG. 9 is a view similar to that of FIG. 4 and FIG. 10 is a view similar to that of FIG. 5.

FIGS. 39 and 40 are perspective views of an alternative embodiment of a MSIS, the views similar to those of FIGS. 9 and 10, respectively.

FIG. 44 is a perspective view of yet another surgical instrument, having an alternative embodiment of a MSIS and associated trocar, with FIG. 44A depicting the handle portion of the instrument without the connections to the instrument connector.

FIG. 45 is a perspective view of a connector of the instrument of FIG. 44.

Figure 3:
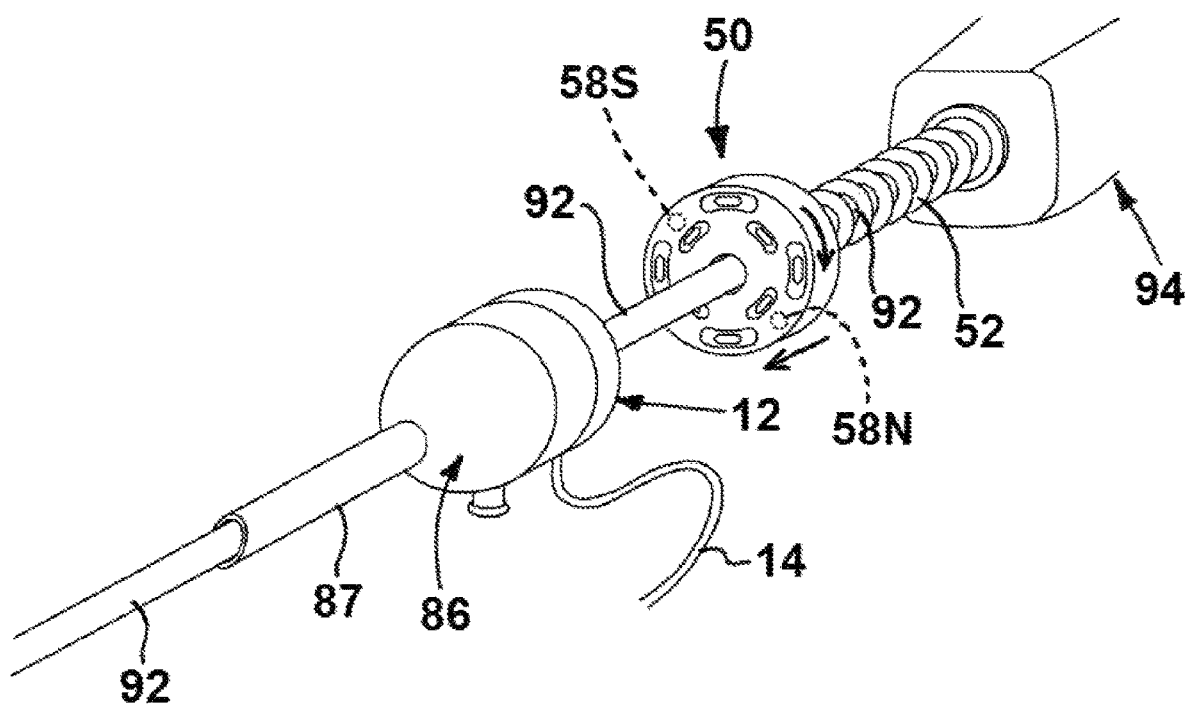
FIG. 3 depicts a schematic view of the MSIS of FIG. 1, wherein the instrument connector is being advanced towards the signal interface adapter under the influence of magnetic force.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

As used herein, unless the context indicates otherwise, the term "cable" is intended to encompass signal-conducting devices comprising an assembly of two or more conductors such as wires (single or multiple strand), and other types of physical conduits, traces or lines that conduct electrical signals, whether power signals (e.g., DC or AC power) or communication signals (e.g., a voltage or current indicative of a sensed condition, a video, image or audio signal, etc.). As also used herein, the phrase "in electrical communication" means that the electrical signals can be transmitted between the two components, such as via one or more wires, conduits, traces, lines, terminal blocks, posts, solder joints, integrated circuit traces, and the like, or through direct contact of the two components.

WO728 describes and depicts a modular signal interface system ("MSIS") for communicating one or more electrical signals between, for example, a surgical cannula and an instrument inserted into the cannula. For the sake of clarity, the first portion of the present application describes certain aspects of the MSIS described in WO728. Aspects of the present disclosure provide alternative embodiments of a MSIS and components thereof. Other aspects of the present disclosure pertain to an engagement detection system ("EDS") that employs or takes advantage of aspects of the MSIS and components thereof, including the MSIS of WO728 as well as the alternative MSIS embodiments and components thereof described herein.

Embodiments of the MSIS of WO728 and that of the present disclosure generally include: (1) a signal interface adapter provided on, or configured to be mounted on, a cannula (e.g., a surgical trocar); and (2) an instrument connector configured to matingly engage the cannula-mounted signal interface adapter. The mating engagement provides electrical communication between the signal interface adapter and the instrument connector over one or more communication channel, such that one or more electrical signals can be communicated (e.g., passed) between the signal interface adapter and the instrument connector. These electrical signals can comprise, for example, power signals (e.g., current or voltage) and/or communication signals (e.g., sensor signals).

In one embodiment, the signal interface adapter is configured to be affixed to a cannula (permanently or removably), particularly at the proximal end of the cannula (i.e., the end which remains outside of the patient during use). A cable, operatively attached to the signal interface adapter, communicates one or more electrical signals between the signal interface adapter and another device (e.g., a power supply, an RF or ultrasonic generator, a signal processing device, a display device, etc.). The signal interface adapter provides an interface for electrical communications between the instrument connector of the MSIS and the other device connected to the interface adapter, without the need for a wired connection between the surgical instrument itself and the other device.

By way of example, in some embodiments the mating engagement between the interface adapter and the instrument connector allows power for operating a surgical instrument to be delivered to the instrument via the signal interface adapter rather than via a cable attached to, and extending away from the surgical instrument itself. In this embodiment, there is no need for a cord or other electrical conduit to be attached to the instrument that could interfere with medical procedures or a medical practitioner performing medical procedures. Instead, external electrical connectivity (e.g., to a power supply or other device) is provided by the cannula-mounted signal interface adapter and a cable or other conduit(s) attached thereto.

In some embodiments, the MSIS allows for a variety of cordless, signal-associated instruments such as various powered surgical instruments to be used with a cannula, such that electrical signals necessary for operation of the instrument (e.g., power, sensor signals, etc.) are communicated via the signal interface adapter on the cannula rather than by a cord attached to the surgical instrument itself. This can obviate the need, for example, to physically connect each instrument to an external power supply (e.g., via a cable) prior to use. Instead, the interface adapter on the cannula is connected to an external power supply, and the mating engagement of the interface adapter and the instrument connector allows power to be supplied to the instrument via the interface adapter on the cannula. Multiple surgical instruments can be used in this way during a surgical procedure, with only a single cable supplying power to each instrument via the signal interface adapter. In addition, in some embodiments the signal interface adapter is configured such that it will not interfere with the use of conventional surgical instruments (i.e., instruments used without the instrument connector of the signal interface system) through the cannula.

Mating engagement of the interface adapter and the instrument connector is accomplished in a variety of ways. In some embodiments, mating engagement is accomplished magnetically. Complementary magnetic regions on both the interface adapter and the instrument connector provide not only the necessary force for magnetically engaging the interface adapter and instrument connector, but also are arranged so as to ensure or facilitate proper alignment of that engagement. When the interface adapter and the instrument connector are alignably engaged with one another, conductive contacts on the interface adapter will be in contacting relationship with corresponding conductive contacts on the instrument connector such that electrical continuity is established between the contacts, thereby allowing electrical signals to pass between predetermined pairs of contacts that are in contacting relationship with one another. The conductive contacts can have any of a variety of forms, including planar contacts as well as elongated contacts (e.g., conductive pins such as pogo pins).

In some embodiments, the signal interface adapter is configured for removable attachment to a trocar cannula (e.g., removable attachment to the proximal end of a cannula housing). In other embodiments, the signal interface adapter is integrated into the cannula assembly, particularly at the proximal end thereof, and therefore is not intended to be removed from the cannula.

In general, the surgical instruments with which the MSIS described herein can be used have an elongate shaft that is adapted to be received within the interior passageway of a surgical cannula. Embodiments of the instrument connector component of the interface system include a central aperture through which the instrument shaft is received. In particular embodiments, the instrument shaft is slidingly received through the central aperture of the instrument connector such that the connector can slide axially and rotatingly along at least a portion of the instrument shaft. In some embodiments, the instrument connector is electrically connected to the instrument (e.g., to the instrument body) by an externally or internally routed cable.

The MSIS and EDS embodiments described herein can be used with a wide variety of signal-associated surgical instruments. As used herein, a "signal-associated surgical instrument" is a surgical instrument that receives and/or supplies one or more electrical signals to an external device, wherein those electrical signals can comprise power signals (e.g., current or voltage) and/or communication signals (e.g., a sensor signal). Signal-associated surgical instruments include powered surgical instruments (particularly those configured for use though a cannula), as well as, for example, instruments used for: ultrasonic cutting/cautery, ultrasonic imaging, focused ultrasound, radio frequency cautery, radio frequency cutting, radio frequency ablation, stapling, sensing, imaging, measuring, robotic, haptic, cutting, grinding, clamping, thermal, radio-isotopic, drug delivery, biopsy, hyperspectral imaging, insufflation, and/or suturing.

Embodiments of the MSIS also include a retrofittable hand switch assembly that is adapted for attachment to a surgical instrument that does not include hand switch control. The hand switch assembly is in electrical communication with the instrument connector of the MSIS and can be used to control the operation of an external electrical device (e.g., an RF generator) operatively coupled to the signal interface adapter of the MSIS. Embodiments of the EDS provide electrical communication between the signal interface adapter and the external electrical device.

Embodiments of the present disclosure also include an engagement detection system ("EDS") adapted to be positioned between, and in electrical communication with, an electrosurgical generator (or other external electrical device) and a surgical instrument (e.g., monopolar forceps). While not so limited, embodiments of the EDS are adapted for use in conjunction with the MSIS. The EDS is adapted to electronically detect that a signal-associated surgical instrument (e.g., an electrosurgical instrument) has been inserted into a trocar cannula, and to thereafter deliver electrosurgical energy to the instrument. In some embodiments, the EDS is configured such that electrosurgical energy can only be transmitted from the generator to the instrument when the instrument is inserted into the trocar cannula.

One embodiment of the EDS includes a first connector for operably connecting the EDS to a surgical instrument, a second connector for operably connecting the EDS to an electrosurgical generator, a first switch mediating electrical communication between the first connector and the second connector; a control circuit adapted to receive an electronic signal indicative of the electrosurgical instrument being inserted into a trocar cannula and generate a switch signal for controlling operation of the first switch. The control circuit can take a variety of different forms, and include a variety of components. In some embodiments the control circuit includes one or more processors such as a microprocessor (along with memory and I/O devices, either stand-alone or as part of a microcontroller having the microprocessor), and/or an application specific integrated circuit(s) (ASIC). For example, some embodiments make extended use of a microprocessor (e.g., as part of a microcontroller) programmed to determine that the shaft of a surgical instrument has been inserted into a trocar cannula and is therefore ready for use. An advantage of the use of a microprocessor (e.g., in the form of a microcontroller) is that it can also perform other functions such as monitoring system status and performance, controlling one or more indicators (visual, e.g., LEDs, audible and/or tactile indicators) that signal the device operator of status, and/or controlling EDS output.

By way of example, and as further detailed herein, the control circuit can comprise a microprocessor. The microprocessor can be in the form of a microcontroller, or can have separate memory, analog-to-digital converter(s), I/O devices, etc., not shown in the figures. Alternatively, an analog circuit or other device or circuitry capable of logically controlling relays or other switches in the EDS can be used in place of (or in addition to) a microprocessor. For example, one embodiment of the EDS described herein includes one or more comparators adapted for comparing a signal received from the instrument or the trocar cannula (e.g., from the MSIS) to a plurality of reference signals, as well as at least one AND Gate for receiving outputs from the comparator(s) and providing at least one closure signal for a relay or other switch in the EDS.

Some embodiments of the EDS include two or more switches (e.g., reed relays), with the control circuit further adapted to receive a switching signal from a switching device (e.g., a user-operated hand switch) and, in response to said switching signal, cause an actuation signal to be supplied to the electrosurgical generator for controlling electrosurgical energy supplied by the generator.

The EDS detects whether the instrument connector of the MSIS is in operative engagement with the signal interface adapter of the MSIS. Connection detection can be used, for example, to determine that a compatible surgical instrument having an instrument connector has been inserted into a trocar having the signal interface adapter of the MSIS. In other words, the EDS can detect whether the instrument is in the patient's body ready for use, rather than laying on the patient or table. When operative engagement is confirmed, the EDS establishes electrical communication between the generator (or other external electrical device) and the instrument (via the MSIS). Thus, electrosurgical energy is only delivered to the MSIS and the surgical instrument when, and in some instances only so long as, the electrosurgical instrument is inserted into the cannula. For example, if the instrument is withdrawn from the cannula such that the instrument connector disengages from the signal interface adapter, delivery of electrosurgical energy to the MSIS and the instrument is halted. Among other things, this provides added safety for both the patient and medical personnel, as electrosurgical energy is not delivered if the instrument is removed from the trocar—even if someone inadvertently actuates a control switch for selective energization (e.g., by inadvertently stepping on a footswitch while the instrument is not in use).

In some embodiments, the EDS is adapted for use with a monopolar electrosurgical generator. Radio frequency ("RF") electrical current is selectively delivered from the generator to the instrument (ultimately, to the active electrode of the instrument) via the EDS, while the return electrode (e.g., a pad positioned beneath the patient) is in electrical communication with the generator in the usual manner (i.e., the return electrode does not communicate with the generator through the EDS). In alternative embodiments, the monopolar return path is also routed through the EDS.

In other embodiments, the EDS is adapted for use with a bipolar electrosurgical generator. RF electrical current is selectively delivered from the generator to the instrument via the EDS. In still further embodiments, the EDS is adapted for use with both monopolar and bipolar RF—either by connecting to two different generators (monopolar and bipolar) or to a single generator capable of providing both treatment modalities. In a still further embodiment, the EDS is adapted for use with an ultrasonic generator.

Embodiments of the EDS are backwards compatible, thereby capable of being used with existing generators and instruments. Embodiments described herein also allow for the addition of hand switching to existing instruments that do not include such feature. Embodiments of the EDS also provide additional safety in the operating room, including reducing the incidence of injuries (to patient and medical personnel) and even fires resulting from the inadvertent activation of an electrosurgical instrument (e.g., a monopolar device) when the instrument is not inserted into a patient (i.e., inserted into a trocar cannula), ready for use.

Operation of the instrument (e.g., monopolar forceps) can be controlled in the typical fashion, such as by means of a footswitch connected to the generator. Indeed, embodiments of the present disclosure can be used with a variety of electrosurgical generators from a variety of manufacturers, using manufacturer-supplied control devices (e.g., footswitches available from the generator manufacturer). In some embodiments, the EDS also transmits control signals to the electrosurgical generator. In some embodiments, a footswitch (or other control device) can be connected to the EDS and its operation used to selectively transmit control signals to the generator. The footswitch can be one supplied by the generator manufacturer that is normally connected directly to the generator (via a footswitch port). In other embodiments, the footswitch is operably connected to the instrument apart from the EDS (e.g., a direct connection between the footswitch and the instrument rather than connecting through the EDS).

In still further embodiments a supplementary switching device (e.g., a hand switch) is provided in electrical communication with either the instrument connector or the signal interface adapter such that the switching device can be used to control the electrosurgical generator. For example, in some embodiments one or more hand switches located on the surgical instrument are used to control operation of the instrument, with the electrical communication between the switches and the generator routed through the MSIS and the EDS. Such hand switches can be used in lieu of (or in combination with) a footswitch, with the EDS transmitting hand switch control signals to the generator such that these signals emulate those provided by a conventional footswitch.

In still further embodiments of the present disclosure, one or more supplementary switching devices (e.g., hand switches) are provided in electrical communication with the MSIS (e.g., the instrument connector portion thereof), and are configured to be used for hand control of the operation of a surgical instrument on which the instrument connector is mounted. These switching devices are particularly useful for controlling a surgical instrument that is not supplied with integrated actuators for controlling the delivery of electrosurgical energy. Such instrument hand switches can even be configured for attachment (e.g., via a pressure-sensitive adhesive) to the surgical instrument, thereby providing hand switch control of an instrument that previously required the use of a footswitch. Thus, hand switches can be retrofit to a surgical instrument that is not normally provided with one (i.e., is originally designed for footswitch operation only). The supplementary switching device can also be disposable (i.e., intended for one-time use), configured for removable attachment to the instrument such as by a releasable adhesive.

While the present disclosure illustrates and describes EDS and other system and method embodiments using the example of monopolar forceps, it will be understood that the embodiments described herein can be used with any of a variety of monopolar surgical instruments. These include, for example, graspers, Maryland Dissectors, scissors, paddles, probes, electrodes, etc., each having an end effector that includes a monopolar electrode. Also, the EDS embodiments described herein can be used with a wide variety of commercially available electrosurgical generators and accessories for such generators. In fact, the EDS can be used with generators from various manufacturers, in most instances merely requiring that connectors compatible with the particular type of generator are provided on the ends of cables operatively connecting to the generator (as well as, for example, cables or other apparatus, such as a footswitch "T", that connects to one or more accessories such as a footswitch).

FIGS. 1-8 depict schematic illustrations of one embodiment of a MSIS (10) comprising a signal interface adapter (12) and an instrument connector (50). In the embodiment shown in these figures, signal interface adapter (12) is mounted on the proximal end of a trocar cannula housing (86) having a cannula (87) extending distally therefrom. The instrument connector (50) is slidingly mounted on the elongate shaft (92) of a powered surgical instrument (90) that extends distally away from the instrument body (94) (also commonly referred to as the instrument handle). In this particular example, the instrument (90) is an electrosurgical cutter/stapler device of known construction. However, the MSIS and EDS of the present disclosure can be used with any of a variety of other surgical devices, including electrosurgical devices.

As best seen in FIGS. 4 and 5, the signal interface adapter (12) generally comprises a housing (13) and a cover plate (23) mounted thereto. A main cable (14) is operatively connected to the signal interface adapter (12) at one end, and the other end of the main cable (14) (not shown) is adapted for operative connection to an external electrical device (e.g., a power supply or an RF or ultrasonic generator) for supplying electrical signals to, and in some instances receiving electrical signals from, the interface adapter (12). In embodiments further described herein, the operative connection of the main cable (14) to the external electrical device (e.g., a generator) is through the engagement detection system ("EDS") (i.e., the EDS is configured to be located between the signal interface adapter and the external electrical device such as an RF generator).

Main cable (14) can include any number of electrical conduits, in some instances corresponding to the number of distinct communication channels established when the contacts on the interface adapter (12) conductively contact corresponding contacts on the instrument connector (50). In some embodiments wherein an EDS is used as the interface between the MSIS and an external electrical device, the MSIS can have as few as two or three communication channels.

In the embodiment of FIGS. 1-8, the mating faces of each of the signal interface adapter (12) and the instrument connector (50) have nine conductive contacts arranged about a central aperture, with each contact on a component oriented for conductively contacting a corresponding contact on the other component. Thus, in the embodiment of FIGS. 1-8, nine distinct communication channels between the signal interface adapter (12) and instrument connector (50) are established when these components are in proper mating engagement. Similarly, main cable (14) has, for example, nine independent electrical conduits (e.g., wires) inside an outer sheath—one conduit for each communication channel provided by the MSIS (10).

While the use of these nine channels will vary, in the embodiment of FIGS. 1-8 four of the channels are used for transmitting power signals, and five are used for transmitting communication signals (including one that is used as a "sense line," as further described herein). It will be understood, of course, that any number of mating contacts, and hence communication channels, can be provided (e.g., 2, 3, 4, 5, 6, 7, 8, 9, 10, etc.). Also, the number of mating contacts and communication channels need not correspond to the number of conductors in cable (14). In some instances, the number of mating contacts and communication channels is greater than the number of electrical conduits of cable (14). This can be desirable, for example, when electronic circuitry within interface adapter (12) and/or instrument connector (50)/instrument (90) require one or more communication channels between themselves in addition to those having a corresponding conductor in cable (14). Having more mating contacts and communication channels than the number of electrical conduits of cable (14) can also be advantageous, and in other instances, the number of mating contacts and communication channels is less than the number of electrical conductors in main cable (14) (e.g., when there are one or more redundant conductors in cable (14), such as for safety reasons).

The instrument connector (50) generally comprises a housing (51) and a cover plate (61) mounted thereto. An instrument cable (52) is operatively connected between the instrument connector (50) and the instrument body (94) for transmitting electrical signals between the connector (50) and the instrument body (94). Once again, cable (52) can include any number of electrical conductors (e.g., wires) therein, in some instances corresponding to the number of communication channels established when the contacts on the interface adapter (12) conductively contact the corresponding conductive contacts on the instrument connector (50). For example, in the embodiment shown, cable (52) has nine independent conductors (wires) inside an outer sheath—one conductor for each communication channel provided by the MSIS (10). In other embodiments, the number of mating contacts on a component (12 or 50) and/or the number of communication channels between the two components (12, 50) is greater than the number of electrical conductors of the cable (52) (e.g., when a particular instrument does not require use of the full complement of communication channels).

In the embodiment of FIGS. 1-8, the cables (14, 52) are non-detachably coupled to their respective component. Also in this particular embodiment, cable (52) is non-detachably coupled to the instrument body (94)—in this instance, internally within the instrument body (94). For instruments wherein the instrument shaft is rotatable with respect to the instrument body, the proximal end of the cable (52) can be mounted so as to rotate with the instrument shaft while still maintaining electrical connectivity. As best seen in FIGS. 4 and 5, the distal end of cable (52) is coupled to the instrument connector (50) through the proximal face (54) of housing (51), and cable (14) is coupled to the interface adapter (12) through the sidewall of housing (13).

As an alternative to non-detachably coupling the cables, one or both of the cables (14, 52) can be detachably connected to their respective interface adapter (12) and instrument connector (50)/instrument body (94), such as by using suitable male and female electrical couplings (e.g., RJ-type connectors, D-sub connectors, Amphenol® brand connectors, Molex® brand connectors, and other electrical coupling systems known to those skilled in the art or hereafter developed). This can be desirable, for example, to allow cable (14) to be detached from the interface adapter (12) when it is not needed for providing electrical communication to a surgical instrument. A detachable coupling of cable (52) to instrument body (94) can be advantageous, for example, in that it allows one instrument connector (50) to be employed with multiple instruments and/or removed from the instrument when it is not needed.

Each of interface adapter (12) and instrument connector (50) are annular in shape, having central apertures (19, 57) extending therethrough. These apertures (19, 57) are sized and configured to slidably and rotatably receive instrument shaft (92) therethrough. Upon mating engagement of interface adapter (12) and instrument connector (50) their respective central apertures (19, 57) are axially aligned with each other and with the cannula of the trocar on which the interface adapter (12) is mounted or provided. For example, the central apertures (19, 57) can be sized to have a diameter equal to or slightly greater than the inner diameter of the cannula (87) of the trocar with which the system is to be used. In some embodiments, the diameter of the central aperture (19) of the signal interface adapter (12) is slightly larger than the diameter of the central aperture (57) of the instrument connector (50) as well as the internal diameter of the trocar cannula. By way of example only, the central apertures (19, 57) can have a diameter of about 3 to about 100 mm. In one particular embodiment, the central apertures (19, 57) can have a diameter of about 13 mm (e.g., 12.7 mm), approximately the same as the inner diameter of a "10 mm" trocar (wherein the "10 mm" refers to the size of the instrument received within the trocar cannula). Such sizing allows the MSIS to be used with both "5 mm" and "10 mm" trocars—the most commonly used trocar sizes. In some embodiments the central aperture (19) of the signal interface adapter (12) is about 1 to 5 mm larger than the diameter of the central aperture (57) of the instrument connector (50) and the internal diameter of the trocar cannula.

In the embodiment of FIGS. 1-8, interface adapter (12) is non-removably affixed to the proximal end of the trocar cannula housing (86) (i.e., it is an integral part of the trocar cannula housing). In the alternative embodiment of FIGS. 9-27, the signal interface adapter is removably attachable to the trocar, such as by a spring clip arrangement configured to matingly engage with features on the trocar cannula housing. It will be understood that the shape of signal interface adapter (12) and instrument connector (50) shown in FIGS. 1-8 is merely exemplary. It will also be understood that the term "annular," as used herein, includes not only structures having a circular central aperture and corresponding circular outer perimeter concentric with the central aperture, but also various other outer perimeter shapes such as oval, square, rectangular, polygonal, etc. In some embodiments, the outer perimeter shapes of signal interface adapter (12) and instrument connector (50) can be similar to that of the trocar cannula housing, particularly the shape of the proximal end of the trocar cannula housing.

As also seen in FIGS. 4 and 5, a pair of opposite polarity magnetic regions, e.g., from magnets (20N, 20S), are provided on signal interface adapter (12) adjacent the proximal face (18) thereof. Similarly, a pair of opposite polarity magnetic regions, e.g., from magnets (58N, 58S), are provided on instrument connector (50) adjacent the distal face (56) thereof. Although the opposite polarity magnetic regions can be arranged at any of a variety of circumferentially spaced-apart locations on the interface adapter (12) and instrument connector (50), in the embodiment shown the magnets of each component (12, 50) of the interface system are located 180 degrees apart (i.e., on opposite sides of the central aperture), with the orientation of their polarities reversed. Such an arrangement maximizes magnetically induced rotational torque on the instrument connector (50) during mating engagement of the two components (12, 50). Although a single magnet can be used on each component (12, 50), with the magnets arranged to provide magnetic fields of opposite polarity, the use of two magnets arranged to provide magnetic fields of opposite polarity adjacent the mating face of each component not only increases the magnetic forces that pull the components into alignment, but also helps to ensure that the instrument connector (50) cannot be advanced towards the interface adapter (12) in such a way that the magnetic forces are unable to pull the components (12, 50) into proper, mating engagement. In addition, although more than two magnetic regions can be used on each of the components (12, 50), at least one magnetic region on each component should have a polarity opposite to other magnetic regions on that component. Also, when the MSIS (10) is designed such that there is but one proper rotational alignment of the interface adapter (12) and the instrument connector (50), and more than two magnetic regions are provided on each component (12, 50), the magnetic regions are arranged so as to allow only one rotational orientation of magnetically coupled mating engagement of the components.

As best seen in FIGS. 4 and 5, and the isolated views of FIGS. 6A-B and 7A-B, the proximal face (18) of the signal interface adapter (12) and the distal face (56) of the instrument connector (50) each include a plurality of conductive contacts arranged such that, when the components (12, 50) are in mating engagement (FIG. 2), a predetermined one or more of the contacts on one component will be in contacting relationship with a predetermined one or more of the contacts on the other component. Any of a variety of types of conductive contacts can be used, in any of a variety of arrangements, and those shown and described herein are merely exemplary.

Each mating face (18, 56) of the two components (12, 50) includes an annular conductive ring (22, 60) having an outer perimeter generally corresponding to that of its respective component (12, 50) and a central aperture (25, 63) generally corresponding to the central aperture (19, 57) of its respective component (12, 50). In the example shown in FIGS. 1-8, conductive rings (22, 60) generally have the same configuration except that the conductive ring (22) of the signal interface adapter (12) includes an additional set of apertures through which contacts (e.g., in the form of pogo pins (26C)) extend. It will be understood that the conductive rings (22, 60) can have a variety of other configurations, such as conductive rings that have an outer perimeter that is smaller than the outer perimeter of the components (12, 50) (e.g., as in the alternative embodiment of FIGS. 9-27).

Figure 6A:
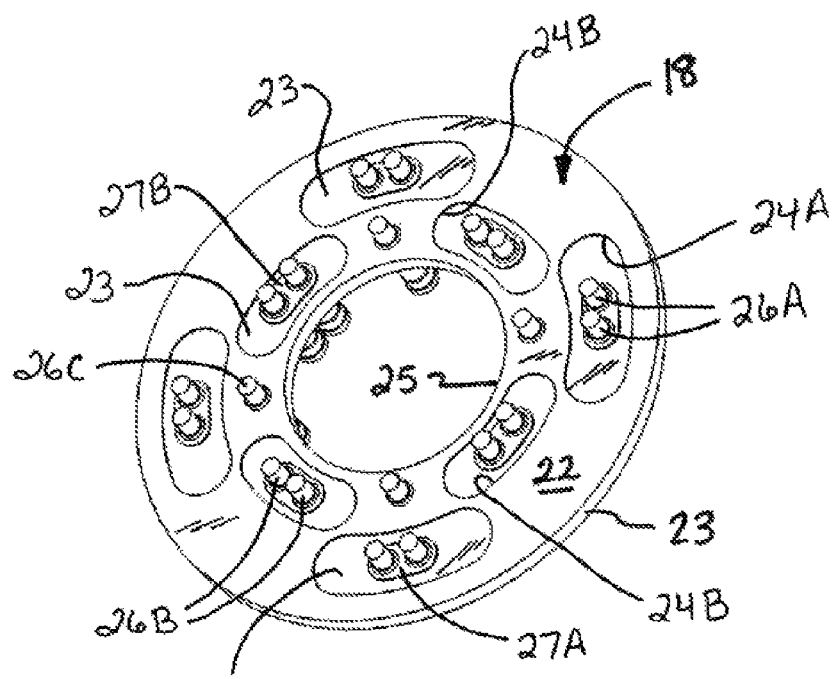
FIG. 6A is a perspective view of the proximal side of the signal interface adapter of the system of FIG. 4, with the housing removed.
Figure 6B:
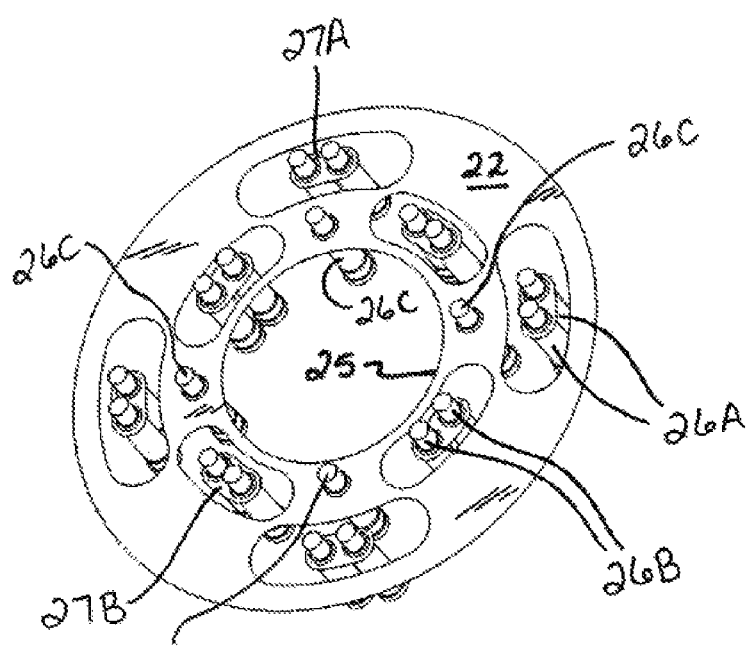
FIG. 6B is the same view with the cover plate removed.
Figure 7A:
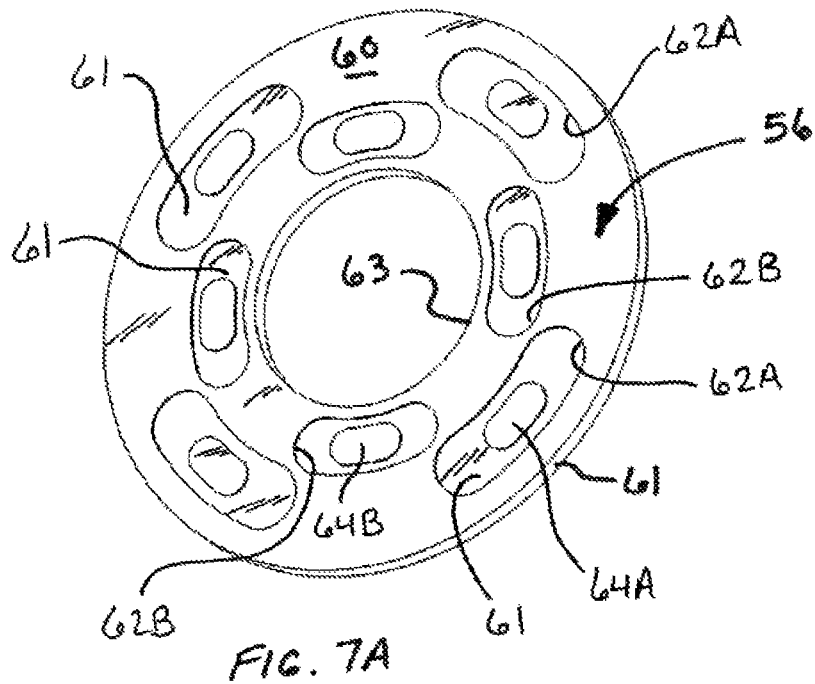
FIG. 7A is a perspective view of the distal side of the instrument connector of the system of FIG. 4, with the housing removed.
Figure 7B:
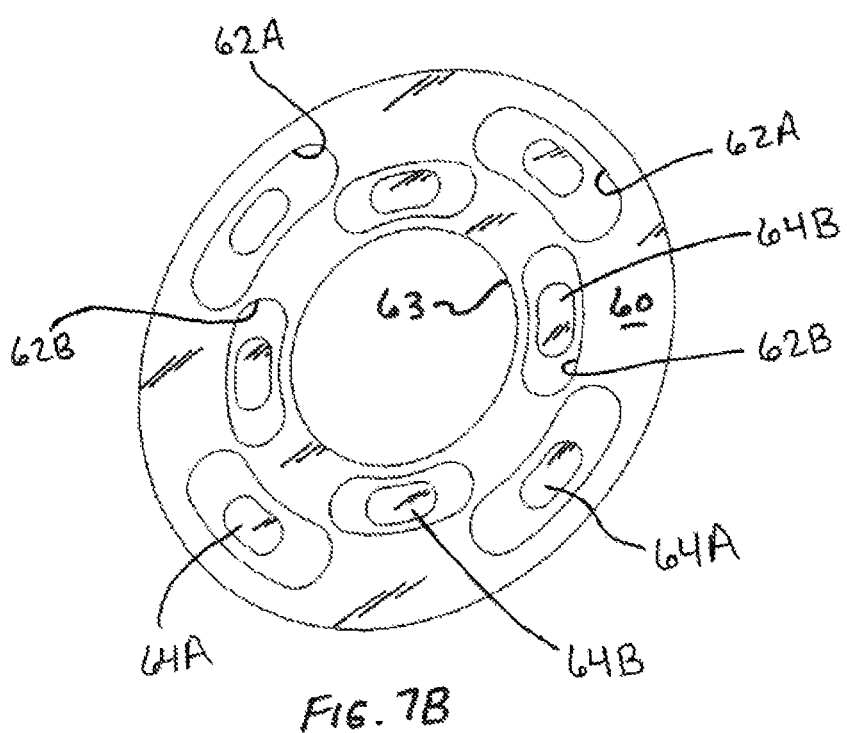
FIG. 7B is the same view with the cover plate removed.

Each conductive ring (22, 60) is mounted on an insulating, annular cover plate (23, 61), wherein the cover plate is absent in FIGS. 6B and 7B. Each conductive ring (22, 60) includes a plurality of circumferentially arranged and spaced-apart curved oval apertures (24A, 24B, 62A, 62B), arranged in a pair of concentric, spaced-apart bands. Thus, conductive ring (22) of signal interface adapter (12) has an outer band of spaced-apart curved oval apertures (24A), and an inner band of spaced-apart curved oval apertures (24B), arranged about a central aperture (25). Similarly, conductive ring (60) of instrument connector (50) has an outer band of spaced-apart curved oval apertures (62A), and an inner band of spaced-apart curved oval apertures (62B), arranged about a central aperture (63). Conductive oval islands (27A, 27B, 64A, 64B) are located within the curved oval apertures (24A, 24B, 62A, 62B), electrically isolated from the rest of the conductive ring (22, 60). Thus, the conductive oval islands (27A, 27B, 64A, 64B) are smaller than the curved oval apertures (24A, 24B, 62A, 62B) in which they are located. Each of the conductive oval islands (64A, 64B) of the instrument connector (50) provides a conductive contact that, when the components (12, 50) are in mating engagement, will be in conductive engagement (i.e., conductive contact) with a predetermined pair of pogo pins on the interface adapter (12). In other words, each of the eight oval islands (64A, 64B) provides an electrical contact. As further explained below, the conductive ring (60) provides a ninth electrical contact on the instrument connector (50).

The conductive rings (22, 60), also referred to as guard rings, surround all of the conductive oval islands (27A, 27B, 64A, 64B). Thus, any stray electrical current from one of the oval islands would first have to cross the guard ring (22, 60) in order to create an electrocution hazard for the patient or the medical practitioner. However, when the components (12, 50) are in mating engagement, the guard rings (22, 60) are not only in electrical communication with each other, but also with an external electrical device (e.g., a generator) operatively connected to the signal interface adapter (via main cable (14)). Thus, the external electrical device can detect stray electrical current jumping from one of the contacts (27A, 27B, 64A, 64B) to the guard ring (22, 60), and immediately shut down the delivery of current to the signal interface adapter.

A plurality of pogo pins (26A, 26B, 26C) (also known as spring pins or spring-loaded contacts) are mounted on the signal interface adapter (12), as seen in FIGS. 5, 6A and 6B. The pogo pins are mounted such that the spring-biased plunger portions thereof extend away from the proximal face (18) of the interface adapter (12). It will be understood, however, that a single pogo pin can instead be provided within each of the oval apertures, with or without the conductive oval islands (27A, 27B). An additional set of individual pogo pins (26C) is also provided. Each individual polo pin (26C) extends through an aperture in the conductive ring (22), and is also in conductive contact with the conductive ring (22).

Each of the eight pairs of pogo pins (26A, 26B) provides a conductive contact that, when the components (12, 50) are in mating engagement, will be in conductive engagement with a predetermined one of the conductive oval islands (64A, 64B) on the distal face (56) of the instrument connector (50). The non-paired pogo pins (26C) together provide a ninth conductive contact that, when the components (12, 50) are in mating engagement, will be in conductive engagement with portions of the conductive ring (60) of the instrument connector (50) located between the oval apertures (62B) thereof.

Figure 8:
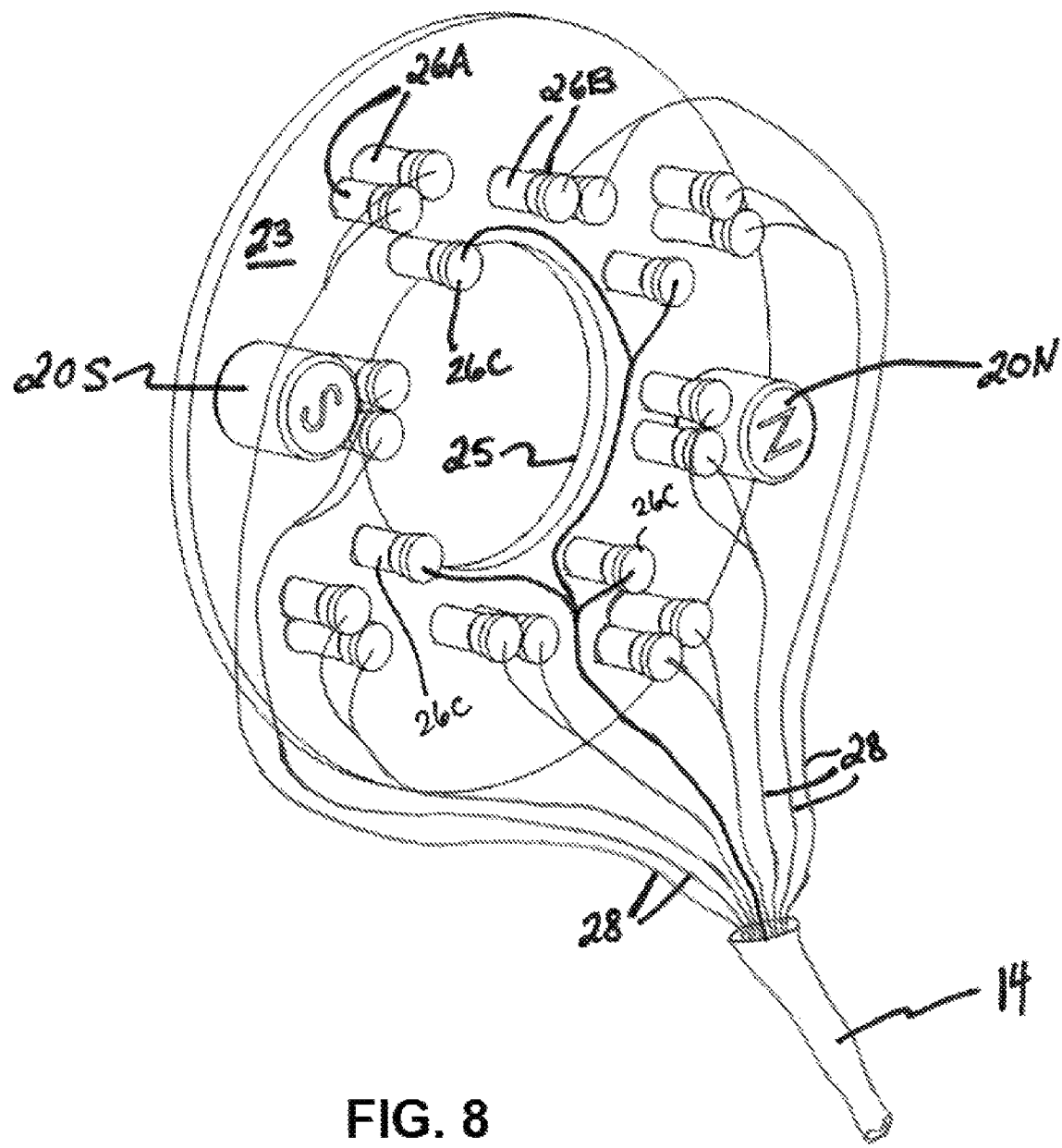
FIG. 8 is a schematic view of the distal side of the signal interface adapter, with the housing removed, showing the electrical connections to the pogo pin contacts and the wire conduits of the cable.

FIG. 8 depicts a schematic illustration of the internal wiring of the signal interface adapter (12), wherein the housing (13) has been removed. The pogo pins (26A, 26B) of each of the eight pairs are in electrical communication with each other as well as an electrical conductor (e.g., a conductive wire) (28) of main cable (14). The four non-paired pogo pins (26C) are also in electrical communication with each other as well as a ninth electrical conductor (28) of the main cable (14). The electrical communication between the pogo pins (26A, 26B, 26C) and the nine electrical conductors (28) of the main cable (14) can be direct (as shown), or indirect via one or more suitable connectors (and, in some instances, other conductive components). For example, a male or female electrical plug or connector can be provided on the housing (13) of the signal interface adapter (12), with each contact of the plug/connector in electrical communication with a pair of the pogo pins (or the individual pins (26C), and a corresponding mating female or male electrical plug/connector provided on an end of the main cable (14) for operative engagement with the plug/connector on the interface adapter (12).

A similar arrangement is provided in the instrument connector (50), with nine electrical conductors (e.g., wires) of the cable (52) in electrical communication with (directly or indirectly) the conductive oval islands (64A, 64B) and the conductive ring (60). One conductor is in electrical communication with each of the conductive islands (64A, 64B) and a ninth conductor is in electrical communication with the conductive ring (60).

The MSIS described herein can be used in a variety of medical, particularly surgical, procedures. A trocar, with or without the signal interface adapter (12) provided thereon, is inserted into a patient in the usual manner, and the obturator removed from the cannula (87). If not already provided on the trocar, the signal interface adapter is attached to the trocar cannula housing (86). Next, a signal-associated surgical instrument such as electrosurgical cutter/stapler (90) having the instrument connector (50) mounted on the shaft thereof is inserted into the trocar.

The instrument shaft (92) is inserted into the cannula through the central aperture (19) of the signal interface adapter (12) (FIG. 1). As the instrument shaft (92) is advanced further into the cannula (87) (FIG. 3), the interface adapter (12) and instrument connector (50) will eventually become sufficiently close so that magnetic forces will pull the instrument connector (50) towards the interface adapter (12), with the instrument connector sliding along the instrument shaft (92). The arrangement of the magnetic regions will also induce torque, causing the instrument connector (50) to rotate about the shaft (92), as necessary, until the instrument connector (50) is in proper rotational alignment with the interface adapter (12) (i.e., with the respective electrical contacts of each component in the desired alignment with the contacts on the other component). The instrument connector (50) will be pulled into engagement with the interface adapter (12) such that each of the conductive islands (64A, 64B) on the distal face of the instrument connector will conductively contact a predetermined pair of the pogo pins (26A, 26B) extending from the proximal face (18) of the interface adapter (12). In addition, the conductive ring (60) will conductively contact the four non-paired pogo pins (26C).

The spring-biased nature of the pogo pins (26A, 26B, 26C) facilitates contact for providing electrical conductivity. Magnetic engagement of the two components (12, 50) causes the plunger portion of each pogo pin to be urged inwardly (i.e., into the housing (13)) until the conductive rings (22, 60) of the two components (12, 50) are in contact with each other. As a result, up to nine communication channels are established between the signal interface adapter (12) and the instrument (90), allowing signals (power and/or communication signals) to be transmitted between one or more devices in communication with main cable (14) (e.g., a generator) and the surgical instrument (90).

In addition to providing one of the communication channels, the conductive rings (22, 60) also provide an additional feature. In order for electrical current to improperly pass from one signal line (i.e., channel) to another signal line (i.e. short out), or to short to the instrument, patient, and/or user, such stray electrical current will first have to travel across one of the conductive rings (22, 60). This feature is a result of the conductive rings (22, 60) surrounding the other electrical contacts (26A, 26B, 64A, 64B) (apart from the non-paired pogo pins (26C) that are functionally part of the contact provided by conductive ring (22)). The ninth communication channel provided by the conductive rings (22, 60), also referred to as the "sense line," can be monitored for any stray current or voltage. If anything is sensed on this sense line, a fault has been detected and power is shut down. Signal line sensing can be done, for example, within the signal interface adapter (12) itself, by the EDS, or by the external device (e.g., a generator).

It will be understood that, although the embodiment of FIGS. 1-8 has been shown and described as having conductive islands on the instrument connector (50) and corresponding pogo pins on the signal interface adapter (12), this configuration can be reversed if desired. In yet another alternative embodiment of the MSIS shown FIGS. 1-8, the conductive rings are omitted from the signal interface adapter and the instrument connector such that the communication channels are provided by the mating contact of discrete, individual contacts when placed in mating, conductive engagement (e.g., the embodiment of FIGS. 39-43).

During mating engagement of the components of the MSIS, the proximal face of the signal interface adapter (12) will often come into contact with the distal face of the instrument connector (50) before the instrument connector (50) has rotated about the instrument shaft into proper alignment. When this occurs, the contacts of the instrument connector can slide across the proximal face of the signal interface adapter as the instrument connector rotates into position. Depending on the amount of rotation necessary for alignment, one or more of the pogo pins (or other form of contacts) may even briefly come into contact with the wrong contacts (64A, 64B) of the instrument connector. In order to prevent such non-mating contact, as well as to facilitate rotational sliding of the instrument connector across the proximal face of the signal interface adapter, the distal face of the instrument connector and/or the proximal face of the signal interface adapter can have various features that facilitate proper rotational alignment and/or prevent contacts on the two components of the MSIS from contacting each other until the two components are in proper alignment. As further described in WO728, such features can comprise, for example, projections on one face the that are received within recesses located on the opposing face when the instrument connector is pulled into mating contact with the interface adapter. In some embodiments, the projections are formed of a non-conductive material (e.g., plastic), and can be in the form of captive ball bearings (e.g., ruby ball bearings) rotatingly mounted in the face of one component that are received in correspondingly shaped recesses in the opposing face of the other component. In the embodiment shown in FIGS. 9-12 of WO728, each projection comprises a wheel rotatingly mounted with respect to the proximal face of the interface adapter, that are received in recesses provided in the distal face of the instrument connector when the components are in mating engagement. It will also be understood that various other forms of projections may be provided on either or both components (12, 50), including non-rotating projections that will nevertheless slide along the opposing face of the other component until received in an appropriately shaped recess when proper alignment is achieved.

FIGS. 9-27 depict yet another alternative embodiment of a MSIS (210) comprising a signal interface adapter (212) and an instrument connector (250). In this embodiment planar, mating contacts are provided on each face of the components (212, 250), similar to those described above with respect to the instrument connector (50) (instead of pogo pins or other pin-type contacts). In addition, the signal interface adapter (212) is configured to be removably mounted on the proximal end of a trocar cannula housing (e.g., trocar cannula housing (86) in FIG. 1).

Figure 9:
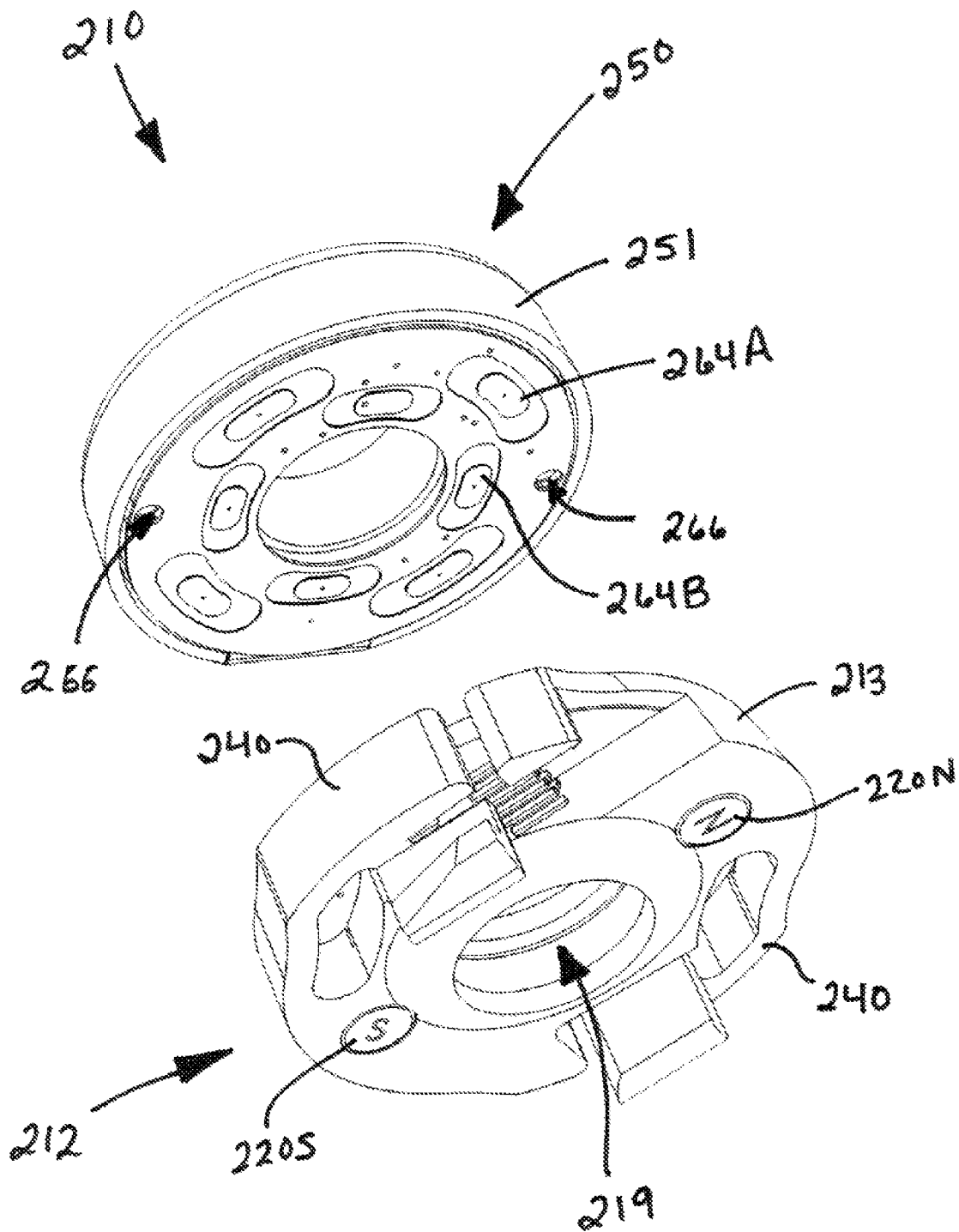
Figure 10:
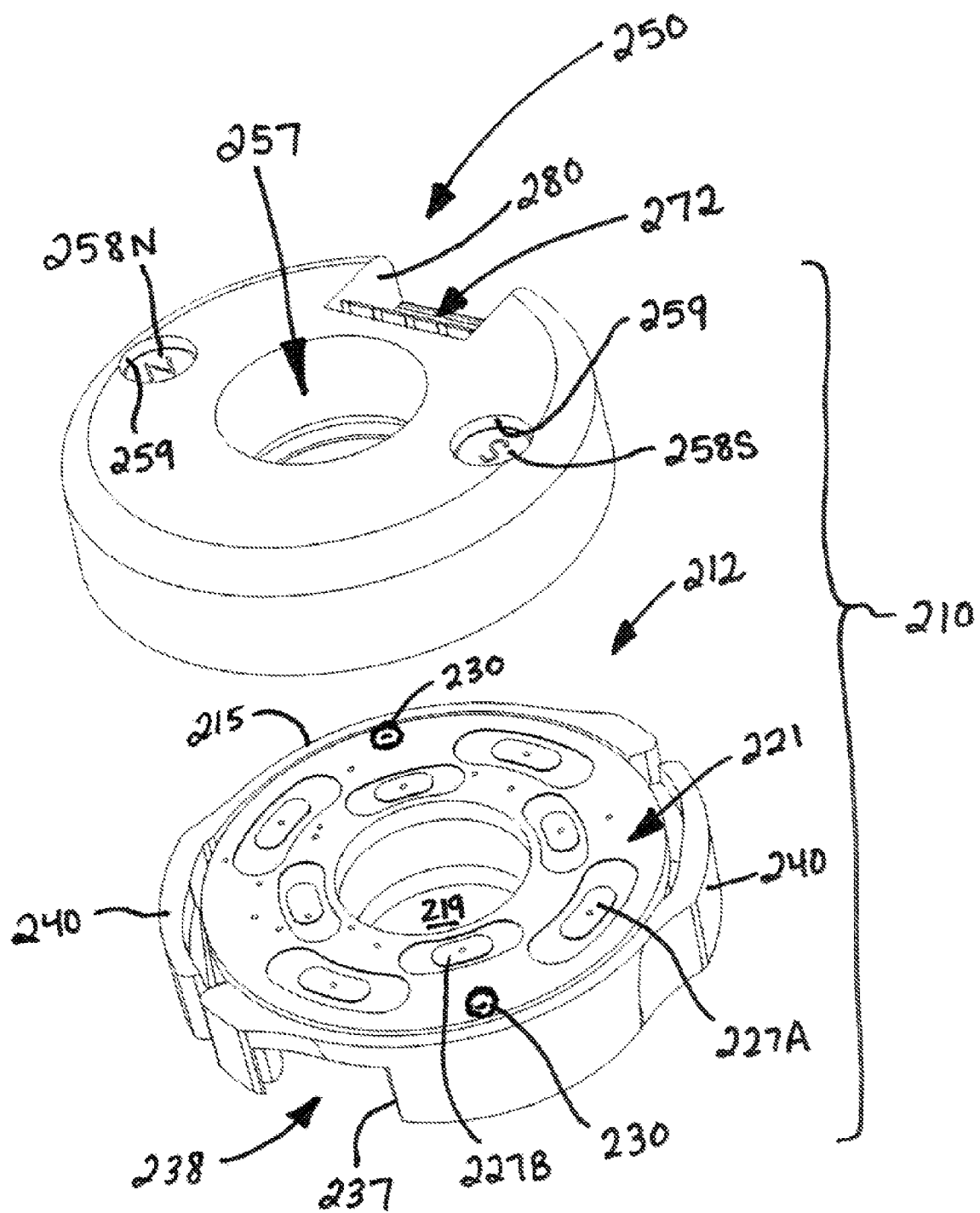
Figure 11:
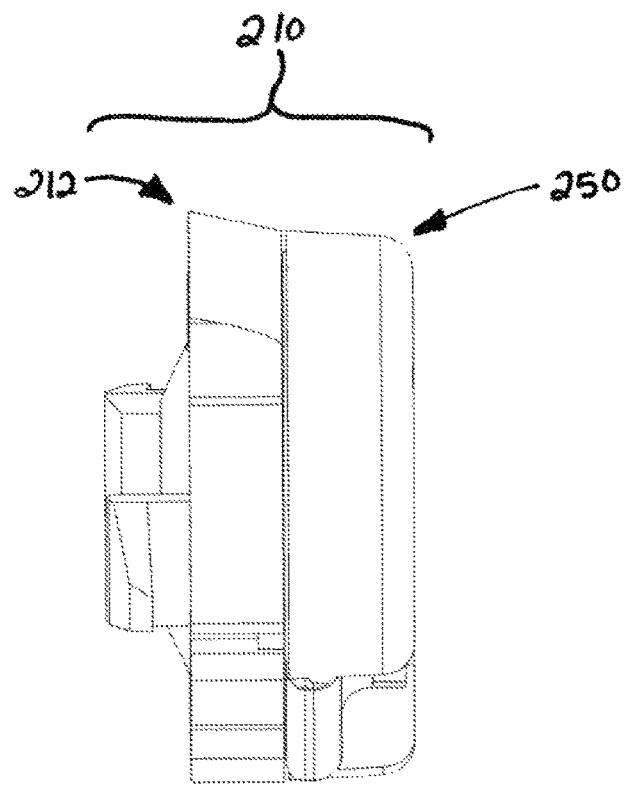
FIG. 11 is a side view of the MSIS of FIG. 9, depicting the signal interface adapter and instrument connector thereof in mating engagement.

FIGS. 9 and 10 are perspective views of MSIS (210), wherein the signal interface adapter (212) and instrument connector (250) are shown disengaged from one another, FIG. 9 depicting the distal sides of the two components and FIG. 10 depicting the proximal sides. FIG. 11 is a side view that depicts the two components (212, 250) in mating engagement. It will be understood that the cables extending from the interface adapter (212) and instrument connector (250) have been omitted in FIGS. 9-27. However, exemplary connectors for these cables are shown, and it will be understood that the cables will have mating connectors at the ends thereof.

Like the previously described embodiments, the signal interface adapter (212) is configured to be mounted on the proximal end of a trocar cannula housing, and the instrument connector (250) is configured to be slidingly mounted on the shaft of a surgical instrument. Each component is annular in shape, having central apertures (219, 257) extending therethrough. When the two components (212, 250) are in mating engagement with one another (FIG. 15), the apertures (219, 257) are axially aligned with one another. The apertures are sized and configured to slidably and rotatably receive an instrument shaft therethrough. As before, the depicted shapes of these two components of the MSIS are merely exemplary.

The signal interface adapter (212) generally comprises a housing (213) and a cover plate (221) mounted thereto. In this embodiment, cover plate (221) is in the form of a PCB having a patterned, conductive ring (222) on the proximal side of a substrate (223). PCB cover plate (221) is multi-layered, with plated through-holes (or vias) (234) connecting portions of the conductive ring (222) to underlying layers that include various electrical traces (not shown).

The proximal side of housing (213) is generally cup-shaped, having an outer rim (215) with an inner diameter slightly larger than the outer diameter of PCB cover plate (221). PCB cover plate (221) is received in the proximal side of housing (213), on proximal surface (217) of housing (213), within rim (215) (see FIG. 15). PCB cover plate (221) can be secured in place by an adhesive, mechanical fasteners such as screws or rivets, and/or press fitting.

As in the previously described embodiments, a pair of opposite polarity magnets (220N, 220S) are provided on signal interface adapter (212), and a pair of opposite polarity magnets (258N, 258S) are provided on instrument connector (250). Once again the opposite polarity magnets of each component (212, 250) of the interface system are located 180 degrees apart (i.e., on opposite sides of the central apertures (219, 257)). A pair of cylindrical bores (233) extend through the thickness of housing (213) between proximal end surface (217) and distal end surface (229) (see FIGS. 17 and 18), and receive magnets (220N, 220S) therein. The magnets can be held in place by an adhesive, mechanical fasteners, and/or press fitting. On the instrument connector, magnets (258N, 258S) are received in cylindrical cavities (259) that are open at the proximal face (254), and held in place by an adhesive, mechanical fasteners, and/or press fitting (see FIG. 10).

Figure 15:
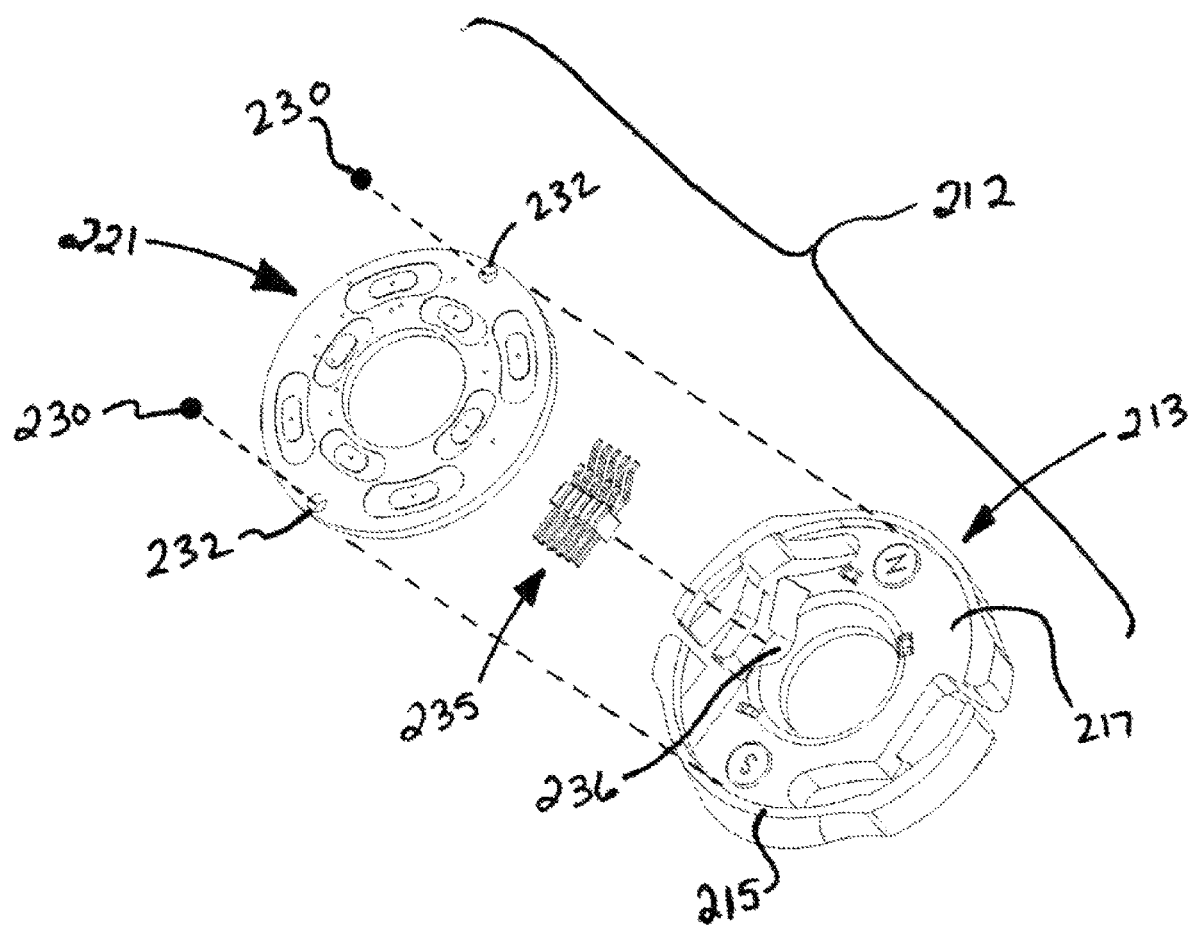
FIGS. 15 and 16 are exploded views of the signal interface adapter of FIG. 12, viewed from the proximal and distal sides, respectively.
Figure 16:
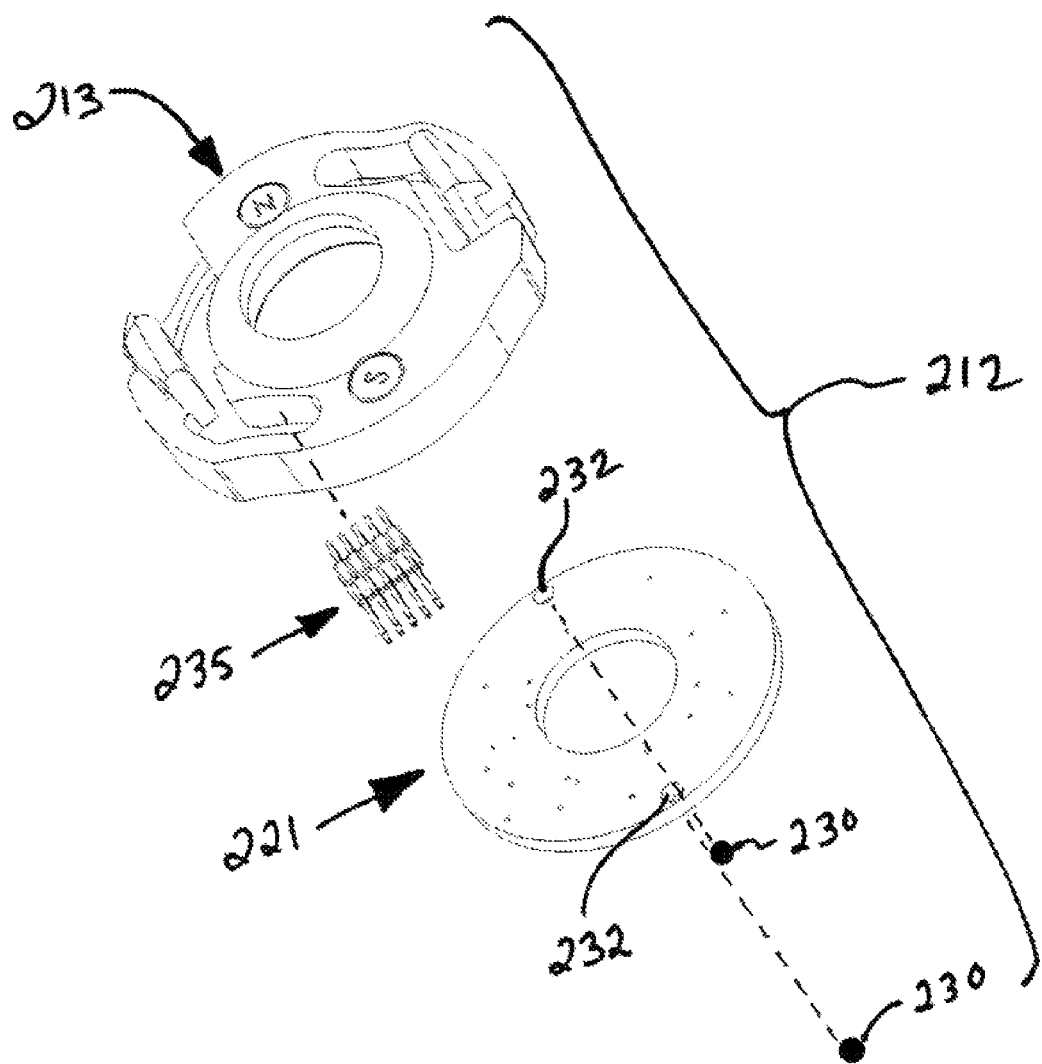
Figure 17:
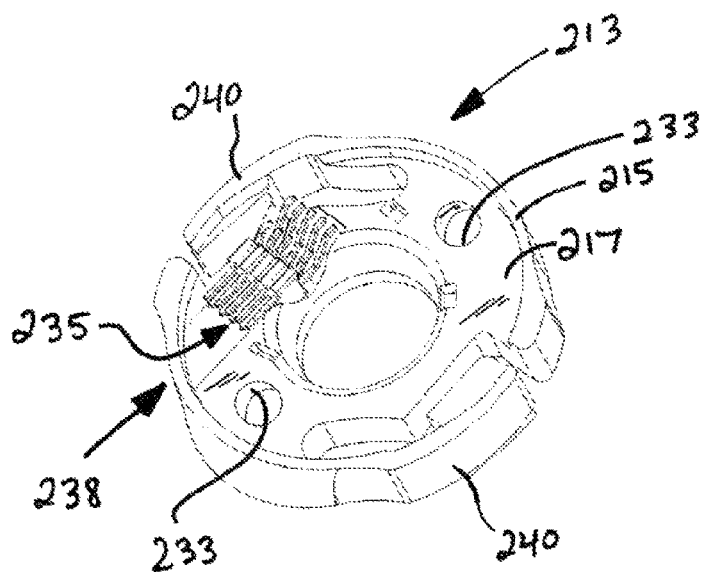
FIG. 17 is a perspective view of the signal interface adapter housing of FIG. 9.
Figure 18:
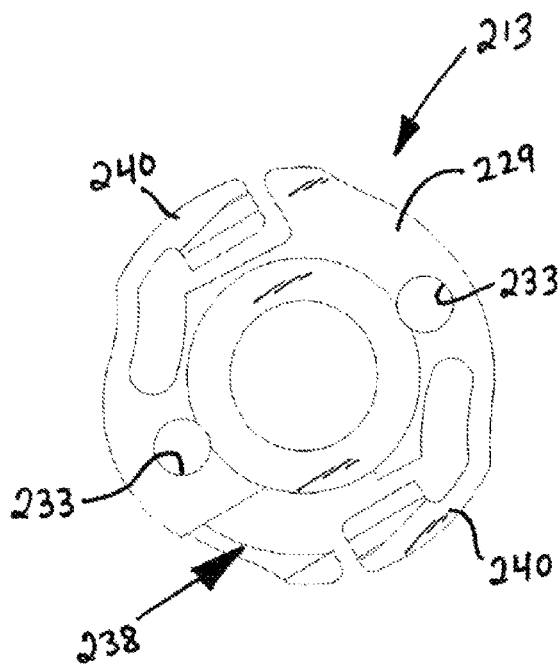
FIG. 18 is a bottom (distal) plan view of the signal interface adapter of FIG. 9.
Figure 19:
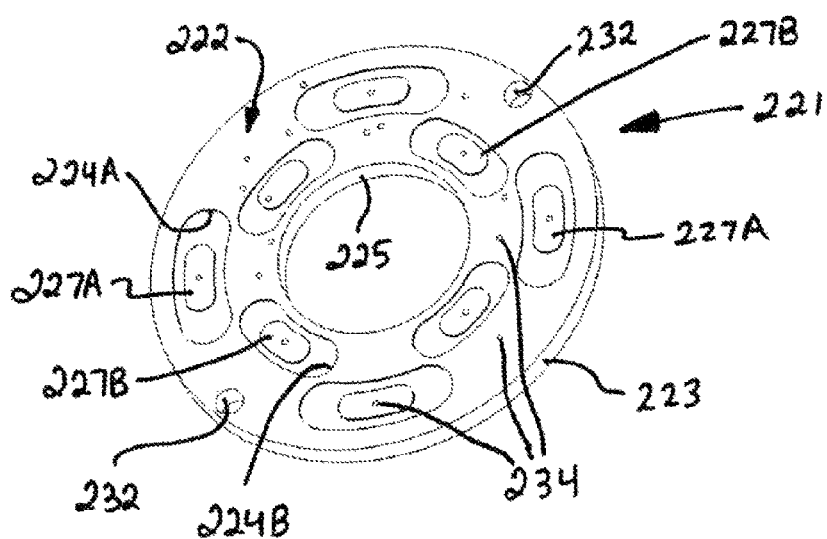
FIG. 19 depicts a perspective view of the proximal side of the PCB cover plate of the signal interface adapter of FIG. 9.
Figure 20:
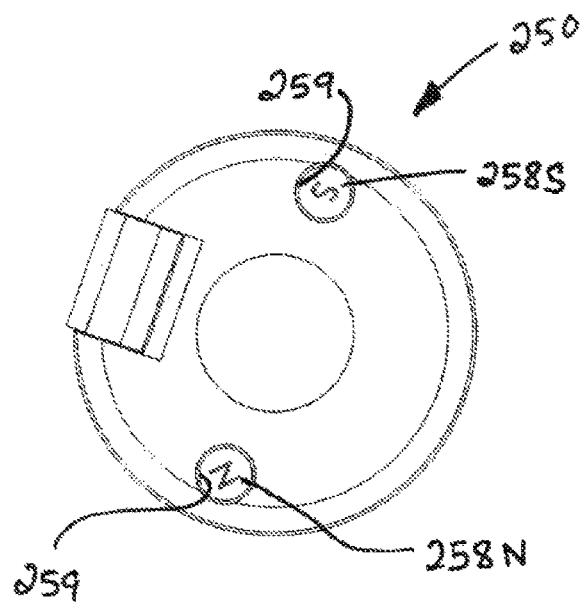
FIGS. 20 and 21 depict upper (proximal) and bottom (distal) plan views, respectively, of the instrument connector of the system of FIG. 9.
Figure 21:
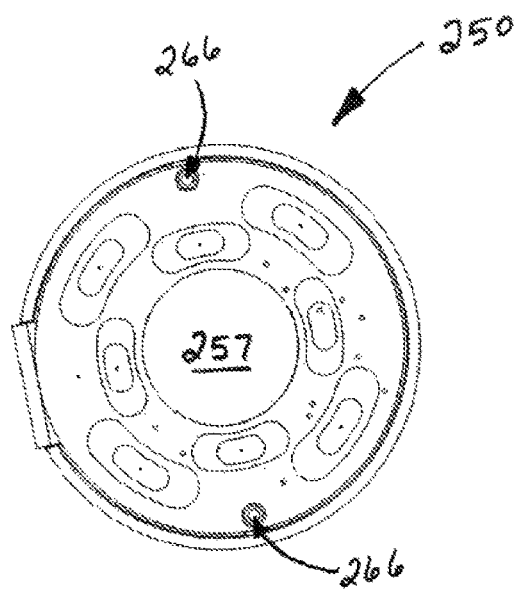
Figure 22:
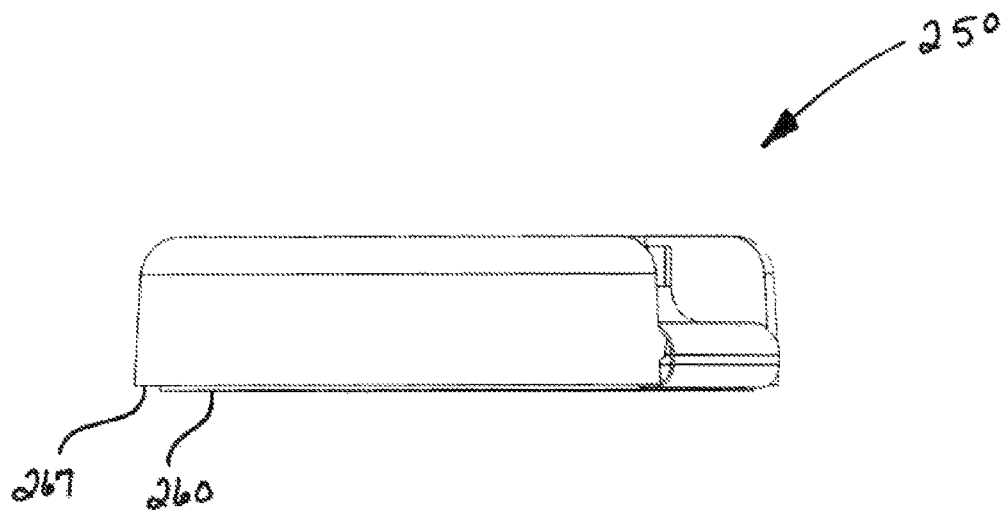
FIG. 22 depicts a side view of the instrument connector of FIG. 20.

A 10-pin electrical connector (235) is received in a recess (236) provided in proximal end surface (217) of housing (213) of the interface adapter (212), beneath the PCB cover plate (221), as best seen in FIGS. 15 and 17. The pins of connector (235) are in electrical communication with the various contacts of the interface adapter (212) using conductive traces and the like (not shown). A rectangular cutout (237) (see FIG. 10) is provided in the sidewall of the housing (213), thus providing a passageway (238) through which a female connector on a cable (not shown) can be operatively attached to the connector (235) in order to provide electrical communication to the external device (similar to main cable (14) described previously).

Figure 12:
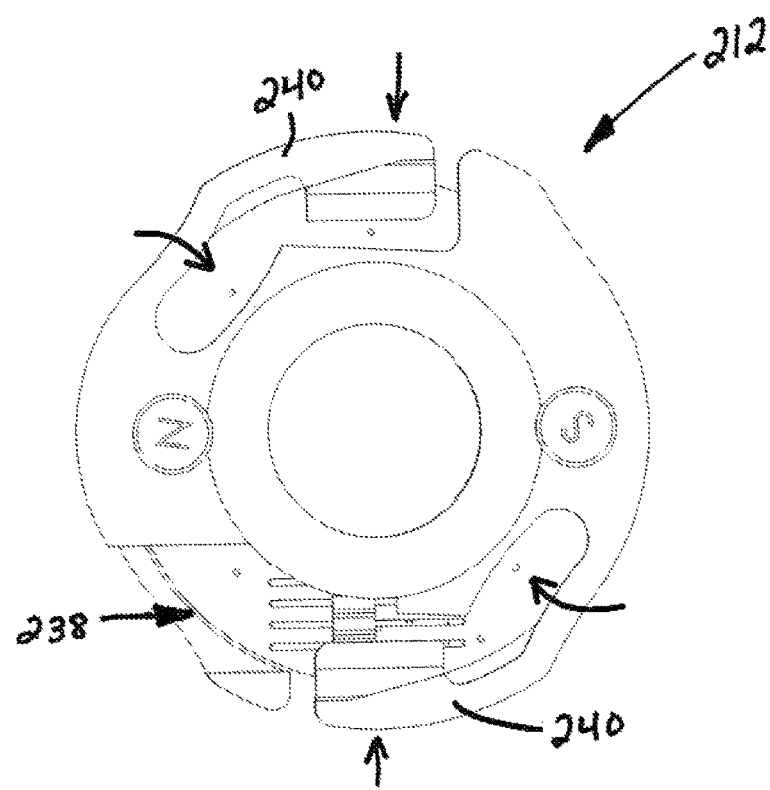
FIG. 12 is a bottom (or distal) end view of the signal interface adapter of the system of FIG. 9.
Figure 13:
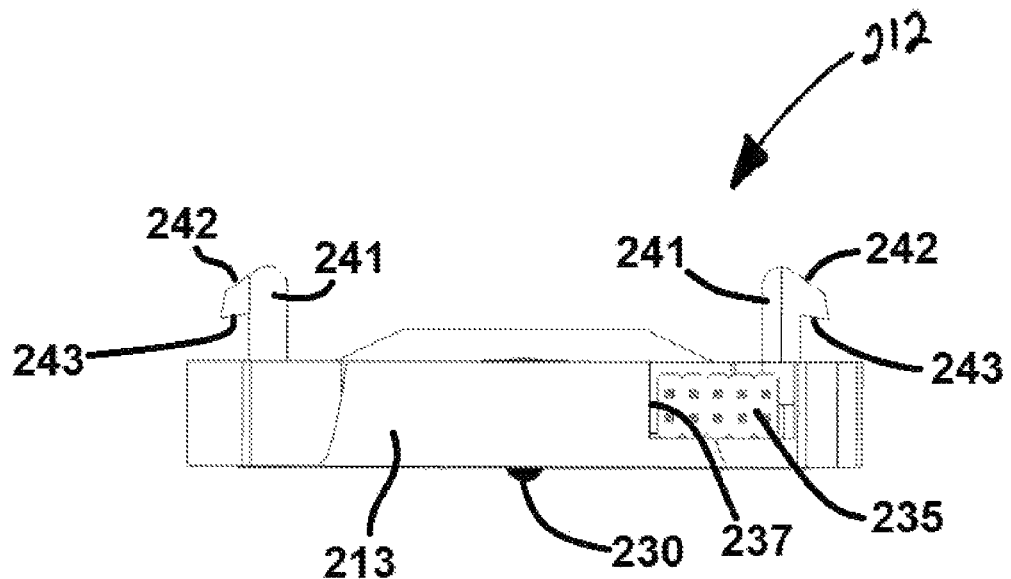
FIGS. 13 and 14 are side views of the signal interface adapter of FIG. 12, rotated 90 degrees from each other.

On its distal side, the interface adapter (212) is configured to be removably mounted on the proximal end of a trocar cannula housing (e.g., trocar cannula housing (86) in FIG. 1). In particular, a pair of spring-like cantilevered arms (240) is provided on opposite sides of the housing (213). Cantilevered arms (240) can be flexed radially inward, as shown in FIG. 12. Such resilient flexing is enhanced by forming the housing (213) of a suitable resilient material, such as molded plastic. A distally extending latch arm (241) is provided at the free end of each cantilevered arm (240), and terminates in radially extending clip (242) having a shoulder (243). The clips (242) are located and configured to be lockingly received by correspondingly shaped slots on the proximal end of a trocar cannula housing such that the shoulders (243) can be locked beneath a bottom edge of the slot.

For example, in the embodiment shown clips (242) are configured for locking engagement with slots on the first housing member of the trocar housing shown and described in U.S. Patent Pub. No. 2005/0070947 ("the '947 App.", published on Mar. 31, 2005, and incorporated by reference herein.

In particular, clips (242) cooperate with the first housing member (36 in the '947 App.) in the same manner as the "mating latches 164, 166" are received in the slots on the upper surface of the first housing member (see FIG. 2 of the '947 App.). After the cannula has been inserted into the patient, the obturator assembly is detached from the trocar housing, and the interface adapter (212) shown and described herein is attached to the trocar cannula housing in its place. The clips (242) are inserted into the slots on the trocar cannula housing. The sloped distal surface of the clips (242) will be urged against the sides of the slots, causing the cantilevered arms (240) to flex radially inward. The clips (242) proceed down the slots until their shoulders (243) extend past the base of the slots, resulting in the clips (242) snapping radially outward thus securing the interface adapter (212) to the trocar cannula housing. In order to remove the interface adapter from the trocar housing, the cantilevered arms (240) are pressed radially inward until the shoulders (243) clear the sidewalls at the base of the slots on the cannula housing, allowing the interface adapter to be removed. It will be understood, of course, that the interface adapter (212) can be configured in a variety of other ways to allow for removable mounting to trocar cannula housings of various configurations, whether now known or hereafter developed.

Cover plate (221), comprising a PCB having a patterned, conductive ring (222) on the proximal side of the insulating substrate (223), includes a plurality of conductive contacts. Conductive ring (222) is generally annular in shape, having a central aperture (225) corresponding to the central aperture (219) of the interface adapter (212). While the conductive ring (222) itself provides one contact for mating engagement with a corresponding conductive ring (260) and/or another contact on the instrument connector (250), the PCB cover plate (221) further includes a plurality of circumferentially arranged and spaced-apart contacts in the form of conductive oval islands (227A, 227B) arranged in a pair of concentric, spaced-apart bands, similar to the previous embodiments. Thus, the PCB cover plate (221) further includes an outer band of spaced-apart contacts (227A), and an inner band of spaced-apart contacts (227B), arranged about a central aperture (225). The conductive oval islands, i.e., the contacts (227A, 27B) are once again located within curved oval apertures (224A, 224B) provided in the conductive ring (222), such that the contacts (227A, 227B) are electrically isolated from the conductive ring (222) that surrounds each of the contacts (227A, 227B).

The interface adapter (212) includes a pair of projections (230) that are received in corresponding recesses (266) on the instrument connector (250) when the two components (212, 250) are in mating engagement with one another. The projections (230) comprise captive ball bearings (e.g., non-conductive ruby ball bearings) that not only prevent non-mating electrical contact prior to proper alignment of the components (212, 250), but also facilitate rotational sliding of the instrument connector and the signal interface adapter. The bearings (230) are captively mounted in apertures (232) provided in PCB cover plate (221), such that the bearings (230) can rotate therein. Alternatively, the bearings can be non-rotatably mounted in the proximal face (218) of the interface adapter (212) or the distal face (256) of the instrument connector (250).

Portions of the bearings (230) extend above the conductive ring (222) and islands (227A, 227B), thereby preventing the conductive ring (222) and islands (227A, 227B) from contacting any portion of the instrument connector (250) until the instrument connector is in proper rotational alignment with the signal interface adapter (212). When proper rotational alignment is achieved, the bearings (230) are received within the recesses (266) on the instrument connector (250), and the instrument connector is pulled into mating contact with the interface adapter. It will be understood, of course, that the bearings (230) (or other projections) can be provided on the instrument connector rather than on (or in addition to) the interface adapter along with corresponding recesses on the interface adapter. In addition, while recesses (266) are in the form of cavities provided by apertures (271) in the cover plate (261) of the instrument connector and other underlying features, as described below, the recesses can be configured in a variety of other ways depending, in part, on the nature of the projections on the interface adapter (212).

Turning to the instrument connector (250) component of the modular interface system (212), this component is configured similar to the interface adapter (212). However, instead of a rigid PCB, instrument connector (250) employs a flexible printed circuit board ("FPCB") for providing the mating contacts. The FPCB allows for the contacts to protrude outwardly and resiliently from the distal face of the instrument connector (250) in order to facilitate mating communication with the contacts on the interface adapter (212). Thus, the contacts provided by the FPCB replace the spring-loaded pogo pins of the embodiment of FIGS. 1-8. In addition, an elastomeric sheet located between the FPCB and the instrument connector housing (251) provides support beneath each of the contacts, urging the contacts outwardly in order to facilitate mating contact. It will be understood that both the interface adapter (212) and the instrument connector (250) can employ a FPCB to provide resiliently biased contacts in the manner described below. As yet another alternative, the instrument connector can employ a rigid PCB while the interface adapter employs a FPCB so as to provide resiliently biased contacts in the manner described below.

The instrument connector (250) generally comprises a housing (251) and a FPCB cover plate (261) mounted thereto. FPCB cover plate (261) has a patterned, conductive ring (260) on the proximal side of a flexible, insulating substrate. FPCB (261) is multi-layered, with plated through-holes (or vias) to connect portions of the conductive ring (260) to underlying layers that include various electrical traces (not shown).

Figure 25:
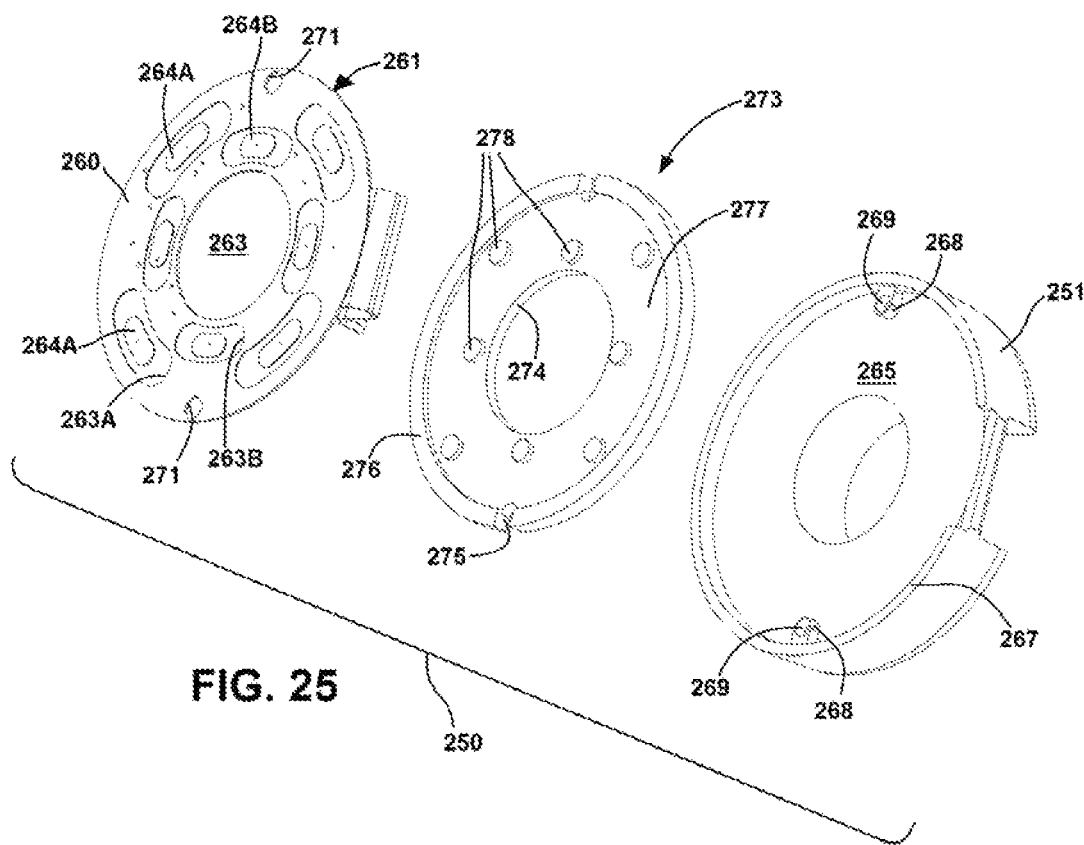
FIGS. 25 and 26 are exploded views of the instrument connector of FIG. 20, viewed from the distal and proximal sides, respectively.
Figure 26:
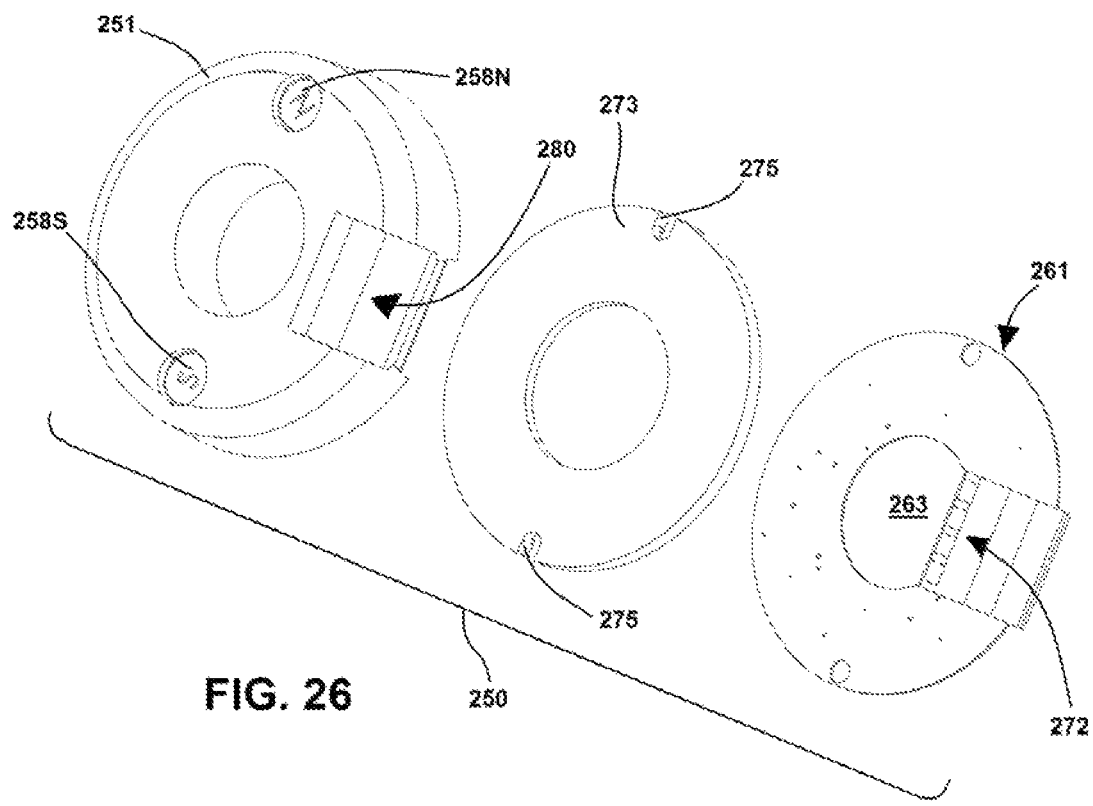

As best seen in FIG. 25, the distal face (265) of the housing (251) is recessed, having an outer rim (267) extending around its perimeter. A pair of arcuate members (268), each having a hemispherical cavity (269) therein, are provided on opposite sides of the distal face (265), extending radially inward from the outer rim (267) as shown. The hemispherical cavities (269) provide the bottom of the recesses (266) for receiving the bearings (230). The members (268) are not as high as the outer rim (267), such that the upper (i.e., distal) surface of each arcuate member (268) does not extend to the upper surface of the outer rim in order to facilitate receiving a portion of one of the bearings (230) in each of the hemispherical cavities (269).

A resilient, elastomeric support member (273) having a central aperture (274) is received on the distal face (265) of the housing (251). The support member (273) includes a pair of cutouts (275) that receive the arcuate members (268) on the distal face (265) of the housing (251) therein. A plurality of contact biasing projections are provided on the support member (273), including a plurality of support nubs (278) that extend away from the distal surface (277) of the support member (273), as well as an outer support rim (276) that extends about the periphery of the support member (273). The support nubs (278) and outer support rim (276) are of approximately the same height with respect to the distal surface (277).

Figure 27:
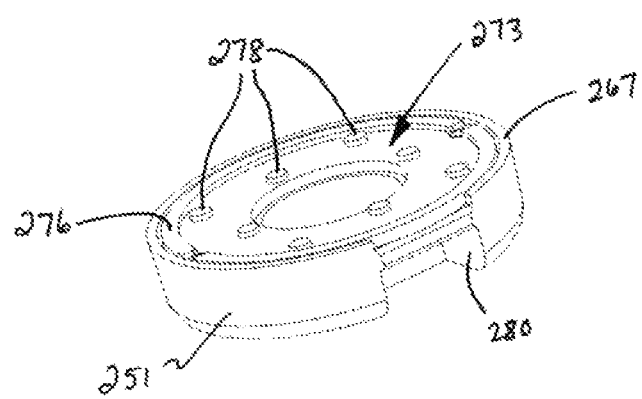
FIG. 27 is a perspective view of the instrument connector of FIG. 20, wherein the FPCB cover plate has been removed.

The support member (273) is received atop the recessed distal face (265) of the housing (251), surrounded by the outer rim (267), with arcuate members (268) positioned within cutouts (275). As best seen in FIG. 27, the support member (273) is configured such that the upper (i.e., distal) surface of the outer support rim (276) and support nubs (278) are generally level with each other and with the upper (distal) surface of the outer rim (267) of the housing (251), and such that there is a small gap between the outer perimeter of support rim (276) and the inner circumference of outer rim (267).

FPCB cover plate (261), comprising a patterned, conductive ring (260) on the distal side of an insulating substrate, includes a plurality of conductive contacts. Conductive ring (260) is generally annular in shape, having a central aperture (263) corresponding to the central aperture (257) of the instrument connector (250). While the conductive ring (260) itself provides one contact for mating engagement with the corresponding ring contact (222) on the signal interface adapter (212), the FPCB cover plate (261) further includes a plurality of circumferentially arranged and spaced-apart contacts in the form of conductive oval islands (264A, 264B) arranged in a pair of concentric, spaced-apart bands. Thus, FPCB cover plate (261) has an outer band of spaced-apart contacts (264A), and an inner band of spaced-apart contacts (264B), arranged about the central aperture (263). The conductive oval islands, i.e., the contacts (264A, 264B) are located within curved oval apertures (263A, 263B) formed in the conductive ring (260), such that the contacts (264A, 264B) are electrically isolated from the rest of the conductive ring (260). FPCB cover plate (261) also includes a pair of apertures (271) located on opposite sides of the cover plate adjacent the outer perimeter, which define the entrance portion of the recesses (266) for receiving the bearings (230).

Figure 23:
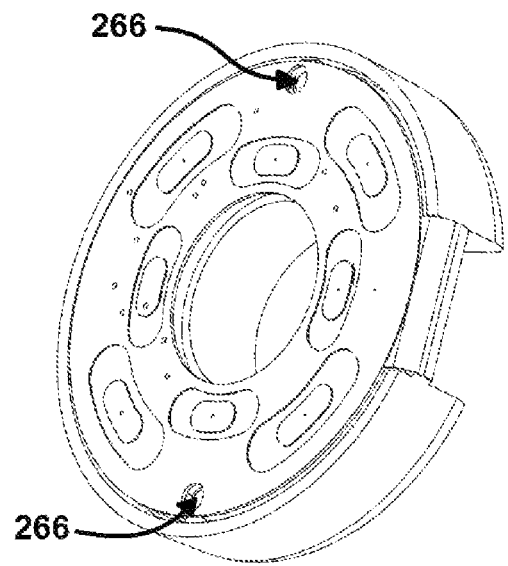
FIGS. 23 and 24 depict perspective views of the distal and proximal sides, respectively, of the instrument connector of FIG. 20.
Figure 24:
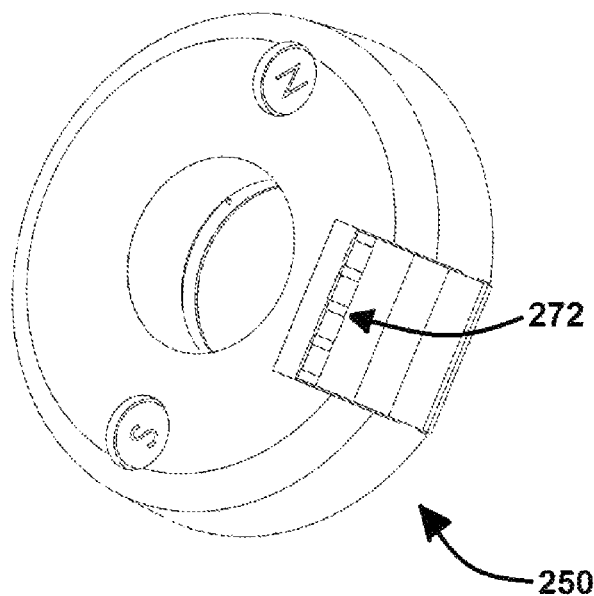

FPCB cover plate (261) is located atop the elastomeric support member (273) such that the recesses (271) are aligned with the cutouts (275) of the support member and the cavities (269) of the housing (251) (as best seen in FIG. 23), thereby providing the recesses (266) for receiving the bearings (230). In addition, the FPCB cover plate (261) is positioned such that one of the support nubs (278) is located beneath each of the contacts (264A, 264B), and the outer perimeter of the cover plate is positioned atop the rim (276) of the support member (273). The nubs (278) and rim (276) of the support member (273) thus resist inward deflection of the contacts (264A, 264B) as well as inward deflection of the outer portion of the conductive ring (260) of the FPCB cover plate (261) supported by the rim (276). Accordingly, the nubs (278) and rim (276) comprise biasing members that serve to resiliently bias the contacts (264A, 264B) and the outer portion of the conductive ring (260) outwardly (i.e., distally, towards the signal interface adapter (212) during use), thereby facilitating mating, conductive engagement of the contacts on the instrument connector (250) with the contacts on the interface adapter (212). Of course other types of biasing members can be used, such as biasing springs or other resilient features located beneath the contacts and conductive ring.

A ribbon connector (272) extends from the FPCB cover plate (261), and its contacts are in electrical communication with the contacts (260, 264A, 264B), via one or more traces or other conductive pathways provided in one or more of the patterned layers of the FPCB cover plate (261). Ribbon connector (272) is wrapped over the outer edge of the instrument connector (250) and is received within the chamber (280) provided on the housing (251) of the instrument connector. A female connector on a cable similar to cable (52) previously described (not shown) can be operatively attached to the ribbon connector (272), with the other end of the cable operatively connected to the instrument (e.g., to the instrument body) in order to provide electrical communication between the instrument connector (250) and the instrument on which it is mounted.

The MSIS (210) of FIGS. 9-27 is used in a manner similar to that described above for the embodiment of FIGS. 1-8. Once the trocar has been positioned in a patient in the usual manner and the components (212, 250) of the MSIS (210) are positioned on the trocar housing and instrument, the instrument shaft is inserted into the cannula through the central aperture (219) of the signal interface adapter (212). As the instrument shaft is advanced further into the trocar cannula, the interface adapter (212) and instrument connector (250) will eventually become sufficiently close so that magnetic forces will pull the instrument connector (250) towards the interface adapter (212) along the instrument shaft. The arrangement of the magnetic regions will also induce torque, causing the instrument connector (250) to rotate (as necessary) about the instrument shaft until proper alignment is achieved with respect to the interface adapter (212). As the instrument connector (250) rotates into proper alignment with the interface adapter under the influence of the magnetic regions, the distal face of the instrument connector (250) will ride atop the bearings (230) of the interface adapter until the bearings drop into the recesses (266) (i.e., into apertures (271) and the underlying cavities (269)) of the housing (251) of the instrument connector. This will also provide an audible click and a tactile indication that mating engagement has been achieved.

Upon such mating engagement, each one of the contacts (264A, 264B) of the instrument connector (250) will be in mating engagement (i.e., contact providing electrical communication) with a corresponding and predetermined one of the contacts (227A, 227B) on the interface adapter. In addition, the conductive ring (260) of the instrument connector will be in mating engagement (i.e., contact providing electrical communication) with the conductive ring (222) on the signal interface adapter.

Figure 28:
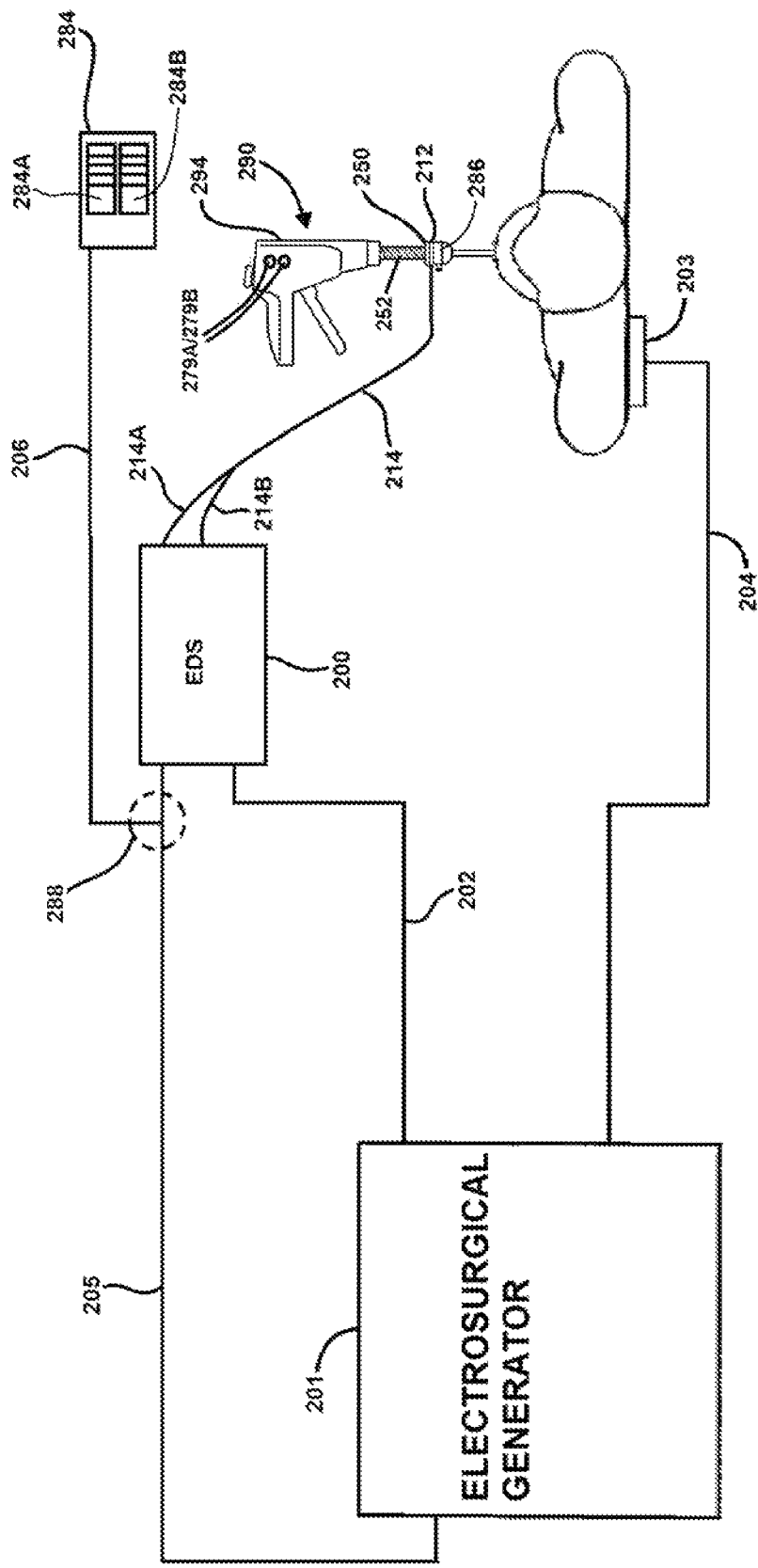
FIG. 28 is a schematic illustration of an electrosurgical system including the MSIS of FIGS. 9-27 along with an engagement detection system ("EDS"), a surgical instrument and an electrosurgical generator.
Figure 35:
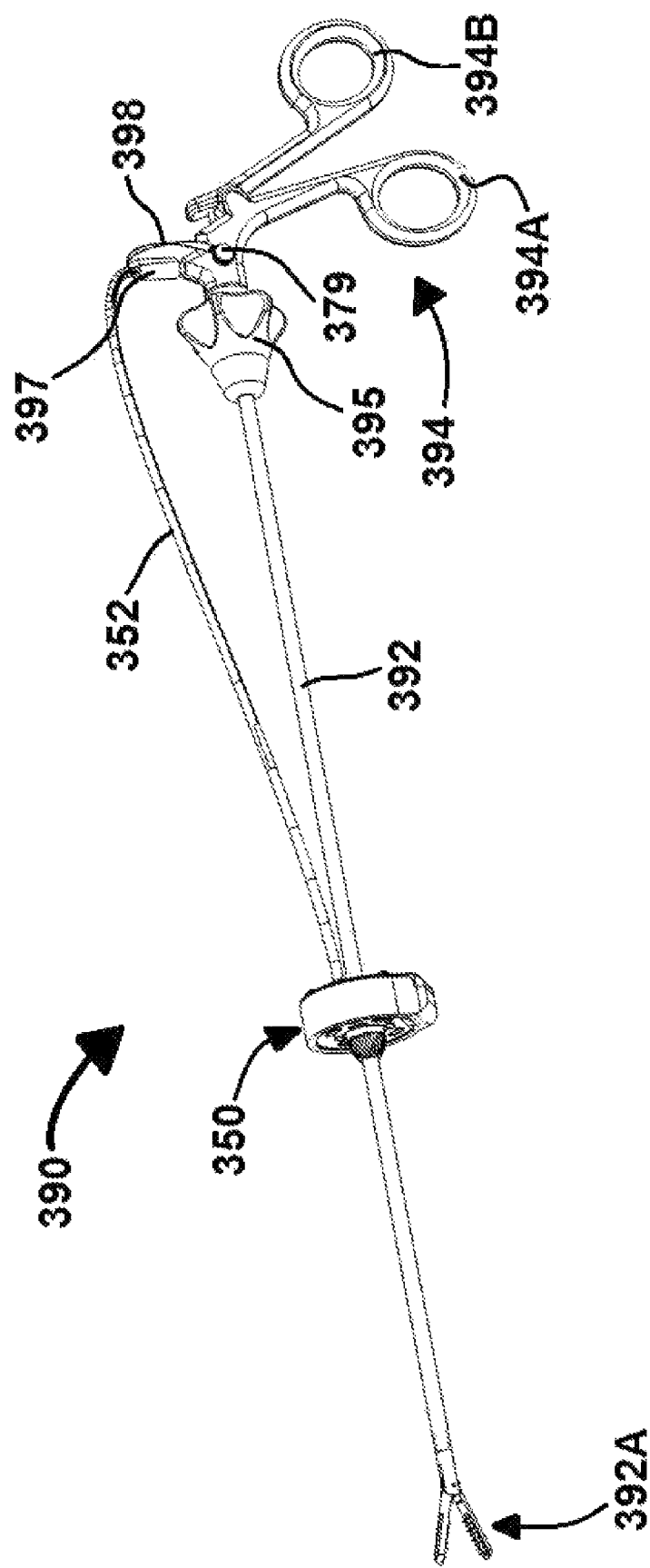
FIG. 35 depicts the surgical instrument and instrument connector of the system of FIG. 34.

FIG. 28 depicts a schematic illustration of one embodiment of a monopolar surgical arrangement employing the MSIS of FIGS. 9-27. In this embodiment only five communication channels between the signal interface adapter (212) and the instrument connector (250) are used (i.e., are active). Rather than having unused communication channels (i.e. unused contacts), the components of the MSIS is optionally modified so as to include five mating contacts on each component (i.e., five communication channels rather than ten). The signal interface adapter (212) is shown mounted on the proximal end of a trocar cannula housing (286) and the instrument connector (250) is slidingly mounted on the elongate shaft of a monopolar surgical instrument (290) (monopolar forceps in the depicted example). The instrument cable (252) is operatively connected between the instrument connector (250) and the instrument body (294) for transmitting electrical signals between the connector (250) and the instrument body. In FIG. 28, instrument cable (252) is shown coiled around the instrument shaft. However, in other embodiments (e.g., as shown in FIG. 35), the instrument cable is not coiled around the instrument shaft.

Figure 29:
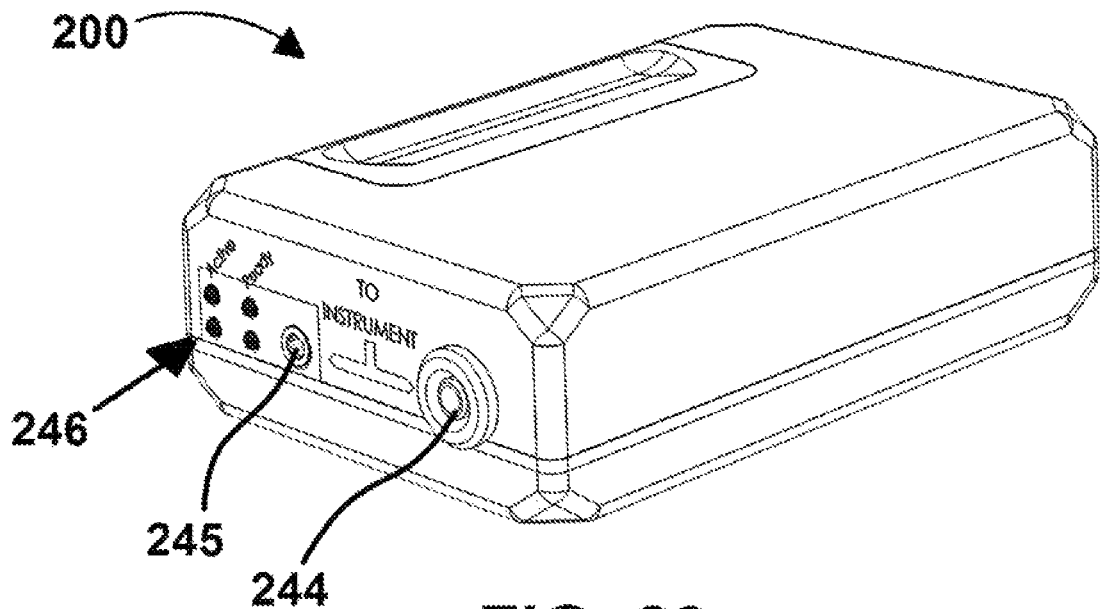
FIGS. 29 and 30 are front and rear perspective views of the EDS used in FIG. 28.

Cable (252) can include any number of independent electrical conductors (e.g., wires) inside an outer sheath, in some instances corresponding to the number of active communication channels established when the contacts on the interface adapter (212) conductively contact the corresponding conductive contacts on the instrument connector (250). In other embodiments, including that shown in FIG. 28, instrument cable (252) has one less electrical conduit (e.g., four) than the number of active communication channels (e.g., five) established by mating contact of the signal interface adapter (212) and the instrument connector (250). Thus, the instrument cable (252) has four conduits—one conduit for delivering monopolar power to the instrument and three communication conduits for communicating signals between the instrument and the signal interface adapter (212). Of course any number of mating contacts and conduits may be provided depending on the nature of the surgical instrument and the external electrical device. In the embodiment depicted in FIG. 28, the instrument cable (252) is non-detachably coupled to the instrument connector (250) and instrument (290). In the embodiment of FIG. 29, on the other hand, the instrument cable (352) is removably coupleable to the instrument (390).

Signal interface adapter (212) includes a main cable (214) operatively connected at one end to the signal interface adapter (212), while the other end is adapted for operative connection to the EDS (200). Main signal interface adapter cable (214) has five independent electrical conduits (wires) inside an outer sheath—one conduit for delivering monopolar power to the instrument (via the MSIS) and four communication conduits for communicating signals between the MSIS and the EDS (200). As explained further herein, the high voltage monopolar power signal is isolated from the low power signals in the EDS (200) in order to prevent stray electrical currents which could create a hazard such as burns (to the patient or medical practitioner), fires, or damage to other equipment. Accordingly, while the high voltage power signal and the low voltage signals are carried on conductors housed within a common outer sheath along the majority of the main cable (214), the proximal end of the main cable (214) is bifurcated in order that the connection of the monopolar high power conductor (214A) to the EDS (200) is spaced apart from the connection of the low power conductors (214B) to the EDS. This helps to ensure sufficient creepage distance and clearance distance, thereby aiding in the isolation of the high voltage components from the low voltage components for safety purposes (including meeting applicable safety standards, particularly IEC 60601).

EDS (200) is operatively connected to a monopolar electrosurgical generator (201) by a power supply line (or conduit) (202). High voltage RF current is delivered to the EDS (200) over power supply line (202) for transmission to the instrument (290). Typically (and as shown), the supply line (202) connects to a connector located on the front of the generator (201). Energy is returned to the generator (201) through one or more return electrodes (203) in conductive contact with the patient, via a return line (204) connected to another connector located on the front of the generator (201). As is known to those skilled in the art, the generator includes electronic circuitry configured for generating RF power specifically suited for various monopolar electrosurgical treatment modalities (e.g., cutting, coagulating, etc.). The generator (201) also includes various user controls for turning the generator on, selecting power levels, selecting treatment modalities (particularly cutting ("CUT") and coagulation ("COAG") modes). In some instances, the generator (201) is also capable of supplying RF power to bipolar instruments.

EDS (200) acts as a circuit breaker between the generator (201) and the instrument (290), mediated by the MSIS (210). The EDS (200) is configured such that RF power can only be transmitted from the generator (201) to the instrument (290) when the instrument connector (250) is matingly engaged with the signal interface adapter (212). The power delivery circuit within EDS (200) placing power supply line (202) in electrical communication with power conductor (214A) is closed when the components of MSIS (210) are in mating engagement—indicating that the instrument has been properly inserted into the trocar and the user is ready to apply RF current to tissue in a patient. Some embodiments of the EDS include a microprocessor that detects whether there is mating engagement between the instrument connector (212) and the signal interface adapter (250), while other embodiments use non-programmable components such a comparator to detect mating engagement. When mating engagement is detected (e.g., from a voltage resulting from the mating engagement of contacts on the MSIS), the microprocessor or other control circuitry in the EDS generates a relay control signal that causes the closure of a relay (e.g., a reed relay, a mechanical relay or a solid-state relay) placing power supply line (202) in electrical communication with power conductor (214A). Other embodiments of the EDS employ discrete components (or analog components) for detecting mating engagement of the components of the MSIS and placing the power supply line (202) in electrical communication with power conductor (214A).

It will be understood, however, that closure of the power delivery circuit in the EDS (200) does not mean that RF current is delivered to the end effector of the instrument (290). Rather, the medical practitioner still must activate the generator (i.e., cause the generator to deliver RF current along power supply line (202)) by actuating a device activation switch, typically located on a footswitch assembly (284) and/or on the instrument itself (e.g., hand switches (279A, 279B)). Upon activation by the user, RF current is delivered to the treatment site adjacent the end effector of the instrument (290).

In embodiments of the EDS providing for hand switch operation of the surgical instrument, the EDS also passes hand switch signals from the instrument to the generator (201) for user-controlled operation of the generator. In one particular embodiment, the microprocessor in the EDS (200) receives one or more hand switch signals from the instrument (via the MSIS) and uses those signals to control relays for generating switching signals that emulate footswitch signals. These switching signals are then transmitted to the generator (201) along control signal cable (205) (see FIG. 28) operatively connected to a footswitch port of the generator (e.g., on the rear of the generator (201) in FIG. 28).

Figure 33:
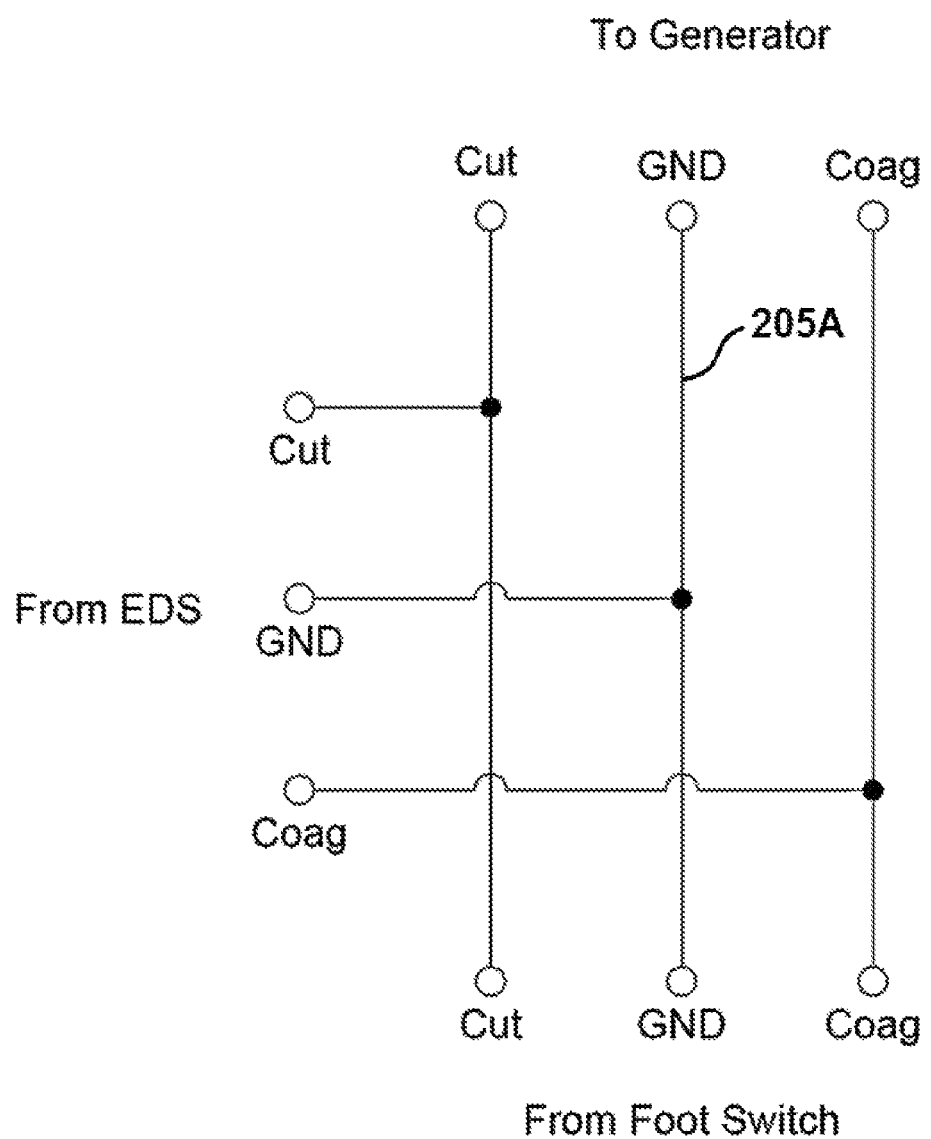
Figure 34:
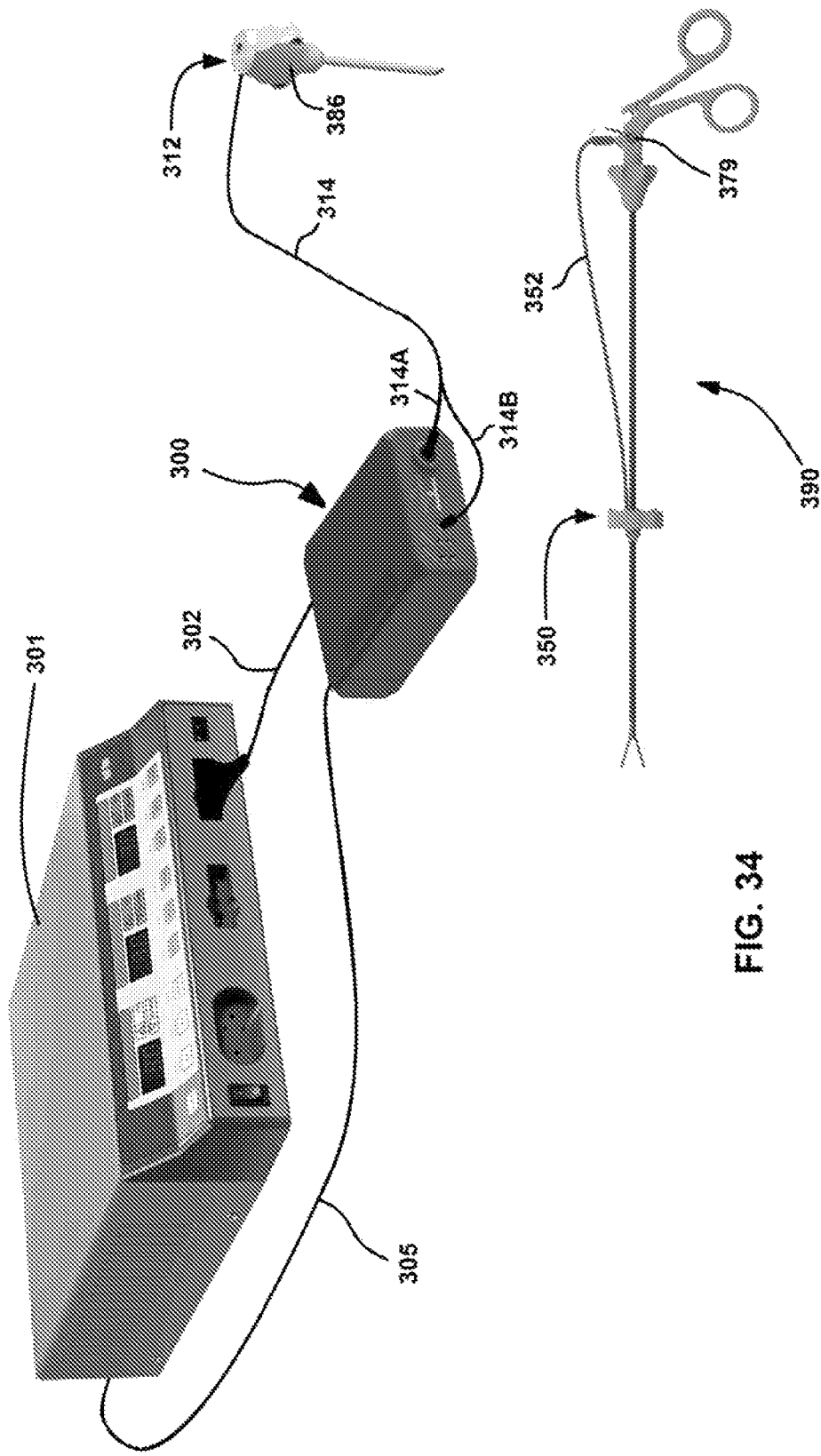
FIG. 34 depicts a schematic illustration of an alternative embodiment of an electrosurgical system similar to that shown in FIG. 28.

In some embodiments of the EDS, a standard footswitch (284) can also be used by connecting the footswitch conduit (206) to a "T" connection (288) (depicted schematically in FIG. 33) that allows switching signals from the EDS as well as from the footswitch to be transmitted in parallel to the generator along control signal cable (405). Alternatively, particularly when the generator includes both footswitch and hand switch control (i.e., has both footswitch and hand switch connections), a footswitch can be connected directly to the generator in the usual manner, bypassing the EDS. This is shown, for example, in the alternative embodiment of FIG. 52.

Figure 30:
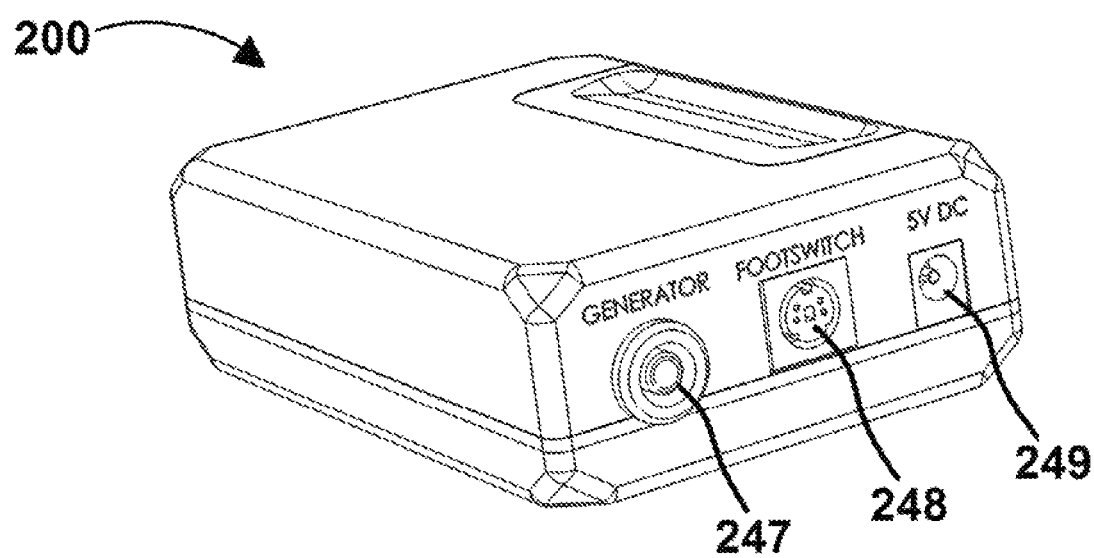
Figure 31:
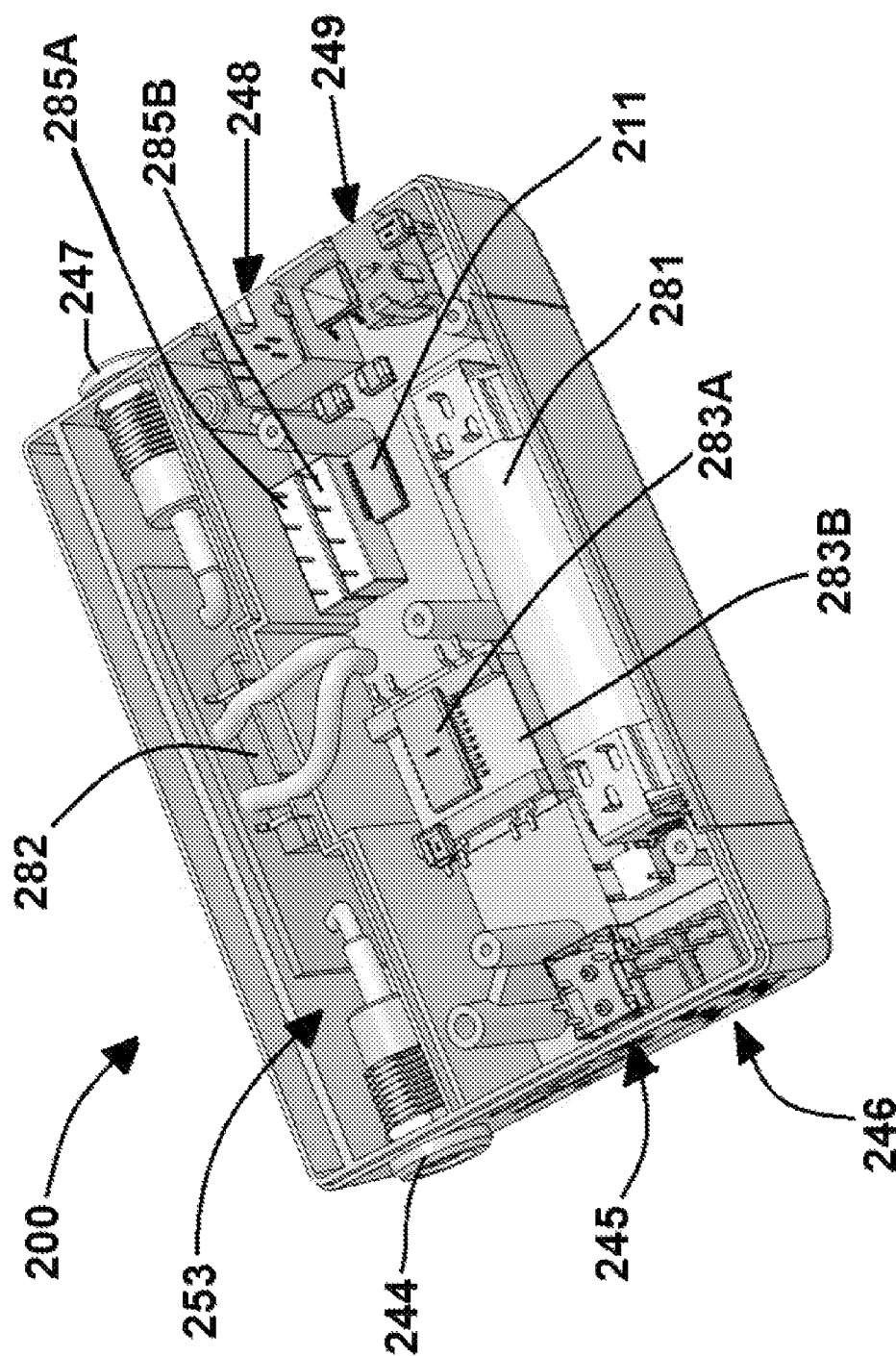
FIG. 31 is a schematic view of the EDS of FIG. 29, with the bottom cover removed, and the printed circuit board and certain other electronic components omitted for clarity.
Figure 32:
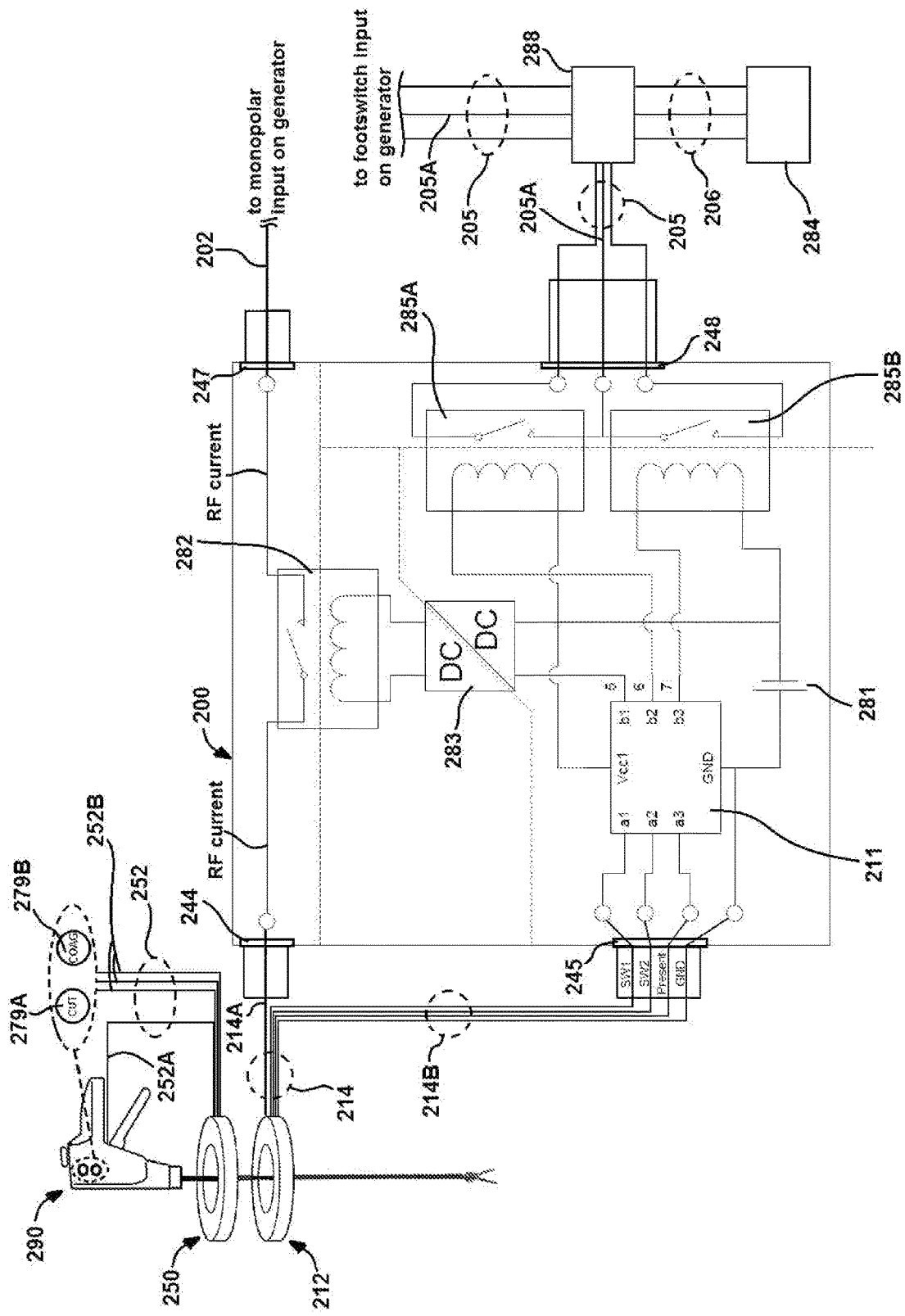
FIG. 32 is a schematic circuit diagram of the electrosurgical system of FIG. 28, and FIG. 33 schematically depicts the T-connection of FIGS. 28 and 32.

FIGS. 29 and 30 depict front and rear views, respectively, of the EDS (200) used in the embodiments of FIG. 28. FIG. 31 is a schematic view of the EDS (200), with the bottom cover removed, and the printed circuit board and certain other electronic components omitted for clarity. FIG. 32 is a schematic circuit diagram of the EDS (200), which also depicts the circuit isolation features of the EDS (200) as well as the connections (via the MSIS) to the surgical instrument (290) of FIG. 28. It will be understood that the MSIS and EDS are shown schematically in FIG. 32 and are not drawn to scale with respect to the instrument. In addition, the cables are depicted schematically in FIG. 33 as distinct conductors rather than as a cable having internal conductors (i.e., the outer sheaths of the cables are omitted in FIG. 32).

EDS (200) includes first, second, third and fourth connectors (244, 247, 248, 245, respectively). As seen in FIG. 29, the front of the EDS (200) case includes a first connector (244) for operatively connecting the monopolar high power conductor (214A) thereto, and a fourth connector (245) for operatively connecting the low power control signal conductors (214B) thereto. In the particular embodiment shown, the first connector (244) is a female banana plug connector (e.g., a 4 mm shielded banana plug) for receiving a male banana plug connector on the terminus of high power conductor (214A). The fourth connector (245) is a female 4-conductor connector (e.g., 3.5 mm) for receiving a mating jack on the terminus of the low power conductor (214B). The front of the case also includes various indicator LED's (246) for signaling operational parameters of the EDS (e.g., one or more LEDs configured to light and/or change color upon detection of mating engagement of the MSIS components).

As seen in FIG. 30, the rear of the EDS (200) case includes a second connector (247) for operatively connecting the power supply line (202) from the generator, and a third connector (248) for operatively connecting the control signal cable (205). In the particular embodiment shown, the second connector (247) is a female banana plug connector (e.g., a 4 mm shielded banana plug) for receiving a male banana plug connector on the terminus of power supply line (202). The third connector (248) is a female DIN connector for receiving a mating male DIN connector on the terminus of the control signal cable (205).

The EDS (200) includes a power supply and/or is adapted to be operatively connected to an external power supply. In the embodiment shown, the power supply comprises a battery (281), such as a rechargeable or non-rechargeable battery. Also, the rear of the EDS case optionally includes a power connector (249) (omitted in FIG. 32) for attachment to a power source such as an AC to DC (e.g., 5V) power converter for purposes of recharging the battery (281), and/or supplying operational or backup power to the EDS (200).

The EDS (200) further includes one or more processors (e.g., a microprocessor or microcontroller) that receives a signal from the MSIS indicative of the instrument connector (250) and the signal interface adapter (212) being in mating engagement, as well as control signals from actuation of either hand switch (279A, 279B) on the instrument indicating the user-activation of either a "CUT" (cutting) or "COAG" (coagulation) mode of operation. These signals are processed by the processor(s), which then generates control signals used to control the delivery of high voltage monopolar power to the surgical instrument (290) via main cable (214). In other embodiments described herein, only a single hand switch is provided, and the EDS supplies a single hand switch signal to the generator. When the generator is configured to receive more than one hand switch signal (e.g., a CUT signal and a COAG signal), the EDS and its associated connector can be configured to supply only one of the plurality of hand switch signals (e.g., a CUT signal or a COAG signal).

In particular, when mating engagement is detected (e.g., from a voltage resulting from the mating engagement of contacts on the instrument connector with corresponding contacts on the signal interface adapter of the MSIS), the microprocessor (211) causes the closure of a switch (282) (e.g., a reed relay switch) within the EDS (200). Closure of this switch (282) places power supply line (202) in electrical communication with power conductor (214A) (see FIG. 32). However, RF power is not delivered over this electrically communicative path to the surgical instrument until an actuation signal is provided to the generator (either from the EDS (200) or from footswitch (284)). Thus, closure of the switch (282) places the system into ready mode—i.e., ready to transmit electrosurgical energy from the generator to the surgical instrument upon user activation of the generator.

It will be understood that the functionality provided by the microprocessor alternatively can be performed using discrete electrical components (or analog components) to perform one or more of the control functions described herein.

As noted above, the MSIS of the embodiment of FIGS. 28 and 32 is that shown in FIGS. 9-27 and described above. Alternatively, the MSIS of FIGS. 9-27 can be modified such that the annular rings (222, 260) of the signal interface adapter (212) and instrument connector (250) are not conductive since the annular rings are not needed for establishing a communication channel in the embodiment of FIGS. 28 and 32.

The MSIS (210) of FIGS. 9-27 is used in the manner described above in the system depicted in FIGS. 28 and 32. The outer bands of contacts (227A, 264A) are used for transmitting monopolar RF current from the high power conductor (214) to the instrument (290) (for delivery to the end effector thereof). Upon mating engagement of the of the interface adapter (212) and the instrument connector (250), each one of the outer band contacts (264A) of the instrument connector (250) will be in mating engagement (i.e., contact providing electrical communication) with a corresponding and predetermined one of the outer band contacts (227A) on the signal interface adapter (212). This conductive contact will allow for the transmission of high voltage monopolar current in parallel, thereby providing redundancy and ensuring proper transmission of the RF current. Alternatively, fewer than four pairs (even one pair) of mating contacts can be used for transmitting RF current.

The inner band of contacts (227B, 264B) is used for transmitting low power control signals (including GND) between the MSIS and the EDS (200). Upon mating engagement of the of the signal interface adapter (212) and the instrument connector (250), each one of the inner band contacts (264B) of the instrument connector (250) will be in mating engagement (i.e., contact providing electrical communication) with a corresponding and predetermined one of the inner band contacts (227B) on the signal interface adapter (212). One pair of mating contacts (227B, 264B) is used for GND, one pair is used for a first switching signal (SW1 in FIG. 32), one pair is used for a second switching signal (SW2 in FIG. 32), and the last pair of mating contacts (227B, 264B) is used for an engagement signal ("Present" in FIG. 32).

In the instrument connector (250), the contact (264B) used for the engagement signal is in electrical communication with the contact (264B) used for GND (via a conductor, e.g., a conductive trace) connecting the two contacts (264B)). (For this reason instrument cable (252) only has four conductors—one for transmitting monopolar RF current, and three for SW1, SW2 and GND.) Thus, upon mating engagement of the MSIS components, the engagement signal line will in electrical communication with GND, thereby providing a voltage signal at input a3 of the microprocessor (211). Microprocessor (211) is programmed to provide a closure signal to reed relay (282), through a DC/DC converter/isolator (283) (further described below), causing relay (282) to close.

The other three matingly engaged contacts (227B, 264B) are used for providing switch closure signals (SW1, SW2) to the microprocessor. For example, when switch (e.g., a button) (279A) is actuated by the user, the SW1 signal line will in electrical communication with GND, thereby providing a voltage signal indicative of switch closure at input a1 of the microprocessor (211). Similarly, when second switch (e.g., a button) (279B) is actuated by the user, the SW2 signal line will in electrical communication with GND, thereby providing a voltage signal indicative of switch closure at input a2 of the microprocessor (211).

Since footswitches commonly used with electrosurgical generators are simple, normally open, SPST switches, relays (285A, 285B) (e.g., reed relays) are used to emulate footswitch signals, thereby allowing hand switch control of electrosurgical generators configured only for footswitch control. As seen in FIG. 32, microprocessor (211) is adapted to transmit closure signals to relays (285A, 285B), each of which is in electrical communication with the generator via third connector (248) and control signal cable (205). In other words, relays (285A, 285B) act as normally open, SPST switches. Since each relay is in electrical communication with the common return line (205A; also referred to as GND in FIG. 6A) of the control signal cable (205) (the same common return line/GND (205A) used by a conventional footswitch (284), closure of a relay (285A, 285B) provides the same signal to the generator that would be supplied by the actuation of a footswitch pedal (284A, 284B).

First relay (285A) is assigned to first hand switch (279A) (i.e., SW1), and the second relay (285B) is assigned to second hand switch (279B) (i.e., SW2). When the microprocessor detects that first hand switch (279A) has been actuated by the user, the microprocessor causes a closure signal to be sent to first relay (285A). This results in a first footswitch actuation signal to be provided to the generator (201), wherein the first footswitch actuation signal is identical to the signal provided to the generator if first footswitch pedal (284A) were actuated. When the microprocessor detects that second hand switch (279B) has been actuated by the user, the microprocessor causes a closure signal to be sent to second relay (285B). This results in a second footswitch actuation signal to be provided to the generator (201), wherein the second footswitch actuation signal is identical to the signal provided to the generator if second footswitch pedal (284B) were actuated. In this manner, the EDS (200) provides footswitch emulation for hand switches (279A, 279B) (since the generator (201) cannot tell the difference between a signal resulting from the closure of one of the relays (285A, 285B) and one resulting from the actuation of a footswitch pedal (284A, 284B).

In some embodiments the EDS (200) is configured such that neither low voltage relay (285A, 285B) will be closed unless high voltage relay (282) is also closed. In this manner, the generator (201) will only be activated if the MSIS components are in mating engagement (i.e., the surgical instrument is inside the trocar cannula, ready to be used). In alternative embodiments the closing of the low voltage relays (285A, 285B) is not dependent upon the status of high voltage relay (282). In such embodiments, even if the generator is activated (e.g., by the user actuating one of the hand switches (279A, 279B) or one of the footswitches (284A, 284B)), RF current will not be delivered to the surgical instrument unless high voltage relay (282) is closed. Also, the use of low voltage relays (285A, 285B) allows for the control (i.e., limiting) of the voltage signal near the patient resulting from actuation of the hand switches. The use of low voltage relays (285A, 285B) also isolates the hand switches from the generator for safety purposes and to meet applicable safety standards such as IEC 60601. This isolation is depicted by the dashed lines in FIG. 32 that extend through the low voltage relays (285A, 285B).

One of the inherent concerns with monopolar surgical instruments and generators is the need to isolate high voltage components and signals from the low voltage ones. Embodiments of the EDS are configured to provide such isolation and additional safety measures for patient and practitioner safety—including "Means of Protection" (or "MOPs"), as defined in IEC 60601. (It will be understood that the terms "Means or Protection," "Means of Patient Protection" and "Means of Operator Protection" refer to defined terms used in, for example, IEC 60601—a series of technical standards for the safety and effectiveness of medical electrical equipment, published by the International Electrotechnical Commission. These terms do not refer to, and are not intended to invoke, so-called "means-plus-function" limitations or elements under applicable patent law.)

In general, medical electrical devices should incorporate one or more Means of Protection (MOPs) to isolate patients and operators from the risks of electrocution. A MOP can be safety insulation, a protective earth, a defined creepage distance, or an air gap or other protective impedance. IEC 60601-1 differentiates between the risk to patients and the risk to operators. A MOP can therefore be classified as Means of Patient Protection (MOPP) or a Means of Operator Protection (MOOP). Potential leakage currents relevant to the EDS described herein include: i) Earth leakage; ii) Enclosure leakage; and iii) Applied Part (or Patient) leakage.

The Applied Parts of concern in the EDS include the connection of the EDS to the power connection of the RF generator (or other external electrical device) and the connection to the MSIS (leakage to a user or patient to earth ground is the concern). It should be kept in mind that the EDS (200) is essentially a switch in line with the power output of the electrosurgical generator (201). The EDS does not alter, modify or even monitor the RF current (or other treatment energy) supplied by the generator; nor does the EDS monitor the health or status of an electrosurgical generator to which the EDS is connected. An attached RF generator (or other external electrical device) is assumed to pass all IEC60601 testing protocols, and therefore the RF generator (or other external electrical device) is assumed to be properly configured with 2XMOPP protection.

Embodiments of the EDS provide 1XMOPP from all low voltage (<7V) components and 2XMOPP from any components that are at elevated voltages. The first MOPP is provided by manufacturing the EDS case from an insulating plastic material. All penetrations of the case are shielded internally to reduce EMI susceptibility and provide emission protection. The second MOPP of embodiments described herein occurs in two places: the footswitch emulator relays (285A, 285B) and the RF power relay (282). In one embodiment, the footswitch emulator relays (285A, 285B) are standard reed relays with 600 VAC of isolation between the coil and the contacts. Since the footswitch port of the RF generator (201) is protected, voltages more than 600 VAC should not occur on the switch side of the relays (285A, 285B).

In the embodiment of EDS (200) shown in FIGS. 28-32, the RF power relay (282) is a high voltage relay that provides 7 kVDC isolation between the switch and the coil. In addition to the relay's inherent isolation, the relay is in a separate internal compartment (253) (see FIG. 31) that is filled with an insulating potting compound. The potting compound ensures that the high voltages of the RF current (up to 10 kV) are fully insulated for safety purposes.

Also, should there be a breakdown between the contacts and the coil of the RF power relay (282), the coil excitation is on the secondary side of DC/DC converter/isolator (283) that provides 5 kVrms isolation. The DC/DC converter/isolator (283) (also referred to in the art as a DC-to-DC converter) has two parts. First, an isolation transformer (283B) ensure that the necessary power for driving the relay (282) is provided while preventing any current flow from one side to the other. The DC/DC converter/isolator also includes an IC chip (283A) that includes internal components and circuitry for sensing voltage on one of several lines, converting that voltage to a magnetic signal on one side, and finally convert that magnetic signal to voltage on the other side. While DC voltages are on the input and output sides of the DC/DC converter/isolator (283), the two sides are insulated from each other, thereby providing an additional safety layer. Of course, it will be understood that the DC/DC converter/isolator (283) can be omitted in an alternative embodiment.

The DC/DC converter/isolator (283) also provides four channels of data communications, with two of those channels used to control the relay (282). These two channels are used to initially close the relay (282) and then to provide a lower power holding voltage to maintain closure of the relay. FIG. 32 schematically illustrates the overall circuit isolation features provided by the use of a magnetic reed switch (i.e., relay (282)), the use of a DC/DC converter/isolator (283) between the microprocessor (211) and the high voltage relay (282), and the use of reed relays (285A, 285B) between the microprocessor (211) and the connection to the RF generator (201). While a DC-to-DC converter is not depicted in the embodiments of FIGS. 52 and 53, it will be understood that one can be provided between the microprocessor (411, 511) and the first reed relay (482, 582). Alternatively, or in addition thereto, one or more transistors or other electrical components can be located between the microprocessor (211, 411, 511) and the relays (282, 285A, 285B, 482, 485, 582, 585) in order to drive the relays using closure signals output by the microprocessor.

FIGS. 34-38 are schematic illustrations of an alternative embodiment of a MSIS comprising an instrument connector (350) and a signal interface adapter (312). The signal interface adapter is shown attached to the proximal end of a trocar cannula housing (386), and the instrument connector (350) is shown mounted on the shaft of a monopolar surgical instrument (390) (once again, monopolar forceps). A main cable (314) extends from the signal interface adapter (312). The proximal end of the main cable (314) is once again bifurcated in order that the monopolar power conductor (314A) can be connected to the EDS separately from the low power conductors (314B). In the embodiment shown, banana plugs at the ends of the monopolar power conductor (314A) and the low power conductors (314B) are operatively connected to the first and second inputs on the front of the EDS. An instrument cable (352) is operatively connected between the instrument connector (350) and the instrument handle for transmitting electrical signals between the instrument connector (350) and the instrument (390). In this embodiment, the instrument cable (352) is not wound about the instrument shaft.

A single switch in the form of a button (379) is attached to the side of the instrument handle, and is used for actuating the delivery of RF current to the instrument (390). Optionally, one or more additional buttons or other switches may be provided on the instrument for controlling the delivery of RF current from the generator (e.g., to select a mode of operation such as CUT or COAG). In the embodiment shown in FIG. 34, a footswitch is not included, and therefore the operation of the instrument (390) is controlled by the button (379) (e.g., RF current on/off). The EDS (300) can be configured the same as the EDS (200) described previously, or can be modified to include only a single low voltage relay when a single activation button (379) is provided on the instrument. When operatively connected to a generator having more than one user-selectable operational mode (e.g., CUT and COAG), the EDS (300) can be configured to supply a signal activating one of the operational modes (e.g., CUT only, or COAG only). This can be accomplished, for example, by configuring the connector used to operatively connect the EDS to the generator in the desired manner.

In this embodiment, the surgical instrument (390) is not manufactured with hand switches, and is therefore designed for use with footswitch activation by the user. However, embodiments of the present disclosure provide hand switches that can be retrofit to a surgical instrument to provide hand switch control of the instrument using existing external electrical devices (e.g., RF generators). In some embodiments the EDS is configured to provide footswitch emulation for hand switches operatively connected thereto, while in other embodiments the EMS and allows for retrofit hand switches to be connected to generator ports for hand switch signals. In the embodiment of FIGS. 34-38, the EDS is configured to provide footswitch emulation for hand switch (379), similar to that described previously with respect to EDS (200). Thus, one or more hand switches (e.g., push button (379) are provided in electrical communication with the instrument connector (350) of the MSIS—either integral with the instrument cable (352) or operably attachable thereto.

Instrument (390) includes an end effector (392A) at the distal end of shaft (392), with a handle assembly (394) located at the proximal end of the shaft (392). The handle assembly includes a stationary handle (394A) and a moveable (i.e., pivoting) handle (394B) for closing the jaw members of the end effector (392A). A rotation knob (395) is also provided for rotating the end effector (392A) with respect to the handle assembly (132), as is known to those skilled in the art.

The instrument connector (350) (similar to the instrument connector (250) described above) is slidably mounted on the shaft (392) of the instrument, and includes an instrument cable (352) operably attached thereto. Instead of routing the conductors of the instrument cable (352) into the handle assembly of the instrument as in the previous embodiment, instrument cable (352) is routed outside of the instrument (390) and handle assembly (394). Also, the hand switch (e.g., button (379) is operatively connected to the instrument cable (352) (e.g., via ribbon cable (398), also referred to herein as the switch cable) rather than being integral with the instrument.

Figure 36:
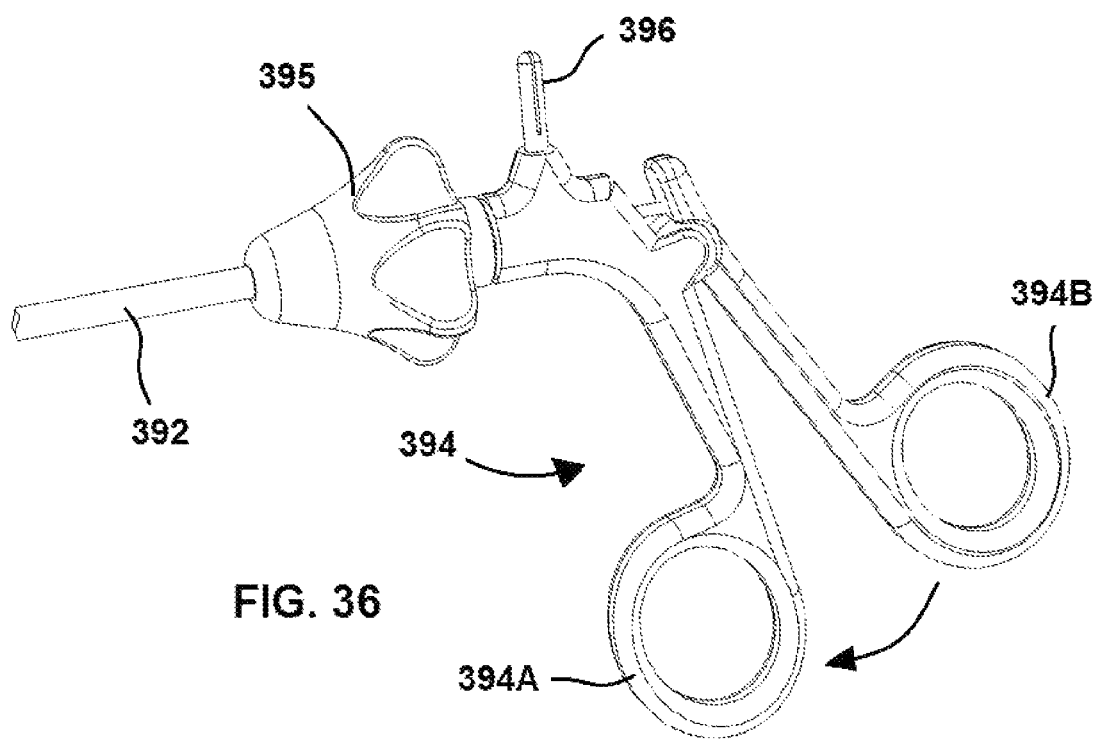
FIG. 36 depicts the handle portion of the surgical instrument.
Figure 37:
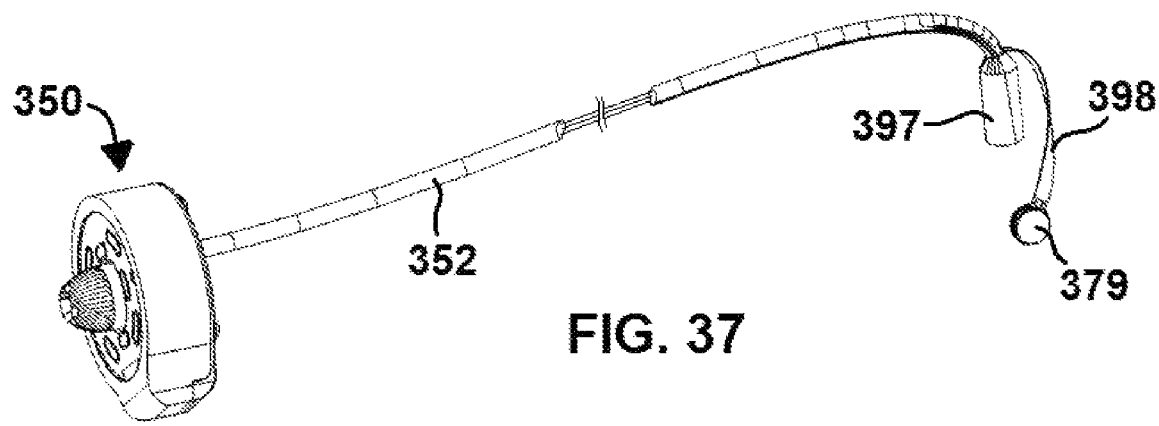
FIGS. 37 and 38 depict the instrument connector and associated cabling of the system shown in FIG. 34.
Figure 38:
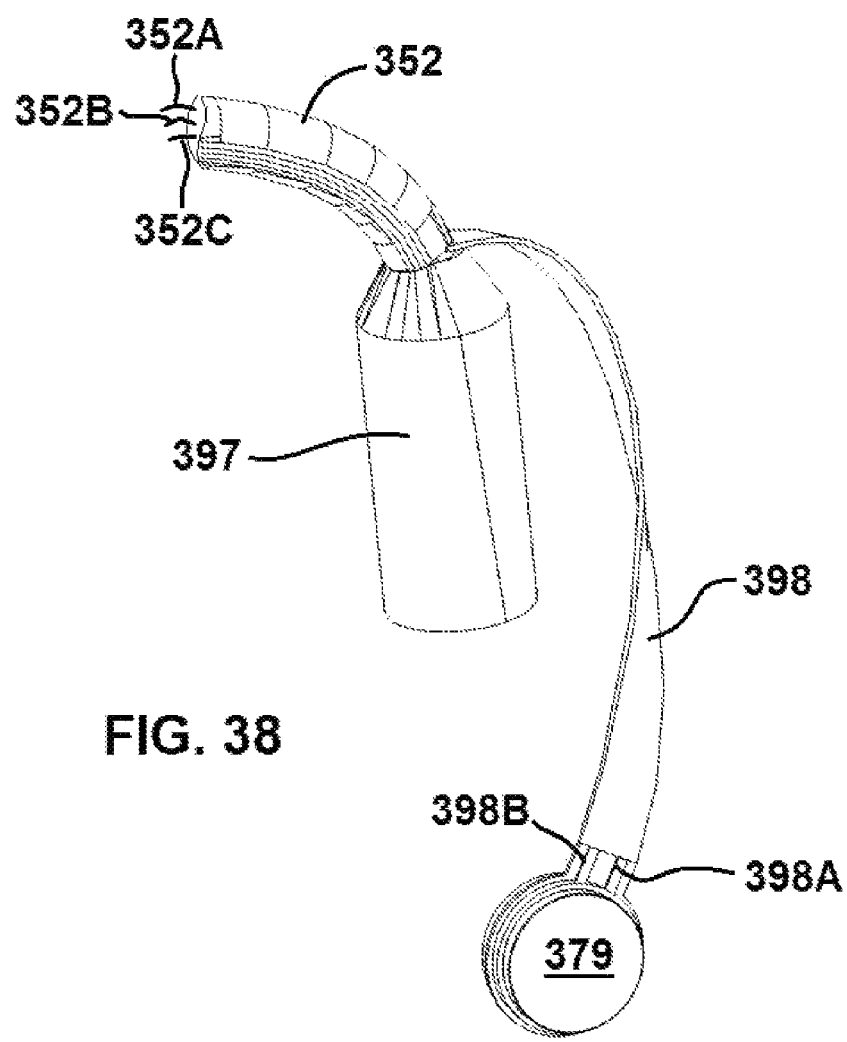

In particular, as best seen in FIG. 36 the instrument handle assembly (394) includes a post connector (396) (e.g., similar to a male banana plug connector) that is in electrical communication with the end effector electrode (e.g., one of the jaw members). The distal end of the instrument cable (352) includes a female plug connector (397) configured for operative engagement with the post connector (396). The female plug connector (397) is in electrical communication with the monopolar high power RF conductor of the instrument cable (352), and therefore, when attached to the post connector (396), delivers RF current to the end effector (392A). A two conductor ribbon cable (398) extends out of the sheathing of the instrument cable (352), and is used to route two low power conductors (e.g., one being GND) to the button (379).

The button (379) also includes pressure sensitive adhesive on its bottom surface for attachment to the handle assembly (394) at a convenient location selected by a user. An additional button (379) can be provided in electrical communication with the instrument cable (352) and attached to the handle assembly (394), thus providing the same functionality as in the previous embodiment—e.g., CUT and COAG modes activated from the handle assembly using hand switches (394) that emulate foot pedals conventionally used with monopolar instruments. In the example shown, however, only a single button is employed and the instrument cable (352) only requires three conductors (352A, 352B, 352C), and ribbon cable (398) has two conductors (398A, 398c) as shown. Accordingly, the embodiment of FIGS. 34-38 allow the system to provide hand switches on off-the-shelf monopolar instruments that otherwise could only be operated using a footswitch.

Figure 43:
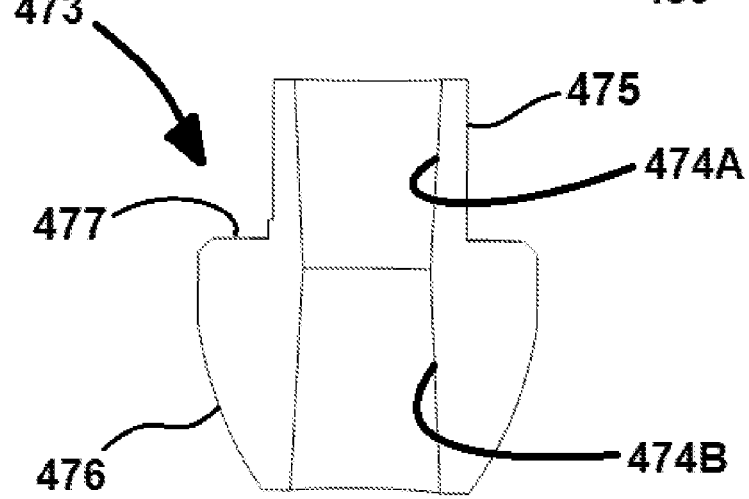
FIG. 43 is a cross-sectional view of the guide cap of the instrument connector.
Figure 46:
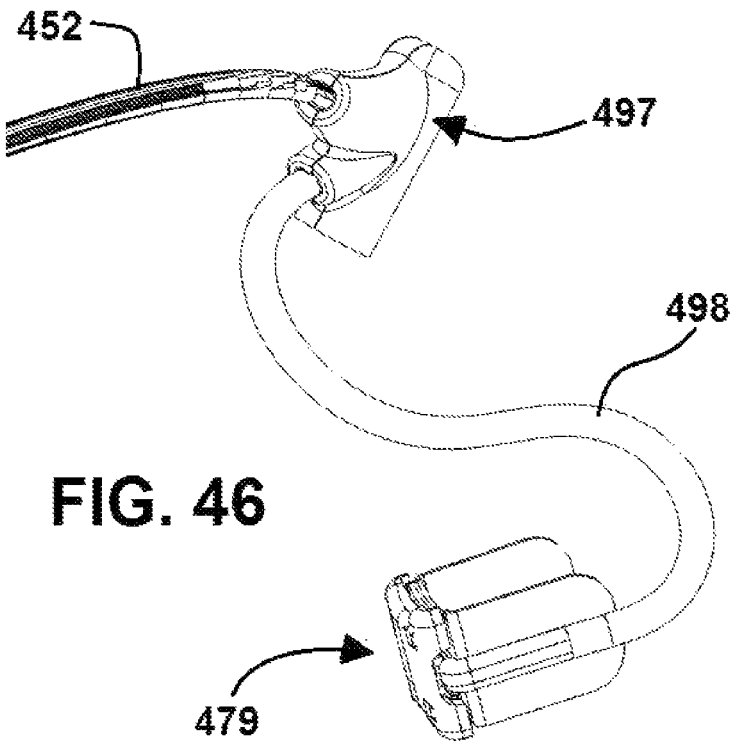
FIG. 46 depicts a portion of the instrument cable, as well as the plug connector, switch cable, and switch assembly of the instrument connector of FIG. 44.
Figure 47:
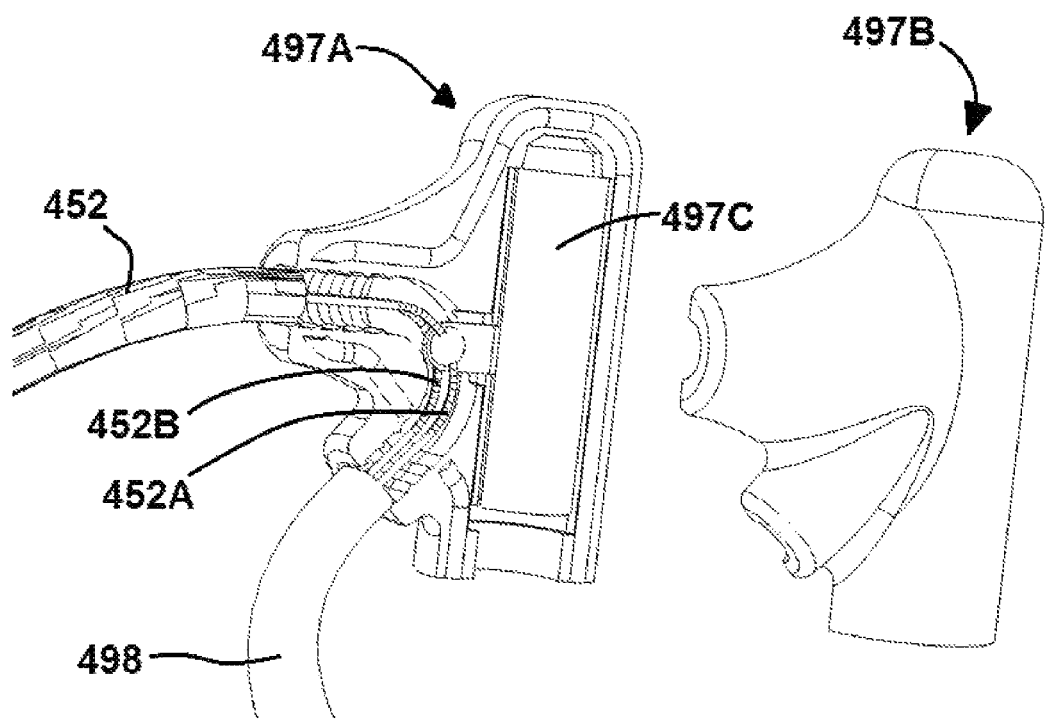
FIG. 47 is an exploded view of the plug connector of FIG. 46.

FIGS. 39-49 depict yet another alternative embodiment of a MSIS (410) comprising a signal interface adapter (412) and an instrument connector (450). FIG. 44 is similar to FIG. 3, and depicts the signal interface adapter (412) removably mounted to a trocar cannula housing (486) and the instrument connector (450) slidingly mounted on the elongate shaft (492) of a surgical instrument (monopolar forceps). Planar, mating contacts are provided on each face of the components (412, 450), similar to those described above with respect to the components (50, 212, 250) of previously described embodiments. Like signal interface adapter (212), the signal interface adapter (412) is configured to be removably mounted on the proximal end of a trocar cannula housing (486). FIG. 43 is a cross-sectional view of the guide cap (473) portion of the instrument connector (450), in a plane that includes a longitudinal axis extending through the center of the central aperture (457) of the instrument connector.

Figure 14:
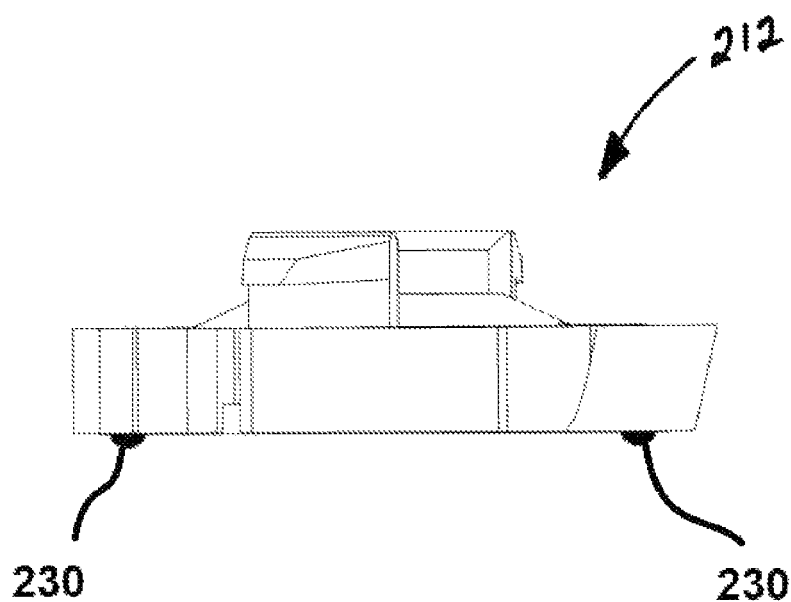

FIGS. 39 and 40 are perspective views of MSIS (410) similar to FIGS. 9 and 10, wherein the signal interface adapter (412) and instrument connector (450) are shown disengaged from one another. FIG. 39 depicts the distal sides of the two components and FIG. 14 depicts the proximal sides. Instrument cable (452) is permanently attached at one end to the instrument connector (450), and main cable (414) is permanently attached at one end to the signal interface adapter (412). As further described below, the instrument connecting end of instrument cable (452) is similar to that described above for FIGS. 34-38, and the EDS engaging end of the main cable (414) includes a connector (435) as shown in FIGS. 44 and 45. Unlike previous embodiments, the main cable (414) is not bifurcated, and the high power and low power conductors of main cable (414) connect to the EDS (400) through a single connector (435).

Once again each component (412, 450) of the MSIS (414) is generally annular in shape, having central apertures (419, 457) extending therethrough. When the two components (412, 450) are in mating engagement with one another, the apertures (419, 457) are axially aligned with one another. The apertures are sized and configured to slidably and rotatably receive an instrument shaft therethrough.

Figure 41:
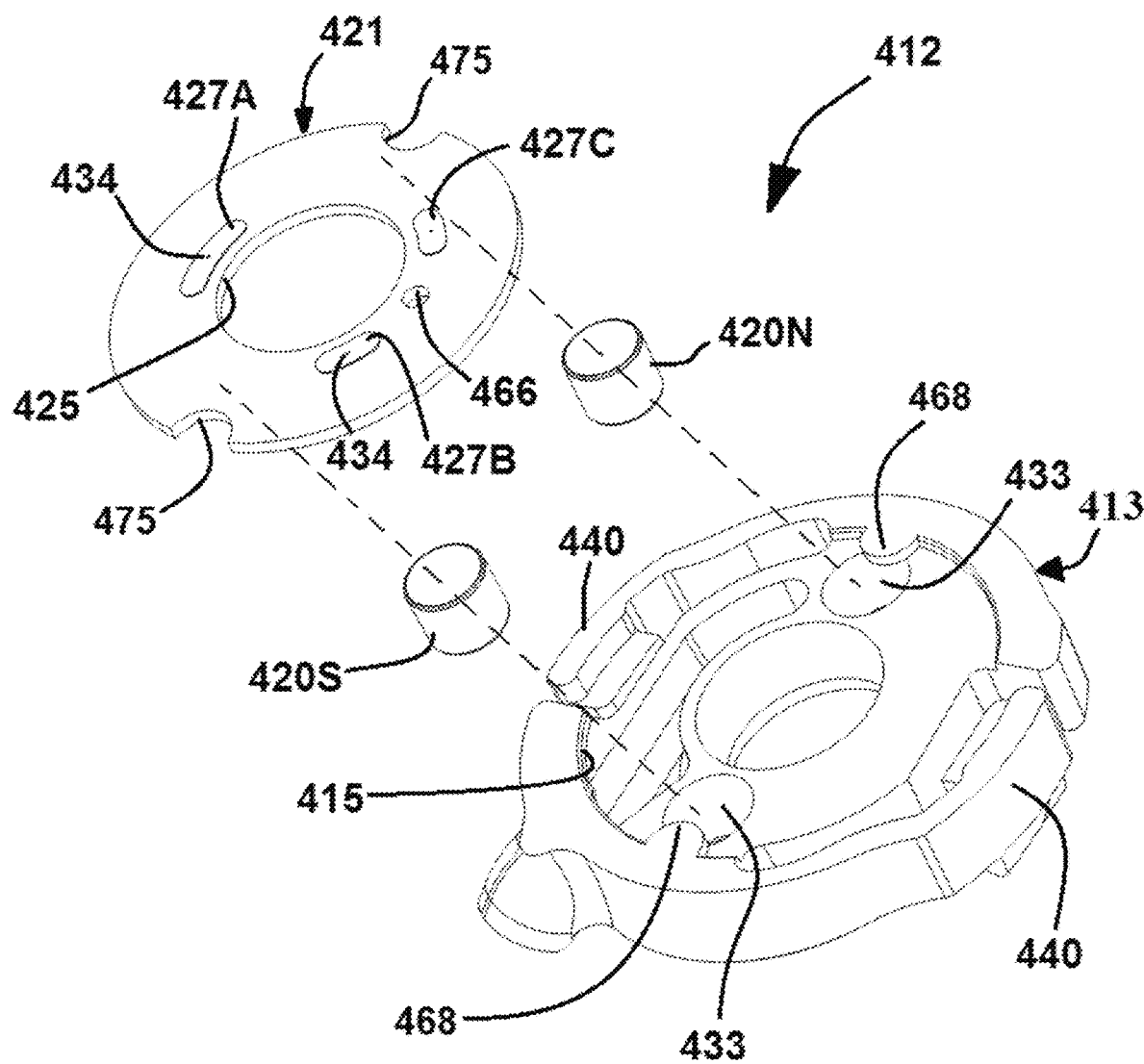
FIG. 41 is an exploded view of the signal interface adapter of FIGS. 39 and 40, viewed from the proximal side.
Figure 42:
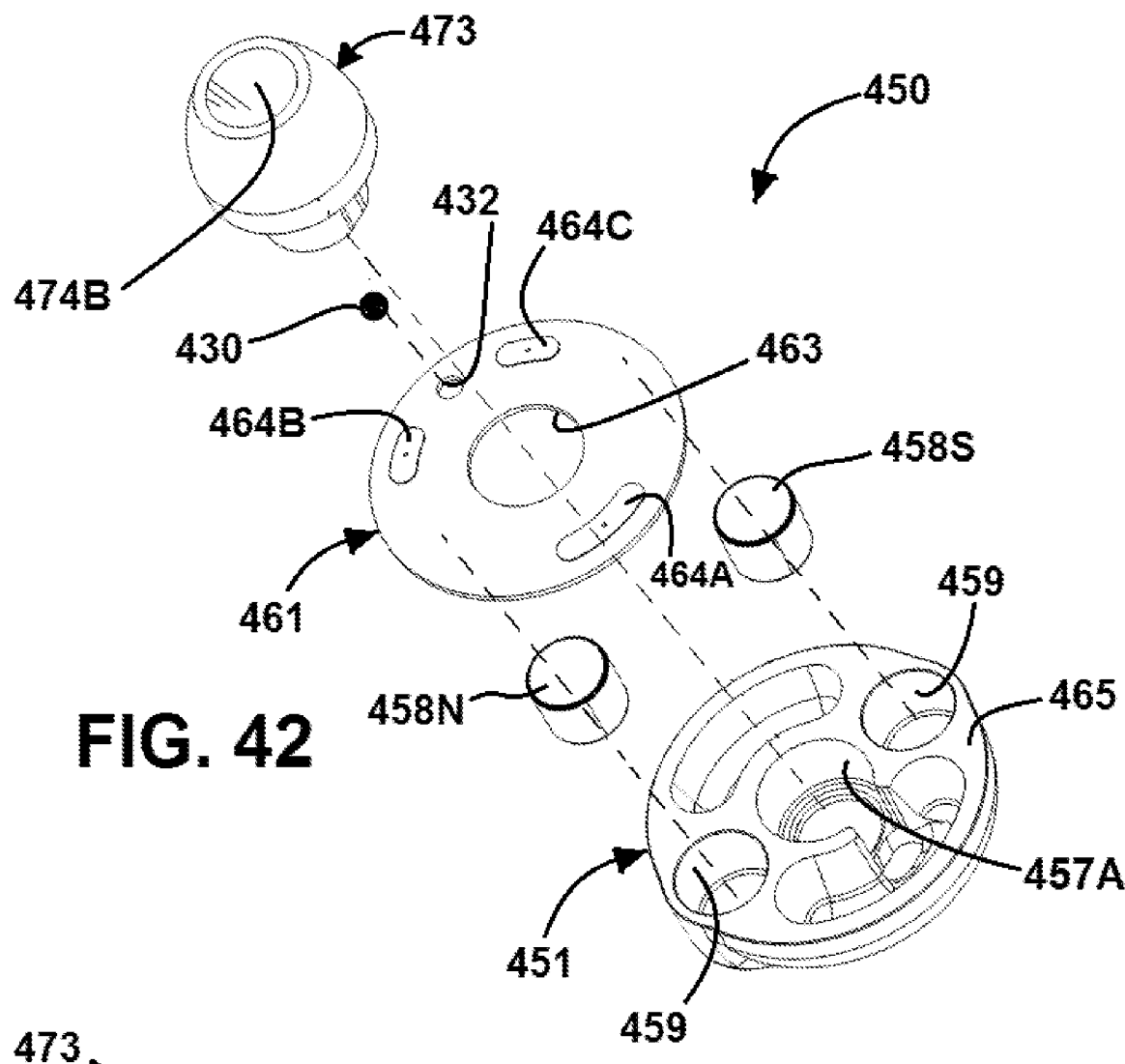
FIG. 42 is an exploded view of the instrument connector of FIGS. 39 and 40, viewed from the distal side.

As best seen in the exploded view of FIG. 41, the signal interface adapter (412) generally comprises a housing (413) and a cover plate (421) mounted thereto. The proximal side of housing (413) is generally cup-shaped, having an outer rim (415) with an inner diameter slightly larger than the outer diameter of PCB cover plate (421). PCB cover plate (421) is received in the proximal side of housing (413), on proximal surface (417) of housing (413), within rim (415). PCB cover plate (421) can be secured in place by an adhesive, mechanical fasteners such as screws or rivets, and/or press fitting. Housing (413) can also include one or more alignment features such as arcuate members (468) that extend radially inward and are shaped and configured for mating alignment with correspondingly shaped cutouts (475) in cover plate (421). It will be understood that these mating alignment features are merely exemplary and a variety of other shapes and number of alignment features can be used to facilitate proper alignment of the cover plate and housing (including alignment features on the instrument connector as well).

A pair of opposite polarity magnets (420N, 420S) are provided on signal interface adapter (412). Similarly, a pair of opposite polarity magnets (458N, 458S) are provided on instrument connector (450). Once again the opposite polarity magnets of each component (412, 450) of the interface system are located 180 degrees apart (i.e., on opposite sides of the central apertures (419, 457)). A pair of cylindrical bores (433) extend through the thickness of housing (413) between proximal end surface (417) and the distal end surface of the housing (not shown). Cylindrical bores (433) receive magnets (420N, 420S) therein, with the magnets held in place by an adhesive, mechanical fasteners, and/or press fitting. On the instrument connector, magnets (458N, 458S) are received in cylindrical cavities (459) that are open at the distal face (465) of housing (451) of the instrument connector (450), and held in place by an adhesive, mechanical fasteners, and/or press fitting (see FIG. 42). Thus, the magnets (420N, 420S, 458S, 458N) are located directly beneath their respective cover plates (421, 461).

On its distal side, the interface adapter (412) is configured to be removably mounted on the proximal end of a trocar cannula housing (e.g., trocar cannula housing (486) in FIG. 44). Like the embodiment of FIGS. 9-27, a pair of spring-like cantilevered arms (440) are provided on opposite sides of the housing (413). Cantilevered arms (440) can be flexed radially inward, and such resilient flexing is enhanced by forming the housing (413) of a suitable resilient material (e.g., molded plastic). A distally extending latch arm (441) is provided at the free end of each cantilevered arm (440), and terminates in radially extending clip (442). The clips (442) are located and configured to be lockingly received by correspondingly shaped slots on the proximal end of a trocar cannula housing, as described previously.

Cover plate (421) is in the form of a multi-layered PCB that is generally is generally annular in shape, having a central aperture (425) corresponding to the central aperture (419) of the interface adapter (412). The PCB cover plate (421) further includes a plurality of conductive contacts (427A-C) on its proximal side, arranged around the central aperture (425). Thus, the PCB cover plate (421) provides three spaced-apart, generally oval-shaped contacts (427A-C) on the proximal face of the signal interface adapter (412). Plated through-holes (or vias) (434) are provided in each of the contacts (427A-C), and connect the contacts (427A-C) to one or more underlying layers that include various electrical traces (not shown) and optionally other electronic components.

As noted in the figures, the conductive contacts (427A-C) on the signal interface adapter (412) and the corresponding conductive contacts (464A-C) on the instrument connector (450) are not evenly arrayed around the central apertures of the components (412, 450). In other words, the centers of the contacts on a component (412, 450) are not spaced 120 degrees apart around the central apertures. Instead, the first (high power) contact (427A, 463A) is positioned on one side of the central aperture (425, 463), and the second and third low power contacts (477B/C, 463B/C) are located on the opposite side of the central aperture. Thus, the high power, first contact (427A, 463A) is located between about 130 degrees and about 170 degrees from the second contact (427B, 463B) and between about 130 degrees and about 170 degrees from the third contact (427C, 463C) (as measured from the center of each contact). The second contact (427B, 463B) is located between about 20 degrees and about 100 degrees from the third contact (427C, 463C). This results in a larger contact force between the first contacts (427A, 463A) as compared to the contact force between mating second contacts and mating third contacts. Of course, depending on the configuration of the MSIS, it may be desirable to have increased contact force between other pairs of mating contacts, and therefore the arrangement shown is one example.

In addition, the contacts on a component are not of the same size. In the embodiment shown, the first contacts (427A, 463A) are larger than the second and third contacts (427B/C, 463B/C). This provides for a larger contact area between the high power first contacts (427A, 463A) for a more stable connection. In addition, since only three contacts are provided on each component of MSIS (400), it is not necessary to provide resiliently biased contacts in the manner described previously. Thus, both the instrument connector (450) and the signal interface adapter employ PCB, rather than FPCB, cover plates.

Like the previous embodiments, the interface adapter and/or the instrument connector includes one or more alignment projections that are received in corresponding recesses on the other component (412, 450) when the two components are in mating engagement. In this embodiment, a single projection (430) is provided in the distal face of the instrument connector (450) with corresponding recesses (466) provided on the interface adapter (412). In this embodiment, the projection comprises a non-rotatably mounted ball bearing (e.g., a non-conductive ruby ball bearing) that not only prevents non-mating electrical contact prior to proper alignment of the components (412, 450), but also facilitate rotational sliding of the instrument connector and the signal interface adapter. The bearing (430) is captively mounted in an aperture (432) provided in PCB cover plate (461) of the instrument connector (450). Projection (430) extends above the conductive contacts (464A-C) on the distal face of the instrument connector (450), thereby preventing the contacts (464A-C) from contacting the corresponding contacts (427A-C) on the signal interface adapter (412) until the instrument connector is in proper rotational alignment with the signal interface adapter. When proper rotational alignment is achieved, the bearing (430) is received within the recess (466) in the proximal face of the signal interface adapter, and the instrument connector is pulled into mating contact with the interface adapter. It will be understood, of course, that the bearing(s) (230) (or other projections) can be provided on the signal interface adapter connector rather than on (or in addition to) the instrument connector along with corresponding recesses on the instrument connector.

As noted above, main cable (414) is permanently attached at one end to the signal interface adapter (412) and includes three conduits (e.g., wires) therein. These conduits are in electrical communication with the contacts (427A-C) on the proximal face of the signal interface adapter (412), as seen schematically in FIG. 52. The other end of the cable (414) has a three-conductor electrical connector (435) (see FIGS. 44 and 45) configured to be operably received by a corresponding first connector (444) provided on the front of EDS (400) (see FIG. 50), as further described herein. The connector (435) is configured for latching engagement with the first connector (444) of EDS (400). Unlike previous embodiments, the main cable (414) is not bifurcated; the high power and low power conductors of main cable (414) connect to the EDS (400) through a single connector (435).

Turning to the instrument connector (450), this component comprises a housing (451) and a PCB cover plate (461) mounted thereto. Cover plate (461) is in the form of a multi-layered PCB that is generally is generally annular in shape, having a central aperture (463) corresponding to the central aperture (457) of the instrument connector (450). The PCB cover plate (461) further includes a plurality of conductive contacts (464A-C) on its distal side, arranged around the central aperture (463) in the same manner as the conductive contacts (427A-C) of the signal interface adapter (412). Thus, the PCB cover plate (461) provides three spaced-apart, generally oval-shaped contacts (464A-C) on the distal face of the instrument connector (450). Plated through-holes (or vias) are provided in each of the contacts (464A-C), and connect the contacts (464A-C) to one or more underlying layers that include various electrical traces (not shown) and optionally other electronic components (e.g. one or more resistors, as further described herein).

Figure 52:
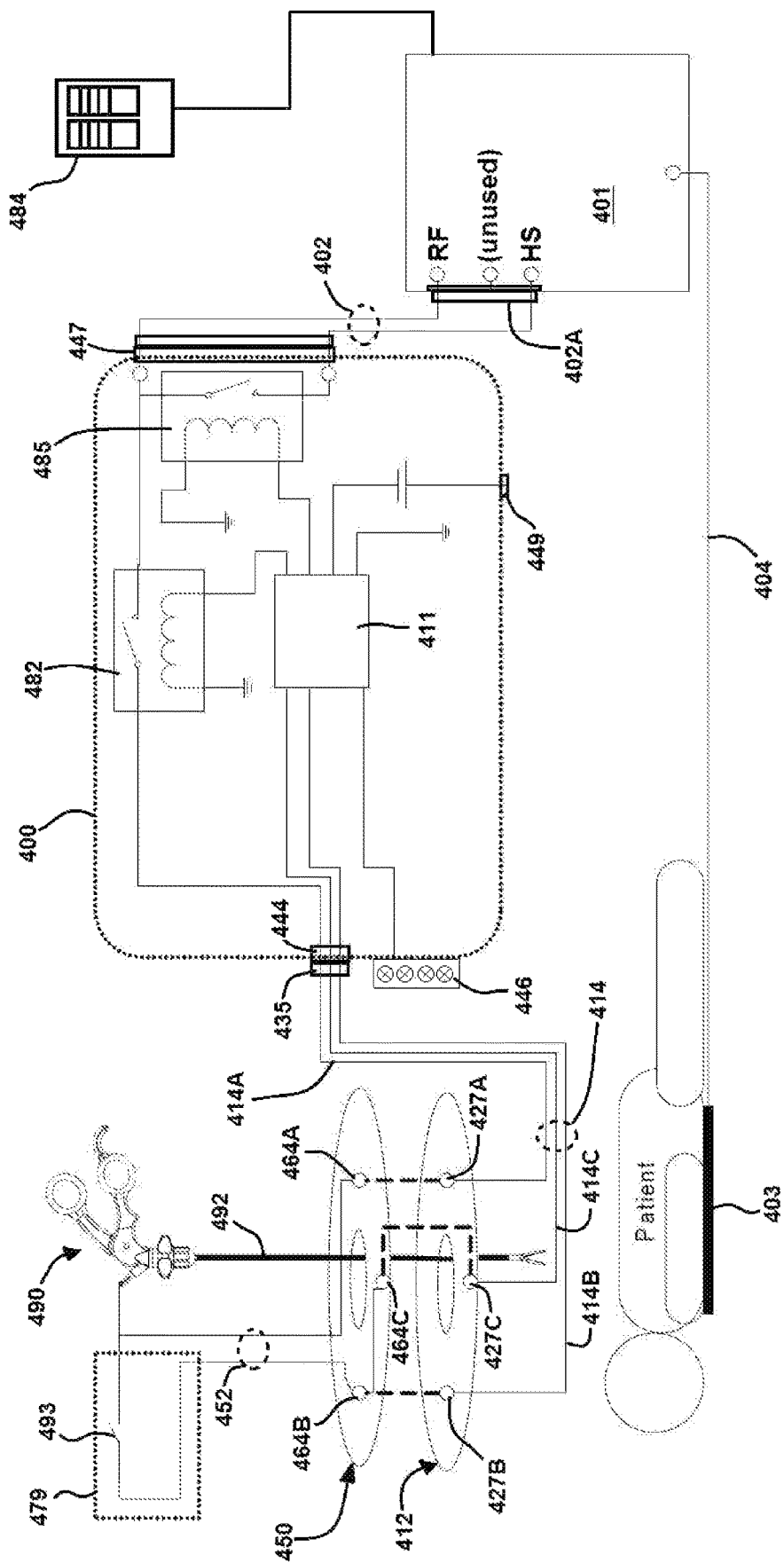
FIG. 52 is a schematic circuit diagram of an alternative embodiment of an electrosurgical system employing the MSIS and EDS of FIGS. 39-51.

For example, in one particular embodiment shown schematically in FIG. 52, first contact (464A) is used to deliver RF current to the surgical instrument contact, and second contact (464B) is in electrical communication with third contact (464C) (this electrical communication can be provided, for example, by a conductive trace within the PCB of cover plate (461) or on the proximal side thereof). As described below, this electrical communication between the second and third contacts (464B, 464C) of the instrument connector (450) provides a signal to the EDS (400) indicating mating engagement of the components of the MSIS (410). In the alternative embodiments of FIGS. 53-55, first contact (564A) is used to deliver RF current to the surgical instrument contact, and second contact (564B) is in electrical communication with third contact (564C) through a resistor (531A) of predetermined resistance. As described below, the electrical communication between the second and third contacts (564B, 564C) of the instrument connector (550) provides a signal or predetermined voltage (due to the resistor (531A)) to the EDS (500) indicating mating engagement of the components of the MSIS.

The instrument connector (450) further includes a guide cap (473) having a cylindrical mounting post (475) and a tapered guide cone (476), with an annular shoulder (477) at the intersection of the mounting post (475) and the base of the guide cone (476). The mounting post (475) is sized to be received within the central aperture (457A) of the housing (451), with the shoulder (477) pressing against the distal face of the cover plate (461) (see FIG. 39). The guide cap can be press fit in place and/or held in position by one or more of adhesive, mechanical fasteners such as screws or rivets, and press fitting.

The guide cone (476) is tapered in outer diameter along its length in order to guide the mating connection of the instrument connector (450) and the signal interface adapter (412). The guide cone (476) also helps to properly center the instrument connector with respect to the signal interface adapter (412), ensuring that the mating contacts and apertures are properly aligned. On its interior, and as best seen in FIG. 43, the internal bore of the guide cone (476) includes first and second tapers (474A, 474B) such that the interior diameter of the guide cone (476) is smallest at the intersection of the first and second tapers (474A, 474B). This allows the shaft of the surgical instrument to move somewhat (i.e., wobble) in the interior of the trocar cannula with causing the MSIS components to become disengaged. Also, by locating the intersection of the first and second tapers (474A, 474B) at the largest outer diameter region of the guide cone (476) (near the same plane as the cover plate of the signal interface adapter) further increases the stability of the mating connection of the MSIS components since the instrument shaft will bear against the interior bore of the guide cone where it is bolstered (on the outside of the guide cone) by the signal interface adapter (i.e., where the fit between the outer diameter of the guide cone and the interior of the signal interface adapter is most snug). This acts to limit the torque that might otherwise cause the MSIS components to become disengaged.

The instrument connector (450) is configured to be slidably mounted on an instrument shaft, as best seen in FIG. 44. The instrument shaft (492) is slidingly received through the central bore of the guide cone (473) of the instrument connector (450) such that the connector can slide axially and rotatingly along at least a portion of the instrument shaft. The instrument connector (450) can be configured for operable attachment to a surgical instrument in a wide variety of ways, depending, in part, on the configuration of the surgical instrument and the electrical connections thereto.

In the embodiment shown in FIGS. 39-49, instrument cable (452) is permanently attached at one end to the instrument connector (450) and includes two conduits (e.g., wires) therein. These conduits are in electrical communication with the first and second contacts (464A, 464B) on the distal face of the instrument connector (450), as seen schematically in FIG. 52. The instrument connecting end of the instrument cable (452) is configured similar to that described above for FIGS. 34-38, and is adapted for use with monopolar forceps (also referred to as a monopolar dissector) having a post connector (496) (see FIG. 44A) that is in electrical communication with the end effector electrode (e.g., one of the jaw members).

Instrument (490) includes an end effector (492A) at the distal end of shaft (492), with a handle assembly (494) located at the proximal end of the shaft, with the handle assembly having a stationary handle (494A) and a moveable (i.e., pivoting) handle (494B) for closing the jaw members of the end effector. Once again, the surgical instrument (490) is not manufactured with hand switches, and is therefore designed for use with footswitch activation by the user. However, the embodiment of FIGS. 39-49 provides a hand switch (479) that can be retrofit to a surgical instrument (e.g., instrument (490)) to provide hand switch control of the instrument using an existing external electrical device (e.g., a RF generator). In addition, particularly when used with EDS (400) described below, the hand switch (479) provides a hand switch signal to a hand switch port on an external electrical device (e.g., a RF generator) rather than a signal emulating a footswitch signal. Thus, the hand switch (479) allows for hand switch control of an instrument that is not manufactured with an integral hand switch.

As best seen in FIG. 44A, the instrument handle assembly (494) includes a post connector (496) that is in electrical communication with the end effector electrode (e.g., one of the jaw members). The distal end of the instrument cable (452) includes a female plug connector (497) configured for operative engagement with the post connector (496). As best seen in the exploded view of FIG. 47, the female plug connector (497) comprises first and second shell housings (497A, 497B) and a conductive sleeve (497C) housed therein. The conductive sleeve (497C) is configured to fit snugly over the post (496) of the surgical instrument, and is in electrical communication with the first conductor (452A) of the instrument cable (452). The second conductor (452B) is not in electrical communication with the conductive sleeve (497C), however, each conductor (452A, 452B) is in electrical communication with one of the poles of the switch (479) via switch cable (498).

Figure 48:
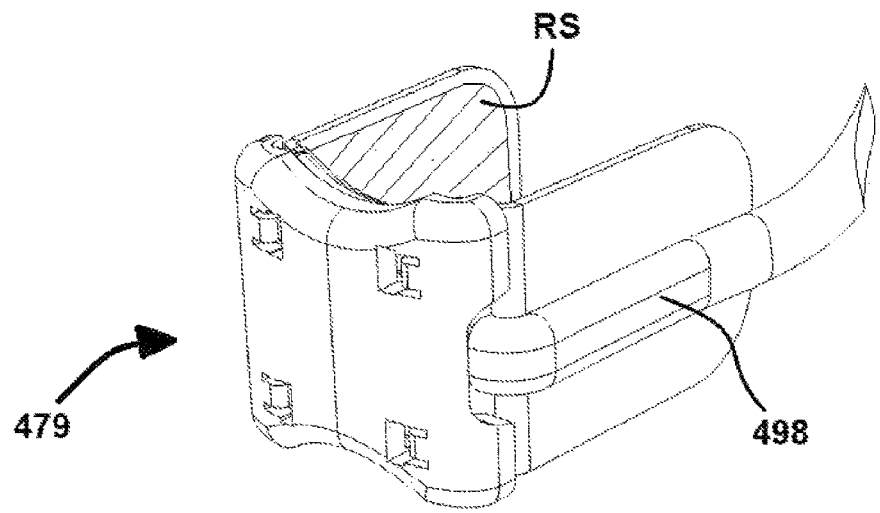
FIGS. 48 and 49 depict details of the switch assembly of FIG. 46.
Figure 49:
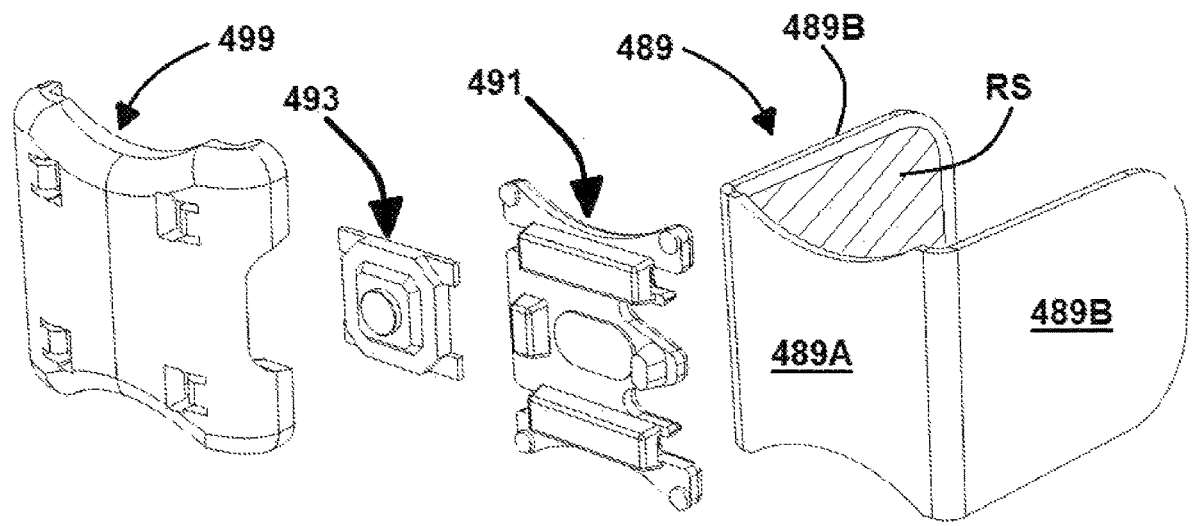

Switch assembly (479) is configured as a single-pole, single-throw ("SPST") switch configured for attachment to the handle assembly of a surgical instrument (e.g., handle assembly (494) of instrument (490)). As best seen in FIGS. 48 and 49, switch assembly (479) includes a flexible switch substrate (489) comprising a base portion (489A) and a pair of wings (489B) extending away from opposite sides of the base portion (489A). At least a portion of a first side of the substrate (489) includes an adhesive layer for releasably attaching the switch assembly (479) to a surgical instrument. A removable release sheet (RS in FIG. 49) is provided over the adhesive layer, and is removed to expose the adhesive layer for attaching the switch assembly (479) to an instrument (e.g., to the handle assembly or housing of a surgical instrument). The flexible nature of the switch substrate (489), particularly where the wings (489B) meet the base portion (489A), facilitates the secure attachment of the switch assembly (479) to an instrument at a variety of user-selectable locations. In FIG. 44, for example, the switch assembly (479) is shown adhered to the handle assembly (494) just above the stationary handle (494A). The adhesive layer can be applied across the bottom surfaces of both the wings (489B) and the base portion (489A), or only the bottom surfaces of the wings (489B) (similar to an adhesive bandage). The flexible nature of the switch substrate (489) allows the switch assembly (479) to be attached to a surgical instrument in a manner similar to attaching an adhesive bandage, flexing the switch substrate (489) to match the shape of a portion of the instrument where the user desires to attach switch assembly (479). In some embodiments, switch substrate (489) is also stretchable to further facilitate attachment, and/or the adhesive is releasable such that the switch assembly (479) can be removed (e.g., to sterilize the instrument). Of course, it will be understood that the switch assembly (479) can be configured for attachment to a surgical instrument in a variety of other ways (e.g., one or more fasteners).

Switch assembly (479) further comprises a base member (491) attached to the upper surface (i.e., the side facing away from the instrument and any adhesive), and provides a more rigid support for a tactile, pushbutton switch (493). A cover plate (499) is secured over the pushbutton switch (493) in order to provide a larger actuating surface and to protect the pushbutton switch. The pushbutton switch (493) is in electrical communication with the first and second conductors (452A, 452B) of the via the switch cable (498), and actuation of the switch (493) places the first and second conductors (452A, 452B) in electrical communication with each other (depicted schematically in FIG. 52). Thus, when the user actuates (i.e., presses) the cover plate (499) of switch assembly (479), a signal is passed through the mated instrument connector (450) and signal interface adapter (412) to EDS (400), from where a hand switching signal is transmitted to the generator (401) (or other external electrical device). Optionally, one or more additional buttons or other switches may be provided on the instrument for controlling the delivery of RF current from the generator. It will also be noted from FIG. 52 that in this embodiment a footswitch (484) can optionally be connected to the footswitch port on generator (401) in the usual manner.

EDS (400) for use with the MSIS of FIGS. 39-39 is depicted in FIGS. 50-52, and once again is configured to be operatively connected to an external electrical device (e.g., a RF electrosurgical generator (401). In this embodiment, however, a single, two conductor cable (402) is used for both the power supply line (or conduit) (e.g., for high voltage RF current) for transmitting RF current to the instrument (490) and the control signal line for transmitting a hand switch control signal to the generator (401). Commercially available generators have a single connector for both RF current and hand switching signals. While these generators typically have three-socket connectors (one for RF and two for hand switching signals), EDS (400) only transmits one hand switch signal via one pin of a connector provided at the remote end of cable (402). Thus, while the connector (402A) at the remote end of cable (402) can include three (or more) pins for compatibility with the connector on a commercial RF generator, one of those pins will not transmit signals (i.e., will not be live). As before, in the case of monopolar use, energy is returned to the generator (401) through one or more return electrodes (403) in conductive contact with the patient, via a return line (404).

As before, EDS (400) acts as a circuit breaker between the generator (401) and the instrument (490), mediated by the MSIS (410). The EDS (400) is configured such that RF power can only be transmitted from the generator (401) to the instrument (490) when the instrument connector (450) is matingly engaged with the signal interface adapter (412). The power delivery circuit within EDS (400) that places the power supply line of cable (402) in electrical communication with power conductor (414A) is closed when the components of MSIS (410) are in mating engagement. EDS (400) includes logic (e.g., a microprocessor (411)) that detects whether there is mating engagement between the instrument connector (412) and the signal interface adapter (450). When mating engagement is detected (e.g., from a voltage resulting from the mating engagement of contacts on the MSIS), the microprocessor (411) or other logic circuitry in the EDS (400) causes the closure of first relay (482) (e.g., a reed relay) placing the power supply line from the generator in electrical communication with power conductor (414A). Once again, it will be understood, however, that closure of the power delivery circuit in the EDS (400) does not mean that RF current is delivered to the end effector of the instrument (490). Rather, the medical practitioner still must activate the generator (i.e., cause the generator to deliver RF current along the power supply line) by actuating hand switch (479). Upon activation by the user, RF current is delivered to the treatment site adjacent the end effector of the instrument (490).

Figure 50:
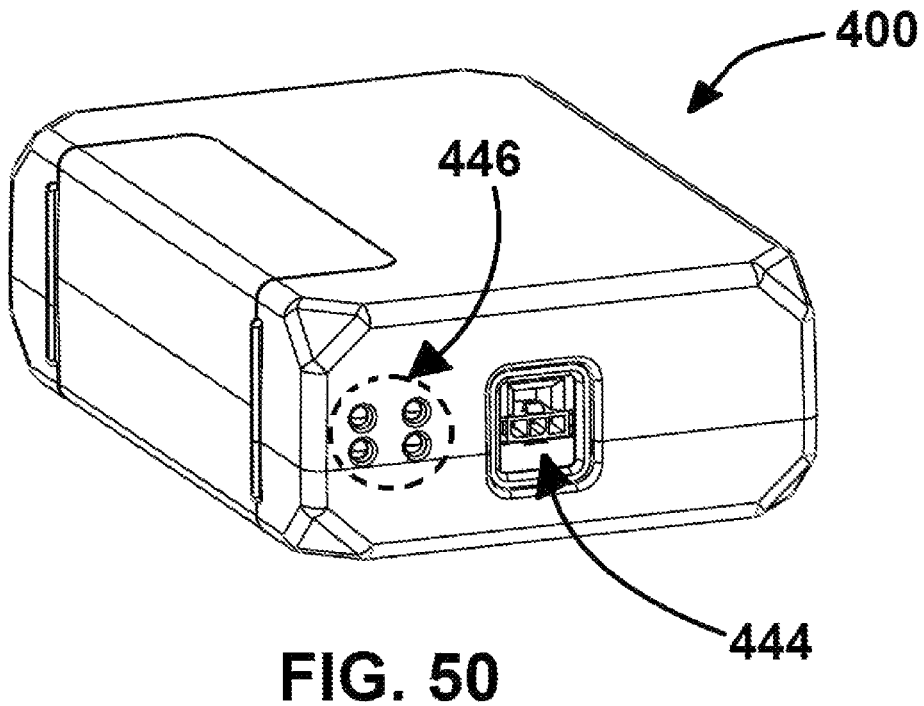
FIGS. 50 and 51 are front and rear perspective views of an alternative embodiment of an EDS similar to the views of FIGS. 29 and 30.
Figure 51:
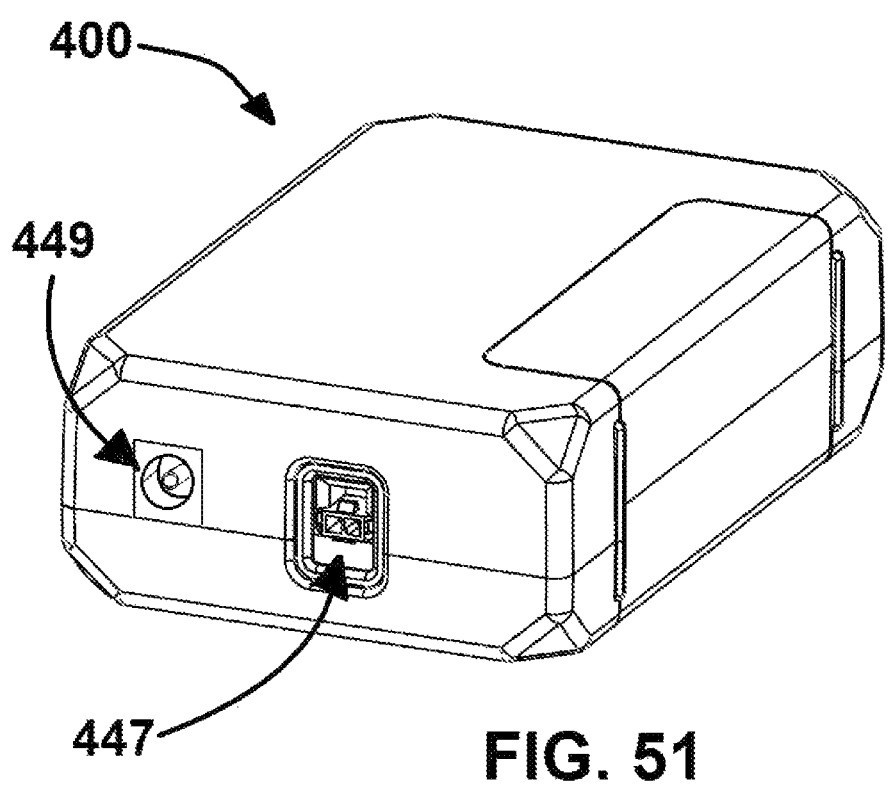

FIGS. 50 and 51 depict front and rear views, respectively, of the EDS (400), and FIG. 52 is a schematic view of the EDS (400), with the bottom cover removed, and the printed circuit board and certain other electronic components omitted for clarity. FIG. 52 is a schematic circuit diagram of the EDS (400), which omits some of the circuit isolation features described previously for EDS (200). It will be understood that the MSIS (410) and EDS (400) are shown schematically in FIG. 52 and are not drawn to scale with respect to the instrument. Also, the cables are depicted schematically in FIG. 52 as distinct conductors rather than as a cable having internal conductors (i.e., the outer sheaths of the cables are omitted in FIG. 52).

The front of the EDS (400) case includes a first connector (444) for operatively receiving the connector (435) on the end of the main cable (414). Thus, first connector (444) is a 3-socket female connector. The front of the case also includes various indicator LED's (446) for signaling operational parameters of the EDS (e.g., one or more LEDs configured to light and/or change color upon detection of mating engagement of the MSIS components, and one or more LEDs configured to light and/or change color upon activation of the switch (479)). The rear of the EDS (400) case includes a second connector (447) for operatively connecting to the cable (402) from the generator. In this instance, second connector (447) is a 2-socket female connector, since only two conduits are needed in cable (402). The EDS (400) includes a power connector (449) for attachment to a power source (e.g., a 12V DC power source). Of course, EDS (400) can also (or alternatively) be configured to include an internal power supply such as a rechargeable battery.

The EDS (400) further includes one or more processors (e.g., microprocessor (411)) or other logic (i.e., control) circuitry for controlling the operation of the EDS and the sending of a hand switch signal to the generator. When the instrument connector (450) and the signal interface adapter (412) become matingly engaged, first contact (427A) is in conductive contact with first contact (464A), second contact (427B) is in conductive contact with second contact (464B), and third contact (427C) is in conductive contact with third contact (464C). Accordingly, since the second and third contacts (464B, 464C) of the instrument connector (450) are in electrical communication with each other, the low power conductors (414B, 414C) of main cable (414) will be in electrical communication with each other (via the second and third contacts (427B/464B, 427C/464C of the MSIS (410)). The EDS (400) is configured such that a voltage signal is received by the microprocessor, indicating mating engagement of the components of the MSIS (410). Upon receipt of this voltage signal, the microprocessor (411) provides a closure signal to relay (482) (e.g., a reed relay switch), which places power supply line (402) in electrical communication with power conductor (414A) (see FIG. 52). However, RF power is not yet delivered over this electrically communicative path to the surgical instrument (490) until an actuation signal is provided to the generator (either a hand switch signal from the EDS (400) or from an optional footswitch (484) connected to the generator (401)).

Upon actuation of the retrofit hand switch (479) by the user, a voltage signal indicative of switch closure is provided to the microprocessor (411). Microprocessor (411) is adapted to transmit a closure signal to second relay (485) upon detection of a switch closure signal. Like first relay (472), second relay (485) acts as a normally open SPST switch. Closure of second relay (485) provides a hand switch signal to the generator (401), wherein this hand switch signal is equivalent to the signal that would be provided to the generator if a hand switched surgical instrument were connected to the generator and its hand switch activated. In this manner, the EDS (400) in combination with the MSIS (410) allows a hand switch to be retrofit to a surgical instrument. For example, electrosurgical monopolar forceps (dissector) (490), which normally could only be operated via foot switch control, can be hand switch operated in conjunction with a conventional generator.

As before, in some embodiments the EDS (400) is configured such that second relay (485) will not close unless high voltage first relay (482) is also closed. In this manner, the generator (401) will only be activated if the MSIS components are in mating engagement (i.e., the surgical instrument is inside the trocar cannula, ready to be used). In alternative embodiments, the closing of the low voltage second relay (485) is not dependent upon the status of high voltage first relay (482).

It will be understood that, although MSIS (410) is depicted and described as having only three communication channels (i.e., three conductive, mating contacts on each component), MSIS (410) can be modified to include any number of mating contacts and communication channels. For example, the cover plates (421, 461) can be modified so that each has four mating contacts arranged in a predetermined pattern around the central apertures (425, 463), thus allowing MSIS (410) to be used in conjunction with a pair of retrofit hand switches (e.g., similar to hand switches (279A, 279B) and EDS (200) (or similar EDS having a pair of low voltage relays for causing switch signals to be delivered to a generator or other external electrical device (e.g., emulating footswitch signals, or in the form of hand switch signals conducted to a hand switch signal port on the generator). It will also be understood that EDS (400) and/or MSIS (410) can include various other circuitry and electrical components for signal conditioning, resistors for voltage signal regulation, etc.

Figure 53:
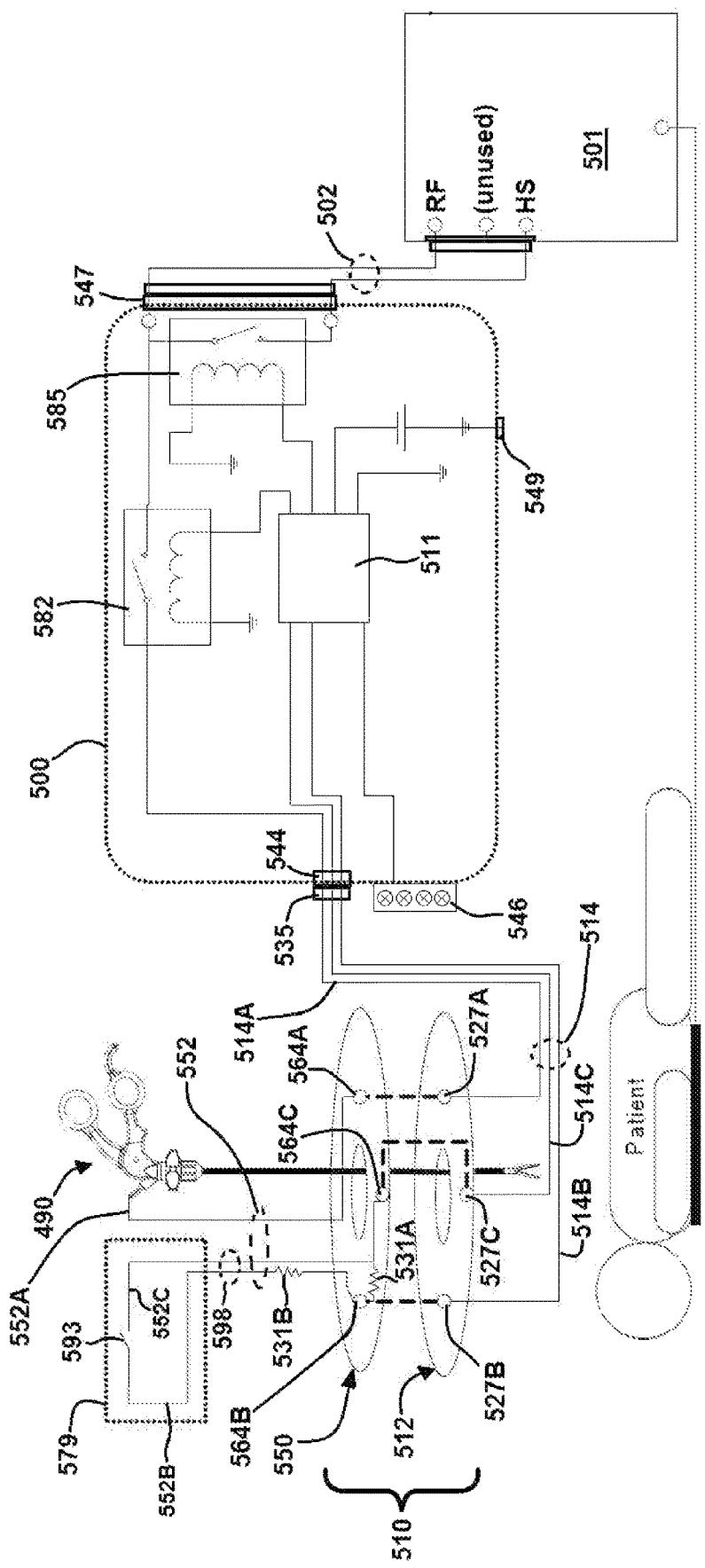
FIG. 53 is a schematic circuit diagram of yet another alternative embodiment of an electrosurgical system, similar to the view of FIG. 52.
Figure 54:
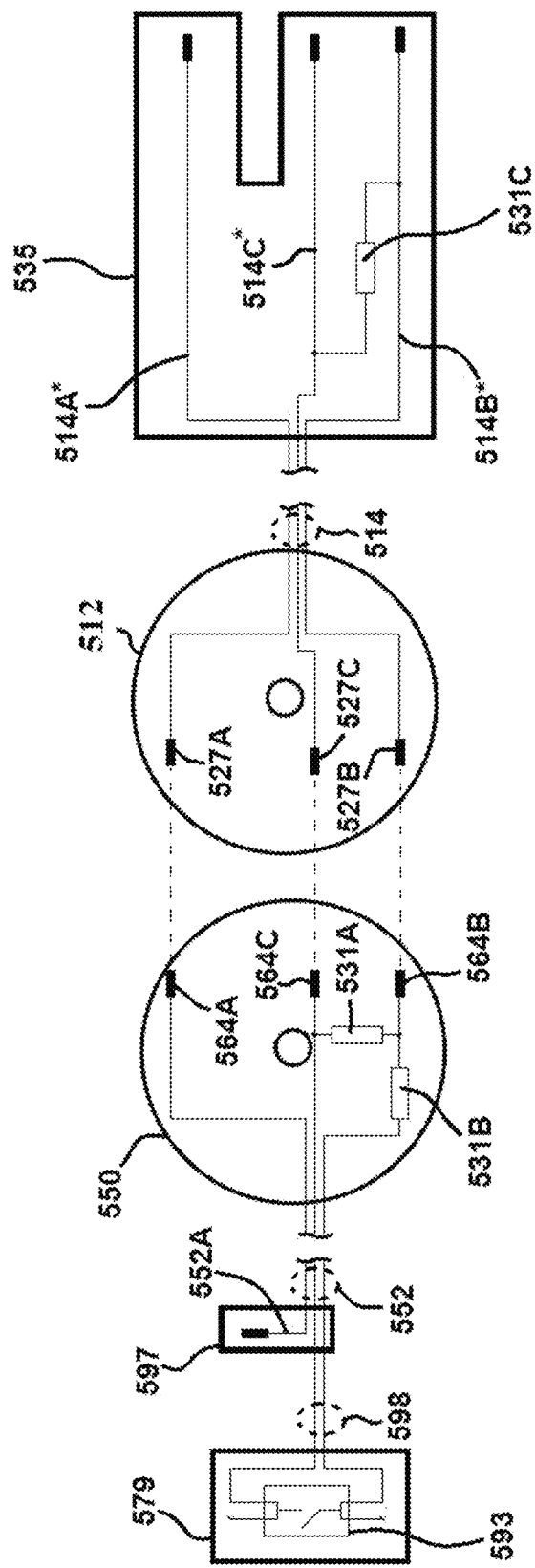
FIG. 54 is a schematic illustration of various connectors, cables and MSIS components of the same system.

FIGS. 53 and 54 schematically depict an alternative embodiment of an EDS (500) for use with a modified MSIS (510) comprising a signal interface adapter (512) and an instrument connector (512). FIG. 53 schematically depicts the cables (and their connections) as well as the mating faces of the components of the MSIS (510) EDS (500) is configured similar to EDS (400), and includes a microprocessor (511), a first connector (544) for operatively receiving a connector (535) on the end of the main cable (514) from the signal interface adapter (512), various indicator LED's (546), a second connector (547) for operatively connecting to the cable (502) from a generator (501), and a power connector (549) for attachment to a power source (e.g., a 12V DC power source). Of course, once again EDS (500) can also (or alternatively) be configured to include an internal power supply such as a rechargeable battery. EDS (500), like EDS (400), further includes a high voltage first relay (582) that, when triggered, places power supply line (502) in electrical communication with power conductor (514A) of the main cable (514). EDS (500) also includes a low voltage second relay (585) that, when triggered, sends a hand switch signal to the generator. Once again, main cable (514) is permanently attached at one end to the signal interface adapter (512) and includes three conduits (e.g., wires) therein. These conduits are in electrical communication with the three contacts (527A-C) on the proximal face of the signal interface adapter (512).

The three conductive contacts (527A-C) on the signal interface adapter (512) are once again configured for mating engagement with three conductive contacts (564A-C) on the instrument connector (512). In this embodiment, however, second contact (564B) is in electrical communication with third contact (564C) through a resistor (531A) of predetermined resistance located in the instrument connector (550). A low system voltage is applied to conductors (514C, 552C), and a first signal voltage is provided by conductor (514B) to the EDS (500). When the components of the MSIS (510) are in mating engagement, a voltage of predetermined level (based on the predetermined resistance of resistor (531A)) will be present on conductor (line) (514B). The EDS (500) is configured to sense this predetermined voltage as an indication of mating engagement of the MSIS components (512, 550), and the microprocessor (511) will cause the closure of first relay (582).

The embodiment of FIG. 53 also includes an instrument cable (552) having a female plug connector (597) similar to plug connector (497) of the previous embodiment. (The plug connector is not shown in FIG. 53.) The plug connector is configured for operative engagement with a post connector on the surgical instrument (490). Unlike the previous embodiment, the instrument cable (552) has three, rather than two, conductors therein. One conductor (552A) delivers high power RF current to the post connector of the instrument, while the other two conductors (552B, 552C), located within the switch cable (598) extending between the plug connector and the hand switch assembly (579). Thus, in contrast to the previously described embodiment, the switch detection circuit is isolated from the high power conductor (552A).

A retrofittable hand switch assembly (579) similar to hand switch assembly (479) of the previous embodiment is provided in the embodiment of FIG. 53. Actuation of this switch (e.g., by pressing pushbutton switch (593)), places the switch conductors (552B, 552C) in electrical communication. A second resistor (531B) of predetermined resistance different from that of first resistor (531A) (e.g., lower resistance) is located along second switch conductor (552B) between pushbutton switch (593) and second contact (564B) of the instrument connector (550). Although second resistor (531B) is depicted in FIG. 53 as being external to the instrument connector (550) (e.g., within cable (552) or cable (598)), second resistor (531B) is alternatively provided within the instrument connector itself (as shown in FIG. 54). Upon actuation of the hand switch assembly (579), with the low system voltage applied to conductors (514C, 552C), a second signal voltage of predetermined level (based on the predetermined resistance of resistor (531B)), different from the first signal voltage, is provided by conductor (514B) to the EDS (500). The EDS (500) is configured to sense this predetermined second voltage as an indication of hand switch actuation by the user, and the microprocessor (511) will cause the closure of second relay (582). This results in a hand switch signal being provided to the generator, thereby resulting in the delivery of RF current to the instrument (490). Of course, it will be understood that EDS (500) and MSIS (510) can be configured to detect mating engagement of the components of the MSIS as well as hand switch activation in a variety of other manners.

MSIS (510) also includes a modified connector (535) at the EDS engaging end of the main cable (514), as shown in FIG. 54. Connector (535) is in the form of a PCB with conductive traces (514A*, 514B*, 514C*) in electrical communication with the high power conductor (514A) and the low power conductors (514B, 514C), respectively. The PCB is housed within an outer casing (not shown), with the proximal ends (the far right side in FIG. 54) of the conductive traces exposed for operative connection with a correspondingly configured female connector (544) on the EDS (500). Use of a PCB for the connector (535) also allows the high power and low power traces to be physically separated, as shown, in order to provide additional safety.

Second and third conductors (i.e., traces) (514B*, 514C*) in the connector (535) are in electrical communication through a third resistor (531C) of predetermined resistance different from that of first and second resistors (531A, 531B). The third resister (531C) is located in the connector (535). When connector (535) is properly connected to the female connector (544) on the EDS (500), the low system voltage will be applied to conductor (514C*) and a third signal voltage of predetermined level (based on the predetermined resistance of resistor (531C)), different from the first and second signal voltages, will be provided by conductor (514B*) to the EDS (500). The EDS (500) is configured to sense this predetermined third voltage as an indication that the main cable (514) of the signal interface adapter (512) has been operatively connected to the EDS (500). This results in one or more LEDs on the EDS (500) becoming lit and/or changing color, indicating proper connection to the EDS (500). In some embodiments, and audible signal can also be provided by the EDS upon proper connection of main cable (514), mating engagement of the MSIS components, activation of the hand switch(es), and/or detection of a failure such as a short or other non-standard condition. By way of example, if there is a short the EDS (500) will detect a higher than expected voltage signal from conductor (514B) and the EDS (500) will not turn on or, if already powered, will shut down.

Figure 55:
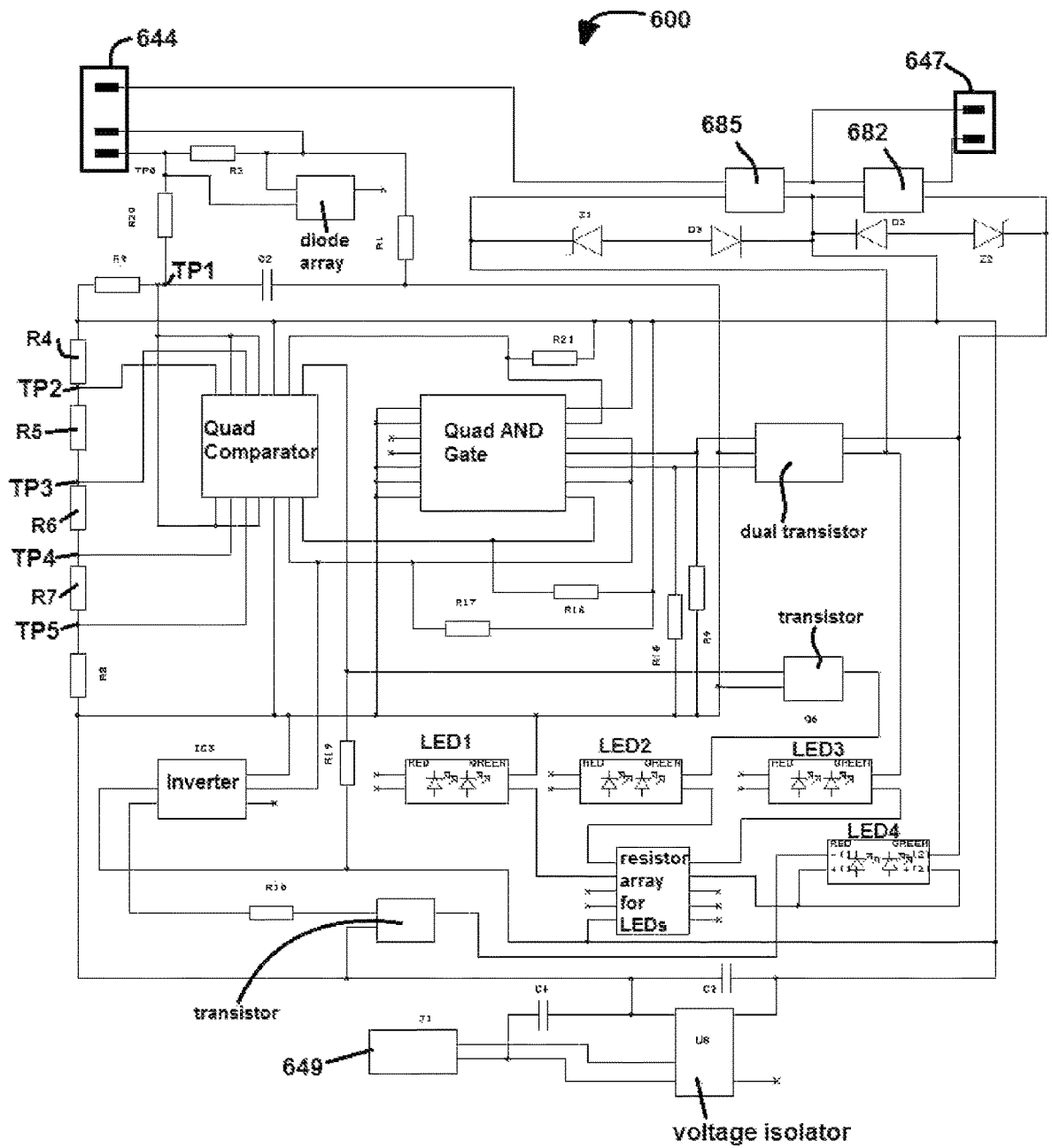
FIG. 55 is a schematic circuit diagram of another alternative embodiment of an EDS according to the present disclosure.

Finally, FIG. 55 is a schematic illustration of yet another embodiment of an EDS (600) configured to be operatively connected: to a connector (535) of main cable (514) of MSIS (510) via first connector (644); to a generator (not shown) via second connector (647); and to a power source (e.g., a 12V DC power source) via power connector (649). In this embodiment, the microprocessor has been replaced by, among other things, at least one Comparator and at least one AND Gate.

In the specific example shown, a Quad Comparator and a Quad AND Gate are employed. EDS (600) monitors the voltage of a sense line (Test Point #1; "TP1") and compares the sense line voltage to reference voltages (TP2, TP3, TP4, & TP5) to determine if and when to activate different functions (e.g., close relays, activate indicators, etc.). The reference voltages are created by four resistors (R4, R5, R6 and R7) of predetermined resistance, the resistors in series with one another and produce different reference voltages at TP2, TP3, TP4 and TP5). The reference voltages are proportional to the system voltage. Voltage comparisons are done using the four comparators, shown combined in a single integrated circuit (i.e., a Quad Comparator).

Before main cable (514) of the MSIS (510) is connected to EDS (600), TP1 voltage will be higher than TP2, TP3 and TP4 (and TP5, assuming there is no short), and therefore the comparator outputs associated with TP2-TP4 will be low.

No action is taken by the EDS (600) except that Green-LED1 will be lit, indicating the EDS has power. After main cable (514) of the MSIS (510) is connected to EDS (600), TP1 voltage will drop below that of TP2 due to the resistor (531C) in connector (535). However, TP1 voltage will be higher than TP3 and TP4. As a result, the comparator output associated with TP2 will be high, while the others will continue to be low. The high level of the comparator output associated with TP2 will result in the Green-LED2 being lit to indicate that the connector (535) has been attached to first connector (644) of the EDS (600).

When a surgical instrument having instrument connector (550) is inserted through the signal interface adapter (412) such that the MSIS components become matingly engaged, TP1 voltage will drop below that of TP3 due to resistor (531A) in the instrument connector (550) of the MSIS. However, TP1 voltage will be higher than TP4. As a result, the comparator output associated with TP3 will be high, while the comparator output associated with TP4 will stay low (TP5 will be high if there is no short, as noted below). TP3 and TP5 outputs are both checked to see if they are high using the Quad AND Gate. If this is true, the associated AND Gate output is high and is used as a closure signal for the first reed relay (682). As a result, Green-LED3 is lit to indicate the mating engagement of the MSIS components (i.e., the instrument is full inserted into the trocar cannula, ready for use), and first reed relay (682) is closed to prepare the monopolar circuit.

When the hand switch (593) is actuated, closing the circuit within the switch assembly (579), TP1 voltage will be fall even lower, to below TP4, due to the resistor (531B) in the instrument connector (550). As a result, the comparator output associated with TP4 will be high. TP4 and TP5 output are both checked to see if they are high using the Quad AND Gate. If this is true, the associated AND Gate output is high and is used as a closure signal for the second reed relay (685). As a result, Green-LED4 is lit to indicate actuation of the hand switch (593), and second reed relay (685) is closed to signal the generator to deliver monopolar power.

During use, TP1 is also compared to TP5 to detect if there is a short in the cable system or elsewhere. The output from this comparison is high until TP1 voltage falls below TP5 voltage, indicating a short. If TP1 voltage falls below TP5, the comparator associated with TP5 will go low, causing the two AND Gate outputs associated with TP3 and TP4 to go low. As a result, both relays (682, 685) are opened (and the corresponding LEDs will go dark), terminating the actuating signal to the generator (i.e., ceasing RF output) and galvanically isolating the instrument from the generator. Simultaneously, the inverter goes high, causing Red-LED4 to be lit, signaling an error.

It should be understood that the quad comparator, quad AND gate, and inverter control LEDs and relays by use of transistors and resistors to regulate current and the like. Capacitors, diodes, and other electrical components are used to smooth voltage fluctuations and optimize the reliability and safety of the system under different conditions and standards such as IEC 60601.

It will be understood that the exemplary schematics and descriptions herein are not intended to provide a detailed blueprint for manufacturing the EDS of the present disclosure. Therefore the EDS includes a variety of conventional components in addition to those described above, such components for regulating various voltages, reducing signal noise, circuitry for monitoring battery condition, circuitry for activating indicator LEDs (46), etc. By way of example, the indicator LEDs (46) can display various colors indicating the engagement status of the MSIS (i.e., is there mating engagement), the status of the footswitch pedals and hand switches, whether the EDS is attached to a generator, etc. Any of the alternative MSIS embodiments and features described in Appendix A can also be employed with the systems and methods of the present disclosure.

The EDS and associated MSIS described herein can be used with a wide variety of signal-associated surgical instruments. As used herein, a "signal-associated surgical instrument" is a surgical instrument that receives and/or supplies one or more electrical signals to an external device, wherein those electrical signals can comprise power signals (e.g., current or voltage) and/or communication signals (e.g., a sensor signal). Signal-associated surgical instruments include powered surgical instruments (particularly those configured for use though a cannula), as well as, for example, instruments used for: ultrasonic cutting/cautery, ultrasonic imaging, focused ultrasound, radio frequency cautery, radio frequency cutting, radio frequency ablation, stapling, sensing, imaging, measuring, robotic, haptic, cutting, grinding, clamping, thermal, radio-isotopic, drug delivery, biopsy, hyperspectral imaging, insufflation, and/or suturing.

In some alternative embodiments, the EDS is passive in that it only closes the high voltage relay (50) when mating engagement of the MSIS is detected, without having the additional feature of footswitch emulation for hand switch signals. In other embodiments, various additional electronic circuitry is provided in the EDS such as, for example, an IC chip or other component for identification purposes (e.g., to identity the type of instrument engaged through the MSIS. Other suitable circuitry can include one or more sensors for detecting various conditions related to the electrical connection of the two components of the MSIS or even for detecting one or more conditions related to the trocar, the surgical instrument or the use of either in a surgical environment.

As yet another alternative, the EDS can be configured to have more than one high voltage monopolar input and more than one low power control signal input so that the EDS can be used with two electrosurgical instrument/MSIS systems. Such an alternative would include and additional set of a high voltage relay (50) and low voltage relays (56, 57) for operation and control of the send instrument.

While specific embodiments are described herein in conjunction with monopolar forceps, it will be understood that the EDS and MSIS can be used with a variety of signal-associated surgical instruments, including RF instruments (bipolar and monopolar, e.g., monopolar forceps, monopolar pencils, monopolar scissors, bipolar forceps, bipolar pencils, bipolar scissors), electrocautery instruments, and ultrasonic instruments (e.g., ultrasonic blades, ultrasonic probes, ultrasonic shears). Thus, it will be understood that the components, features and configurations, as well as the methods of manufacturing the devices and methods described herein are not limited to the specific embodiments described herein.

What is claimed is:

1. An engagement detection system ("EDS") adapted to be positioned between, and in electrical communication with, an electrosurgical generator and an electrosurgical instrument, the EDS adapted to electronically detect that the electrosurgical instrument is inserted into a cannula of a trocar, and thereafter deliver electrosurgical energy to the instrument, the EDS comprising (a) a first connector for operably connecting the EDS to the electrosurgical instrument;

(b) a second connector for operably connecting the EDS to the electrosurgical generator;

(c) a first switch mediating electrical communication between the first connector and the second connector; and (d) a control circuit adapted to receive a first signal indicative of the electrosurgical instrument being inserted into the cannula of the trocar and generate a switch signal for controlling operation of said first switch, said first signal received from the electrosurgical instrument or the trocar;

wherein the EDS is configured such that the electrosurgical energy can only be transmitted from the electrosurgical generator to the electrosurgical instrument when the electrosurgical instrument is inserted into the cannula of the trocar;

wherein said control circuit is adapted to compare the first signal received from the instrument or the trocar to a plurality of reference signals, and determine that the electrosurgical instrument is inserted into the cannula of the trocar based on the result of that comparison; and wherein said control circuit is further adapted to receive a second signal from the instrument or the trocar and compare the second signal to said plurality of reference signals, and determine that a hand switch has been actuated by a user based on the result of that comparison.

2. The EDS of claim 1, further comprising a second switch, wherein said control circuit is further adapted to receive a switching signal from a switching device and, in response to said switching signal, cause an actuation signal to be supplied to the electrosurgical generator for controlling the electrosurgical energy supplied by the generator to the instrument.

3. The EDS of claim 1, wherein said first switch comprises a first relay.

4. The EDS of claim 2, wherein said first switch comprises a first relay, and said second switch comprises a second relay.

5. The EDS of claim 4, wherein said relays comprise reed relays.

6. The EDS of claim 3, wherein said control circuit:
if said first signal indicates that the shaft of the electrosurgical instrument is inserted into the cannula of the trocar, causes said first relay to close, thereby placing the electrosurgical instrument and the generator in electrical communication.

7. The EDS of claim 6, wherein said control circuit receives said first signal from a signal interface adapter mounted on the trocar.

8. The EDS of claim 1, further comprising a third connector, wherein said first connector is adapted for receiving a power signal from the generator and said third connector is adapted for communicating an actuation signal from the EDS to the generator.

9. The EDS of claim 8, wherein said EDS is adapted to communicate the actuation signal to a footswitch input on the generator.

10. The EDS of claim 1, wherein said first connector is adapted for both receiving a power signal from the generator and communicating an actuation signal from the EDS to the generator.

11. The EDS of claim 1, wherein said control circuit receives said first signal from a signal interface adapter mounted on the trocar.

12. The EDS of claim 3, wherein said control circuit comprises a plurality of comparators adapted for comparing the first and second signals received from the instrument or the trocar to said plurality of reference signals for controlling operation of the EDS, and further comprising at least one AND Gate for receiving outputs from the comparators and providing at least one closure signal for said first relay.

13. An engagement detection system ("EDS") adapted to be positioned between, and in electrical communication with, an electrosurgical generator and an electrosurgical instrument, the EDS adapted to electronically detect that the electrosurgical instrument is inserted into a cannula of a trocar, and thereafter deliver electrosurgical energy to the instrument, the EDS comprising (a) a first connector for operably connecting the EDS to the electrosurgical instrument;

(b) a second connector for operably connecting the EDS to the electrosurgical generator;

(c) a first switch mediating electrical communication between the first connector and the second connector; and (d) a control circuit adapted to receive a first signal indicative of the electrosurgical instrument being inserted into the cannula of the trocar and generate a switch signal for controlling operation of said first switch, said first signal received from the electrosurgical instrument or the trocar;

wherein the EDS is configured such that the electrosurgical energy can only be transmitted from the electrosurgical generator to the electrosurgical instrument when the electrosurgical instrument is inserted into the cannula of the trocar;

further comprising a second switch, wherein said control circuit is further adapted to receive a switching signal from a switching device and, in response to said switching signal, cause an actuation signal to be supplied to the electrosurgical generator for controlling the electrosurgical energy supplied by the generator to the instrument;

wherein said first switch comprises a first relay;

wherein said control circuit comprises a microprocessor, and further comprising a DC-to-DC converter located between the microprocessor and said first relay such that, upon determining that the electrosurgical instrument is inserted in the trocar cannula, the microprocessor provides a closure signal to said first relay through the DC-to-DC converter.

14. An electrosurgical system comprising,
an engagement detection system ("EDS") adapted to be positioned between, and in electrical communication with, an electrosurgical generator and an electrosurgical instrument having a shaft, the EDS adapted to electronically detect that the electrosurgical instrument is inserted into a cannula of a trocar, and thereafter deliver electrosurgical energy to the instrument; and a modular signal interface system ("MSIS") for providing electrical communication between the EDS and the electrosurgical instrument when the electrosurgical instrument is inserted into the cannula of the trocar;

wherein said MSIS comprises:

(a) a signal interface adapter provided on, or adapted to be mounted on the trocar, the signal interface adapter having a central aperture extending therethrough and a plurality of conductive contacts; and (b) an instrument connector provided on, or adapted to be mounted on the shaft of the surgical instrument, the instrument connector having a central aperture extending therethrough and a plurality of conductive contacts, the instrument connector adapted for providing electrical communication between one or more of said contacts and the surgical instrument on which the instrument connector is provided or adapted to be mounted;

wherein the signal interface adapter and the instrument connector are adapted for mating engagement such that, when matingly engaged, said central apertures are axially aligned and one or more of the plurality of contacts of the signal interface adapter are in conductive contact with one or more of the plurality of contacts of the instrument connector.

15. The electrosurgical system of claim 14, wherein the EDS further comprises:
 a first connector for operably connecting the EDS to the electrosurgical instrument;
 a second connector for operably connecting the EDS to the electrosurgical generator; and
 a first switch mediating electrical communication between the first connector and the second connector.

16. The electrosurgical system of claim 15, wherein the EDS further comprises:
 a control circuit adapted to receive an electronic signal indicative of the electrosurgical instrument being inserted into the cannula of the trocar such that the signal interface adapter and the instrument connector are matingly engaged, and generate a switch signal for controlling operation of said first switch;
 wherein the EDS is configured such that the electrosurgical energy can only be transmitted from the generator to the instrument when the instrument is inserted into the cannula of the trocar such that the signal interface adapter and the instrument connector are matingly engaged.

17. A method of controlling an operation of an endoscopic electrosurgical instrument inserted into a cannula of a trocar, comprising:
 electronically detecting, by the EDS of claim 1 positioned between and in electrical communication with an electrosurgical generator and the electrosurgical instrument, that the electrosurgical instrument is inserted into the cannula; and
 thereafter delivering electrosurgical energy from the electrosurgical generator to the instrument for use in treatment.

18. The method of claim 17, wherein the step of detecting that the electrosurgical instrument is inserted into the cannula comprises detecting mating engagement between a signal interface adapter provided on the trocar, and an instrument connector provided on the electrosurgical instrument.

19. The method of claim 18, wherein the step of delivering the electrosurgical energy to the instrument comprises receiving an first electronic signal indicative of mating engagement between the signal interface adapter and the instrument connector, and, in response thereto, electronically closing the first switch of the EDS so as to provide electrical communication between the electrosurgical generator and the instrument.

20. The method of claim 19 wherein said first switch of the EDS comprises a reed relay.

21. The method of claim 17, wherein said step of delivering the electrosurgical energy to the instrument comprises, receiving, by the control circuit of the EDS, the second signal and, in response to determining that the hand switch has been actuated by the user, the control circuit of the EDS causes an actuation signal to be supplied to the electrosurgical generator.

* * * * *